US012779013B2

(12) United States Patent
Bhattacharya Babwah et al.

(10) Patent No.: US 12,779,013 B2
(45) Date of Patent: Nov. 3, 2026

(54) MODIFIED KISSPEPTIN RECEPTOR AGONISTS FOR FATTY LIVER DISEASE

(71) Applicant: Rutgers, The State University of New Jersey, New Brunswick, NJ (US)

(72) Inventors: M. Moshmi Bhattacharya Babwah, New Brunswick, NJ (US); Andy Videsh Babwah, New Brunswick, NJ (US); Sally Radovick, New Brunswick, NJ (US); Fredric E. Wondisford, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 910 days.

(21) Appl. No.: 17/995,720

(22) PCT Filed: Apr. 8, 2021

(86) PCT No.: PCT/US2021/070363

§ 371 (c)(1),
(2) Date: Oct. 7, 2022

(87) PCT Pub. No.: WO2021/207759

PCT Pub. Date: Oct. 14, 2021

(65) Prior Publication Data

US 2023/0256051 A1 Aug. 17, 2023

Related U.S. Application Data

(60) Provisional application No. 63/007,071, filed on Apr. 8, 2020.

(51) Int. Cl.
*A61K 38/08* (2019.01)
*A61K 38/17* (2006.01)
*A61K 45/06* (2006.01)
*A61P 1/16* (2006.01)

(52) U.S. Cl.
CPC .......... *A61K 38/1709* (2013.01); *A61K 38/08* (2013.01); *A61K 45/06* (2013.01); *A61P 1/16* (2018.01)

(58) Field of Classification Search
CPC ............ A61K 38/08; A61K 45/06; A61P 1/16
See application file for complete search history.

(56) References Cited

U.S. PATENT DOCUMENTS

| | | | |
|---|---|---|---|
| 8,642,339 | B2 | 2/2014 | Sato et al. |
| 10,583,484 | B2 | 3/2020 | Demuth et al. |
| 11,034,935 | B2 | 6/2021 | Huch Ortega et al. |
| 2004/0002519 | A1 | 1/2004 | Damon et al. |
| 2018/0258400 | A1 | 9/2018 | Ng et al. |
| 2020/0199537 | A1 | 6/2020 | Takebe et al. |
| 2020/0199538 | A1 | 6/2020 | Ng et al. |
| 2020/0354683 | A1 | 11/2020 | Hu et al. |

FOREIGN PATENT DOCUMENTS

| | | | | |
|---|---|---|---|---|
| WO | 03/80070 | A2 | 10/2003 | |
| WO | WO-03080070 | A2 * | 10/2003 | ................ A61P 3/08 |

OTHER PUBLICATIONS

Curtis et al., Am. J. Physiol. Endocrinol. Metab., 2010, vol. 298:E296-E303.*
ClinicalTrials.gov ID—NCT02369796 (Last Update Posted: Mar. 31, 2017).*
Bowe et al., Islets, 2012, vol. 4(1), 20-23.*
Madrigal's News Release (May 31, 2018).*
"International Search Report and Written Opinion of the International Searching Authority," issued in connection with Int'l Appl. No. PCT/US21/70363, dated Jul. 1, 2021 (6 pages).
Bowe, J. E. et al., "Kisspeptin stimulation of insulin secretion: mechanisms of action in mouse islets and rats", Diabetologia, vol. 52,No. 5, 2009, pp. 855-862.
Broutier, L. et al., "Culture and establishment of self-renewing human and mouse adult liver and pancreas 3D organoids and their genetic manipulation", Nature Protocols, vol. 11, 2016, pp. 1724-1743.
Clevers, H. et al., "Modeling Development and Disease with Organoids", Cell, vol. 165, No. 7, 2016, pp. 1586-1597.
Hu, H. et al., "Long-Term Expansion of Functional Mouse and Human Hepatocytes as 3D Organoids", Cell, vol. 175, No. 6, 2018, pp. 1591-1606.
Huch, M. et al., "In vitro expansion of single Lgr5+ liver stem cells induced by Wnt-driven regeneration", Nature, vol. 494, 2013, pp. 247-250.
Huch, M. et al., "Long-Term Culture of Genome-Stable Bipotent Stem Cells from Adult Human Liver" Cell, vol. 160, 2015, pp. 299-312.
Ibrahim, R. H. et al, Sexual Dimorphism in Serum Kisspeptin Level in Experimentally Induced Non-Alcoholic Fatty Liver Disease in Adult Albino Rats, American Journal of Biomedical Science, vol. 10, No. 2, 2018, pp. 115-128.
Levy, G. et al., "Long-term culture and expansion of primary human hepatocytes", Nature Biotechology, vol. 33, No. 12, 2015, pp. 1264-1271.
Peng, W. C. et al., "Tissue Repair Signals and In Vitro Culture: Inflammatory Cytokine TNFa Promotes the Expansion of Primary Hepatocytes in 3D Culture", Cell, vol. 175, No. 6, 2018, pp. 1607-1619.
Wang, B. et al., "Self-renewing diploid Axin2+ cells fuel homeostatic renewal of the liver", Nature, vol. 524, No. 7564, 2015, pp. 180-185.
Asami, et al., "Serum Stability of Selected Decapeptide Agonists of KISS1R using Pseudopeptides", Bioorganic & Medicinal Chemistry Letters, vol. 22, 2012, pp. 6391-6396.

(Continued)

*Primary Examiner* — Xiaozhen Xie
(74) *Attorney, Agent, or Firm* — Wolter Van Dyke Davis, PLLC; Eugene J. Molinelli; Martha Cassidy

(57) ABSTRACT

This invention involves repurposing the use of TAK-448 in NAFLD or NASH. In this study, a diet-induced mouse model of NAFLD was used to demonstrate that a hepatic knock-out of Kiss1r promotes steatosis. Moreover, infusion of the KP analog (TAK-488) in obese, wild-type diabetic mice protects against disease progression. Thus, the present invention provides a therapy for metabolic disorders such as NAFLD and NASH through the administration of TAK-488, a long-lasting synthetic analog of kisspeptin-10, a naturally occurring peptide found in the blood.

5 Claims, 58 Drawing Sheets

Specification includes a Sequence Listing.

(56) References Cited

OTHER PUBLICATIONS

Decourt, et al.. "A synthetic kisspeptin analog that triggers ovulation and advanced puberty", Nature.com/Scientific Reports, Jun. 1, 2026, pp. 1-10.
Guzman, et al., "Targeting hepatic kisspeptin receptor ameliorates nonalcoholic fatty liver disease in a mouse model", Journal of Clinical Investigation, vol. 132, Issue 10, 2022, pp. 1-45.
Izarraras, et al., "Kisspeptin Mitigates Hepatic De Novo Lipogenesis in Metabolic Dysfunction-Associated Steatotic Liver Disease", Cells 2025, vol. 14, 1289, pp. 1-19.
Nisizawa, et al., "A new class of pentapeptide KISS1 receptor agonists with hypothalamic-pituitary-gonadal axis activation", Bioorganic & Medicinal Chemistry Letters 2019, vol. 29, pp. 654-658.
Prasad, et al., "Kisspeptin Alleviates Human Hepatic Fibrogenesis by Inhibiting TGFβ Signaling in Hepatic Stellate Cells", Cells 2024, vol. 13, 1651, pp. 1-25.

* cited by examiner

LIVER

Control (RD)

LKO (RD)

LIVER

LIVER

Isolated Primary Hepatocytes

Isolated Primary Hepatocytes

Nuclei

Human NAFLD/ NASH Biopsy

Stellate Cell Marker (Desmin)

Kisspeptin receptor (KISS1R

Areas of colocalization of KISS1R and stellate cells (white bright cells)

Human Male Liver Biopsy

MODIFIED KISSPEPTIN RECEPTOR AGONISTS FOR FATTY LIVER DISEASE

CROSS-REFERENCE TO THE RELATED APPLICATION

This application claims priority to PCT Application No. PCT/US21/70363, filed Apr. 8, 2021, which claims the benefit of U.S. Provisional Patent Application No. 63/007,071, filed Apr. 8, 2020, under 35 U.S.C. § 119, which is incorporated herein by reference in its entirety.

BACKGROUND OF THE INVENTION

The liver is the principal organ involved in lipid metabolism. Dyslipidemia leads to metabolic disorders such as non-alcoholic fatty liver disease (NAFLD) which has become an increasing public health concern affecting approximately 1 billion individuals worldwide. In the U.S, NAFLD is a national epidemic that affects over 12 million adults and 8 million children, with associated annual medical costs of $103 billion.

NAFLD is the leading cause of liver disease worldwide. The prevalence of NAFLD mirrors the rise in obesity and type II diabetes. NAFLD is characterized by accumulation of liver fat (steatosis), leading to the generation of cytotoxic lipid oxidation by-products which progresses to a chronic inflammatory state with hepatocyte injury, defined as non-alcoholic steatohepatitis (NASH). As the disease advances, a subset of patients will develop fibrosis, cirrhosis and liver failure or hepatocellular carcinoma (HCC). NAFLD/NASH are expected to replace hepatitis C as the most common indication for liver transplantation in the next decade. Thus, NAFLD encompasses a spectrum of pathological conditions, including steatosis (fatty liver), non-alcoholic steatohepatitis (NASH), and fibrosis and cirrhosis (excessive scarring of liver).

Kisspeptins (KPs), the peptide products of the KISS1 gene, are endogenous ligands for the Kisspeptin 1 receptor (KISS1R), a G-protein coupled receptor. The KP/KISS1R signaling system is expressed both centrally and peripherally, where it plays a major role in reproduction and metabolism. In fact, liver Kiss1 expression was found to be increased in genetic models of obesity (db/db and ob/ob mice). Although KISS1 and KISS1R are expressed in the liver, a role for hepatic KISS1R signaling in regulating lipogenesis is not known.

The prevalence of NAFLD mirrors the rise in obesity and type II diabetes, affecting about 100 million Americans. Apart from weight-loss and bariatric surgery which is beneficial in the early stages of the disease, currently there are no FDA approved drugs to treat NAFLD/NASH. FDA guidance to industry has stated that "the FDA believes that identifying therapies that will slow the progress of, halt, or reverse NASH and NAFLD will address an unmet medical need." See fda.gov (December 2018).

Thus, there is a critical need to develop new treatments for NAFLD/NASH.

SUMMARY OF THE INVENTION

This invention involves repurposing the use of TAK-448 in NAFLD or NASH. In this study, a diet-induced mouse model of NAFLD was used to demonstrate that a hepatic knock-out of Kiss1r promotes steatosis. Moreover, infusion of the KP analog (TAK-488) in obese, wild-type diabetic mice protects against disease progression. Mechanistically, KP signaling was demonstrated to negatively regulate de novo lipogenesis by activating AMP-activated protein kinase (AMPK) and suppressing the peroxisome proliferator-activated receptor-γ (PPARγ) signaling pathway. This study provides direct evidence that both pharmacological and genetic interventions directed at KISS1R can protect against the development of NAFLD.

Specifically, the invention relates to a method of treatment or prevention of NAFLD/NASH in a subject in need thereof, comprising administering to the subject a therapeutically effective amount of TAK-448. Preferably, the subject is a NAFLD patient or a NASH patient. Administration may be by any route, but preferably is subcutaneous.

BRIEF SUMMARY OF THE DRAWINGS

FIG. 1A is a photograph of hematoxylin and eosin-stained mouse livers, where indicated (black arrowheads), showing steatosis, and liver lipid staining with Oil Red O, where indicated (red dots), for control (vehicle) and TAK-488-treated mouse livers (5mice/group). FIG. 1B through FIG. 1G show the beneficial effect of TAK-488 in lowering endpoint liver triglycerides (TGs) (FIG. 1B), endpoint blood glycerol (FIG, 1C), blood free fatty acids (FFA) (FIG. 1D), body weight (FIG. 1E), and peripheral fat accumulation in animals (FIG. 1F and FIG. 1G). FIG. 1H through FIG. 1J show that TAK-448 treatment prevented the rise in fasting glucose (FIG. 1H), prevented glucose intolerance as determined using a glucose tolerance test (GTT) (FIG. 1I), and prevented insulin resistance using insulin tolerance test (ITT) (FIG. 1J).

FIG. 2C shows no difference in food intake measured by CLAMS, 4 weeks post treatment; 10 weeks on RD/HFD; 5 mice/group. Mean + SEM shown, Student's unpaired t-test, *$p<0.05$ compared to VEH controls.

FIG. 5A shows the relative mRNA expression of indicated genes by RT-qPCR in HFD liver samples, normalized to Rpl13a mRNA expression. TAK-448 treatment reduces the levels of key genes regulating fat production in the liver (triglyceride synthesis and lipogenesis). FIG. 5B is a representative western blot showing expression of indicated protein in HFD livers mice. TAK-448 treatment decreases the protein levels of key regulators of fat production in the liver.

FIG, 11 is a graph relating to the inhibitory effects of TAK-448 treatment on expression of key regulators of hepatic inflammation.

Figure 12:
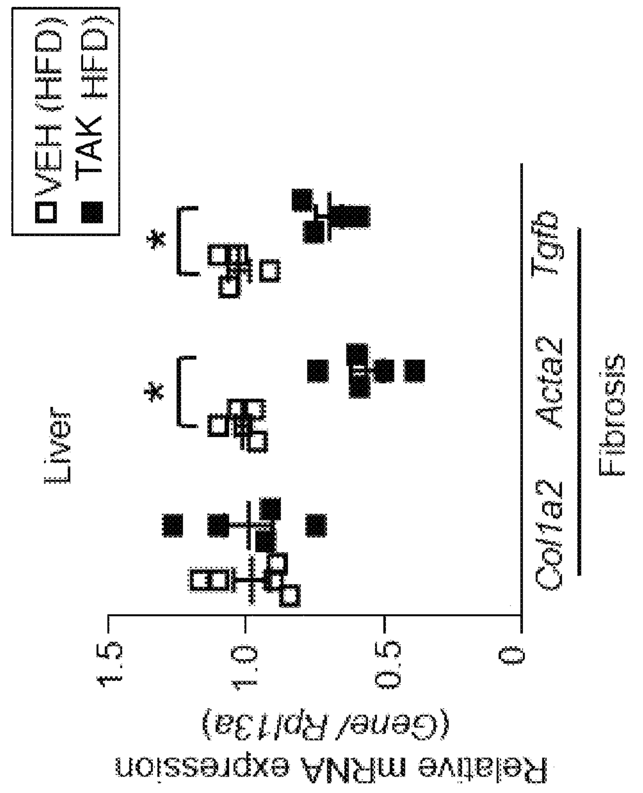

FIG. 12 is a graph relating to the effects of TAK-448 treatment on expression of key regulators of hepatic fibrosis.

Figure 13:
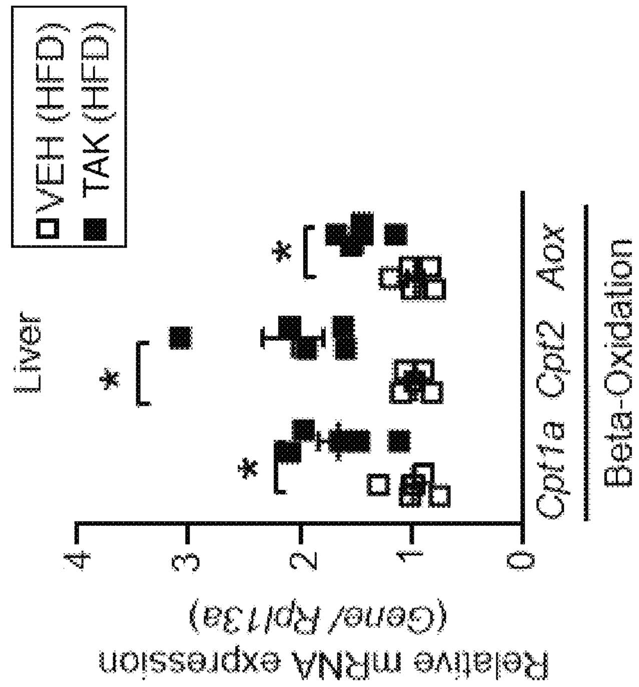

FIG. 13 is graph relating to the effects of TAK-448 treatment on expression of hepatic genes regulating mitochondrial and peroxismal beta-oxidation of fat.

Figure 14A:
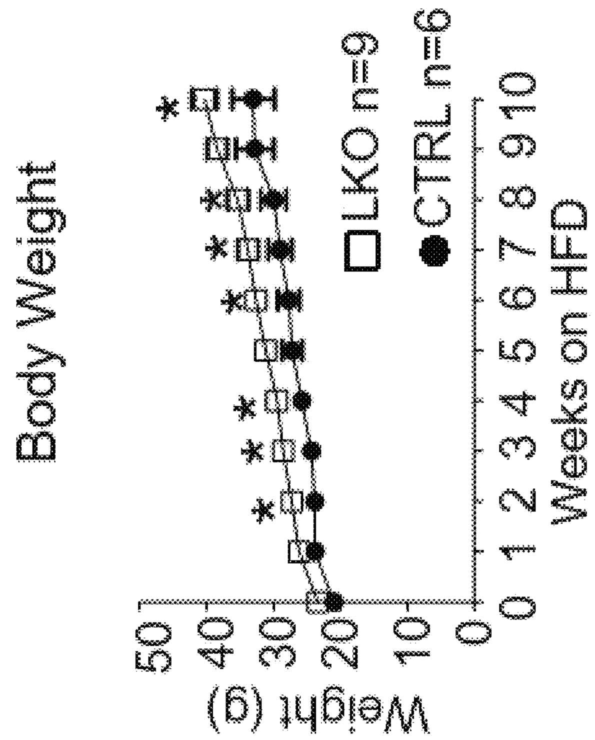
Figure 14D:
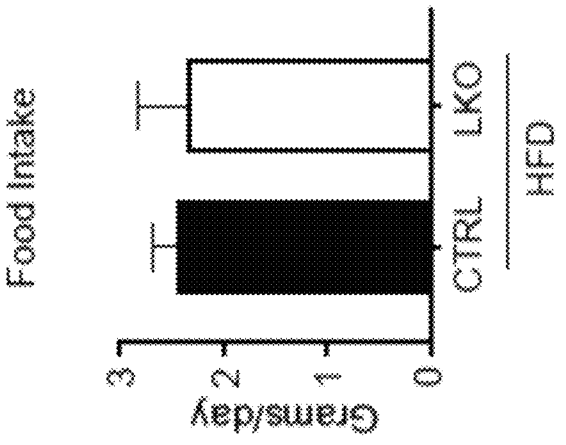
Figure 14C:
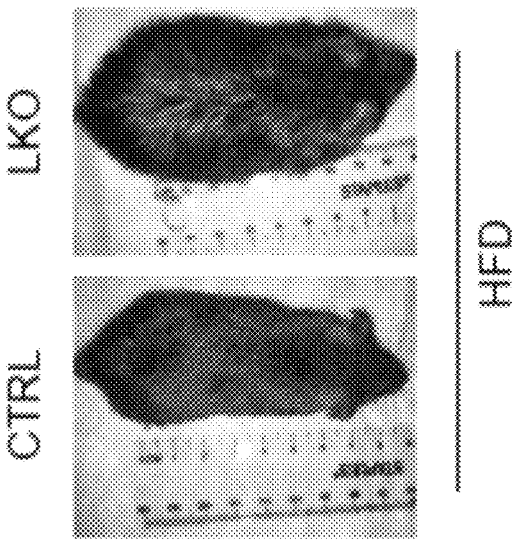
Figure 14B:
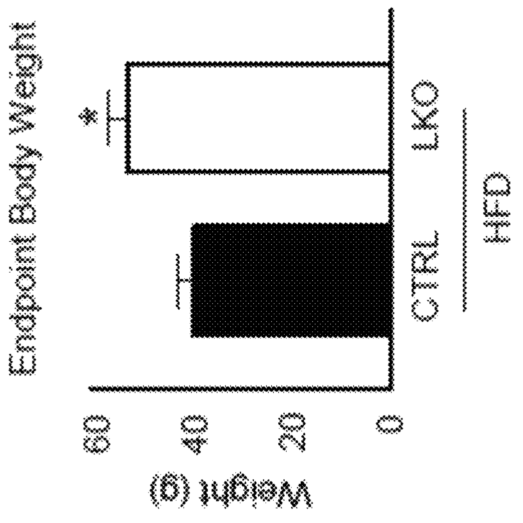

FIG. 14A through FIG. 14D. FIG. 14A is a graph showing body weight (BW) of control (CTRL, n=6) and liver KISS1R knock-out (LKO, n=9) mice over time on HFD. FIG. 14B is a bargraph showing endpoint body weight for control and LKO mice. FIG. 14C is a photograph of mice on HFD (CTRL and LKO), FIG, 14D is a bar graph showing daily food intake of control and LKO mice averaged over 4 days.

Figure 15A:
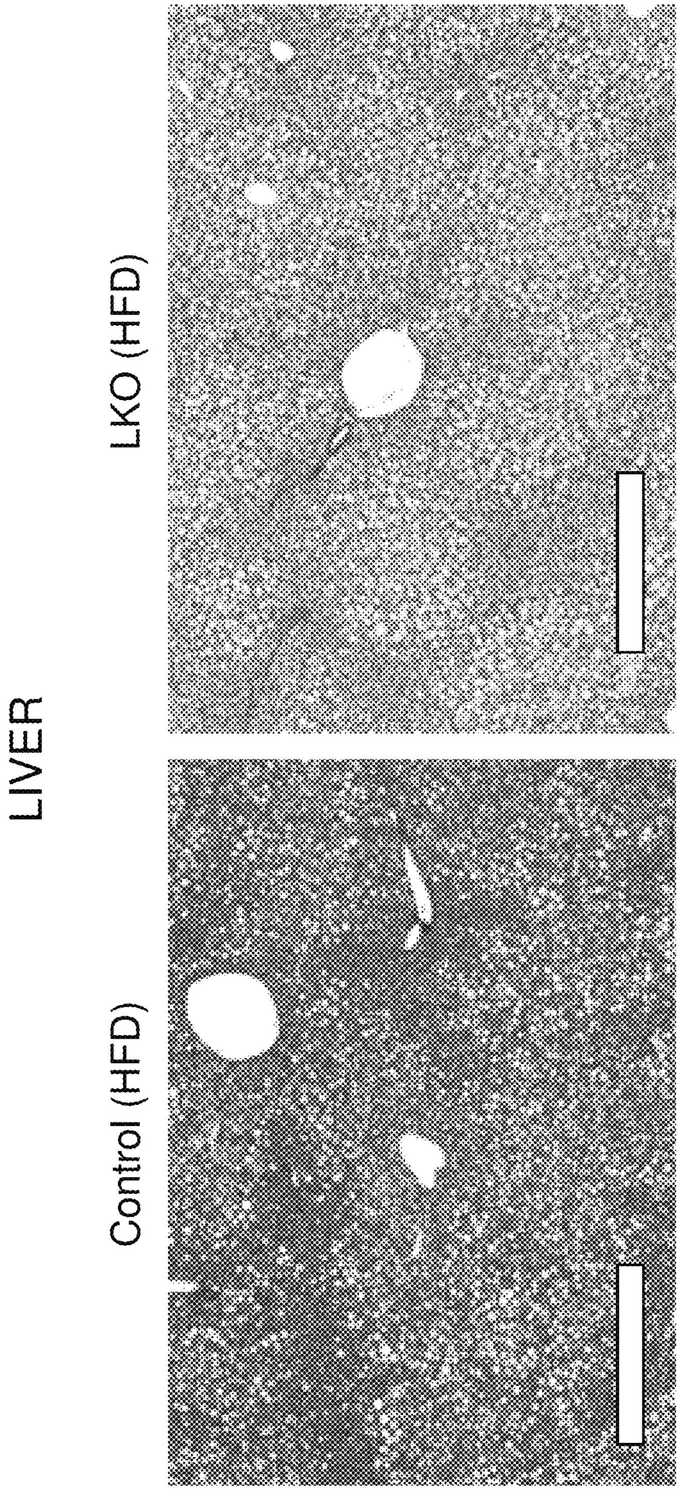
Figure 15B:
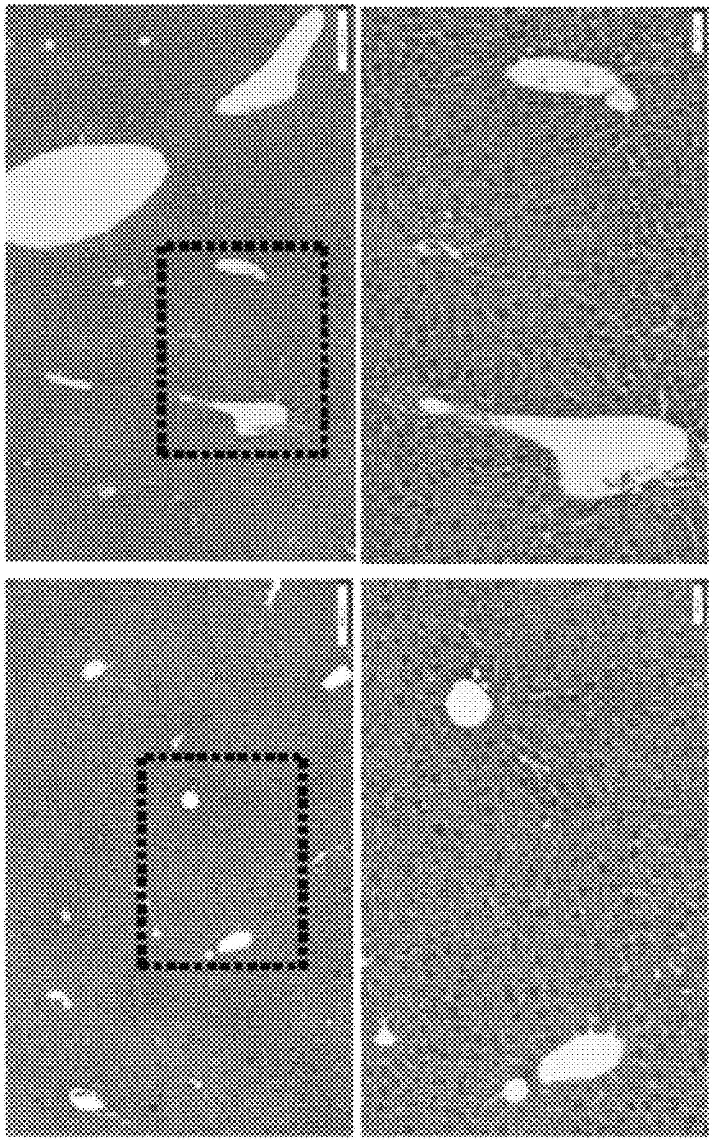

FIG. 15A and FIG. 15B are sets of micrographs of hematoxylin and eosin stained mouse liver showing steatosis for CTRL and LKO (HDF and RD) mice with high fat (FIG. 15A) and regular (FIG. 15B) diets.

Figure 16:
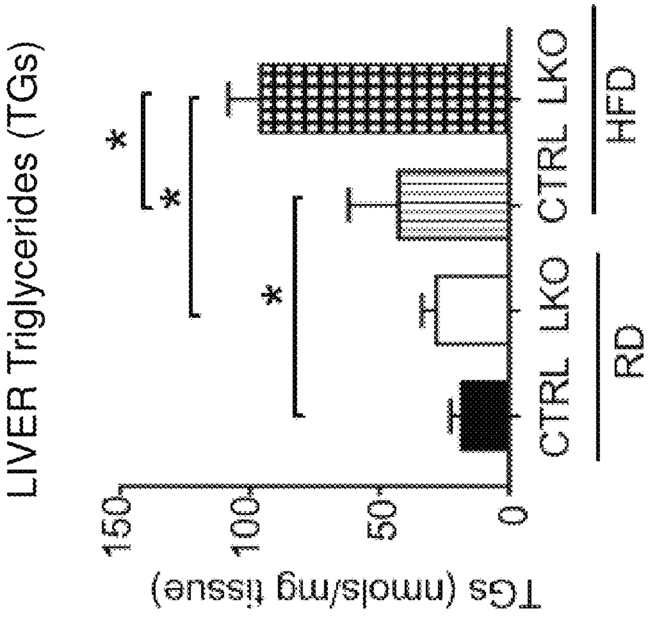

FIG. 16 is a bar graph showing liver triglycerides in CTRL and LKO (RD and HFD) mice.

Figure 17:
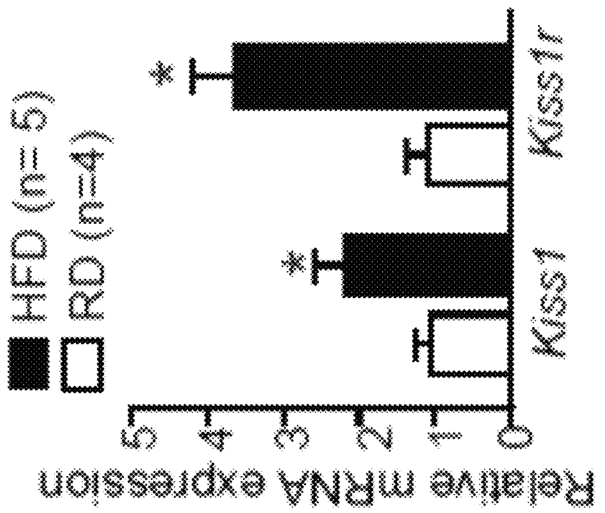

FIG. 17 shows the relative mRNA expression of Kiss1 and Kiss1r by RT-qPCR normalized to Rpl13a mRNA expression in C57BL6 male mice on regular diet (RD) or high fat diet (HFD) for 8 weeks.

Figure 18A:
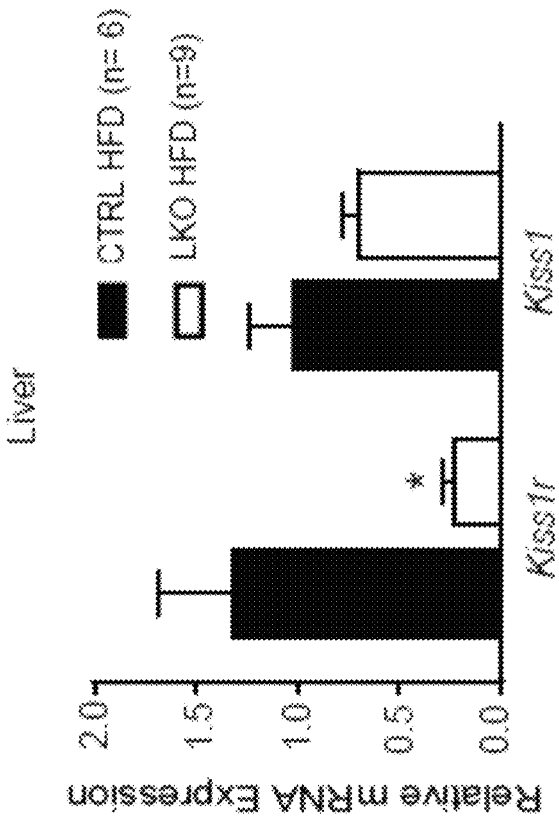
Figure 18B:
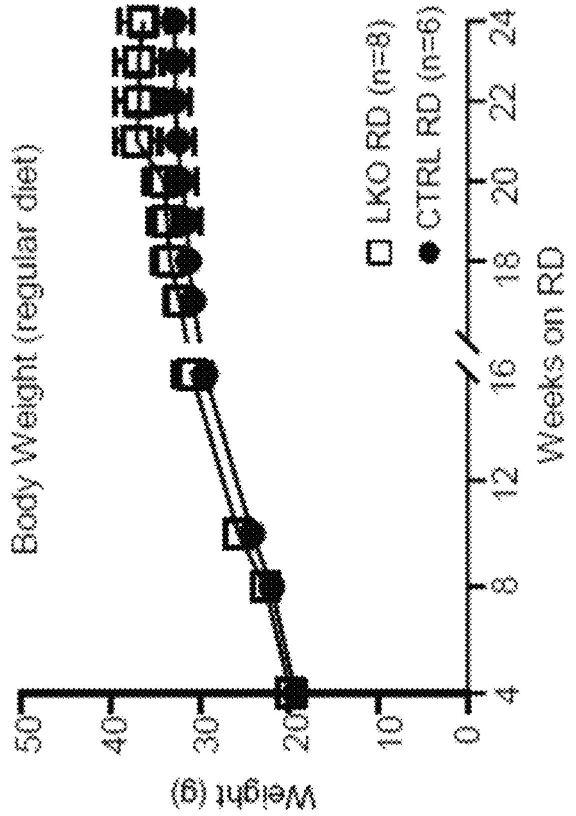
Figure 18D:
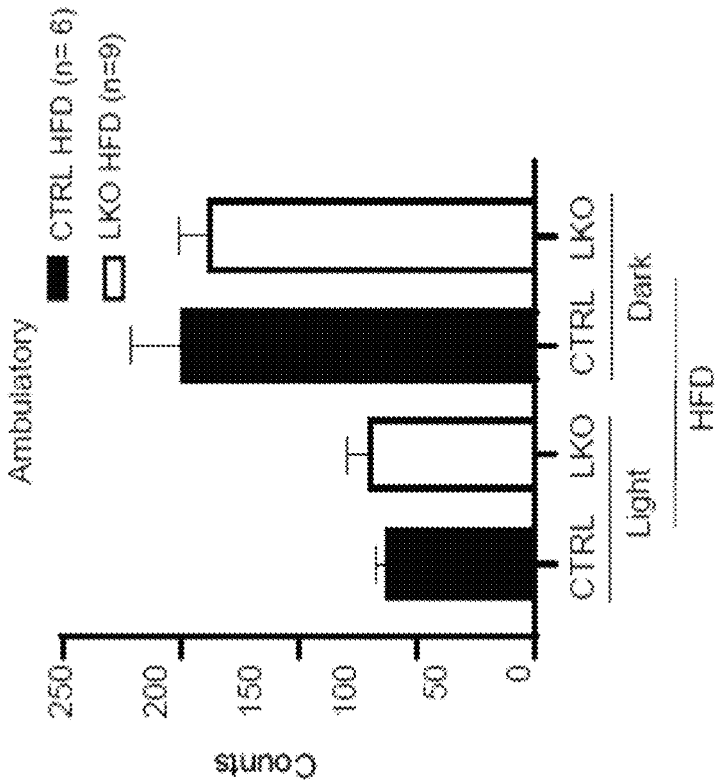
Figure 18C:
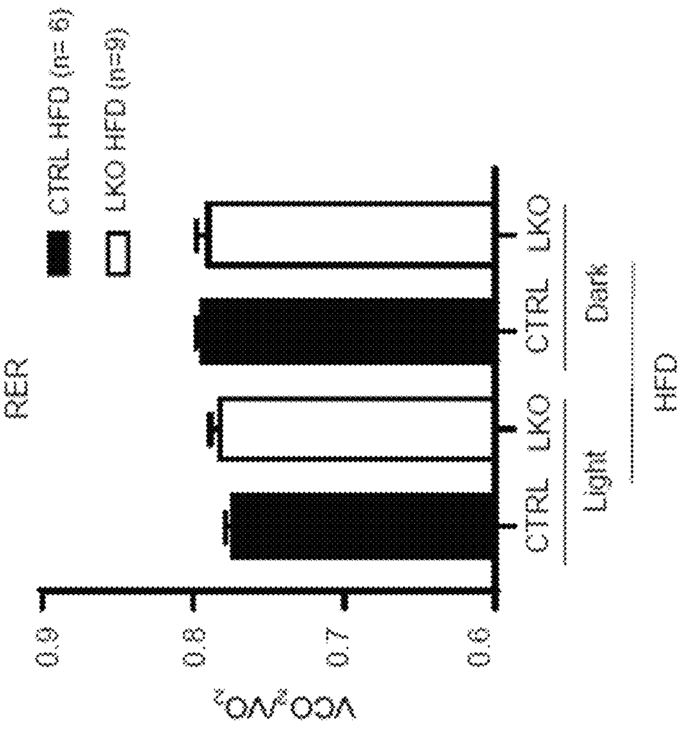

FIG. 18A through FIG. 18D. FIG. 18A shows the relative mRNA expression of indicated genes by RT-qPCR in HFD livers from CTRL and LKO mice. Mean ± SEM shown, Student's unpaired t-test. *p<0.05 compared to controls. FIG. 18B shows the body weight of CTRL and LKO mice on regular diet (RD). FIG. 18C and FIG. 18D show CLAMS analysis displaying respiratory exchange ratio (RER) (FIG. 18C) and ambulatory activity (FIG, 18D) of CTRL and LKO mice. * p<0.05; One-way ANOVA followed by Dunnett's post-hoc test.

Figure 19B:
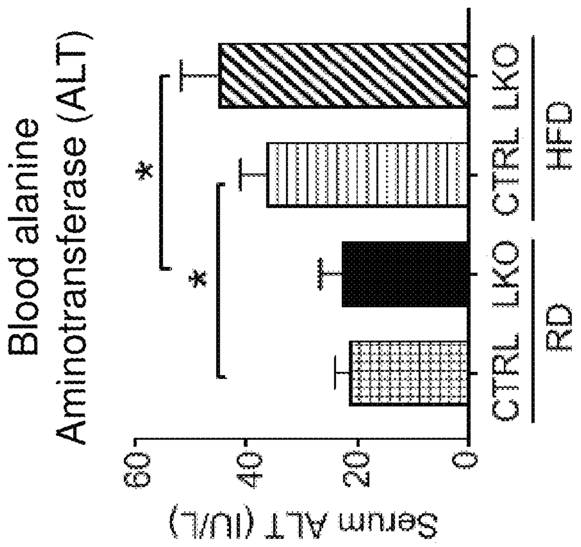
Figure 19A:
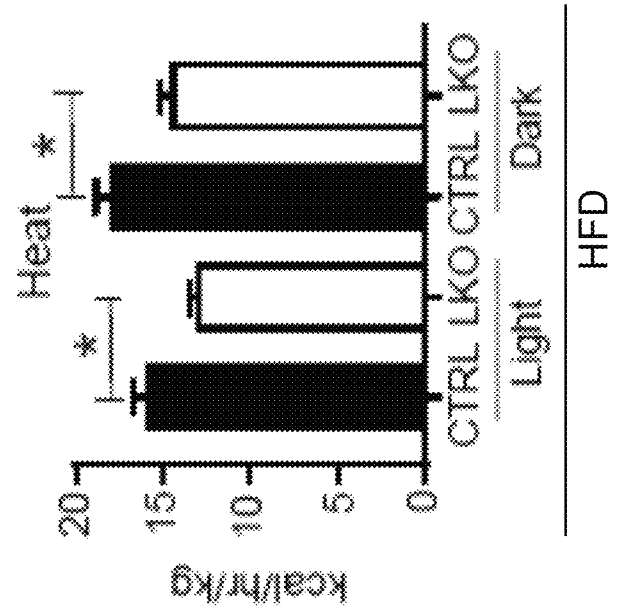
Figure 20B:
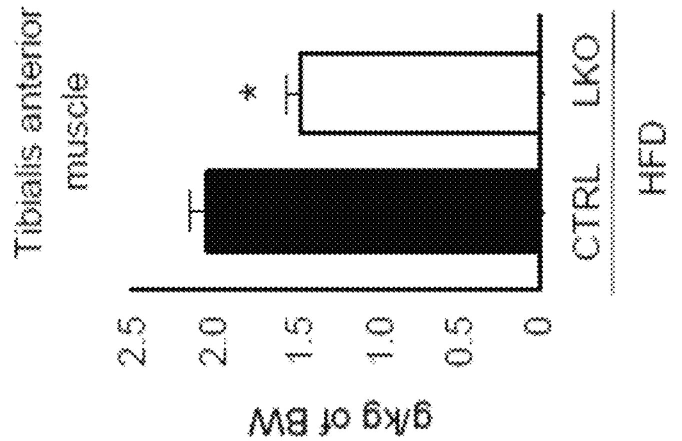
Figure 20A:
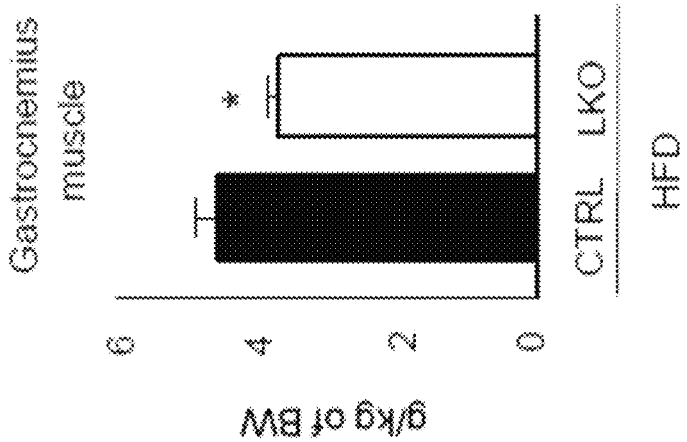
Figure 20D:
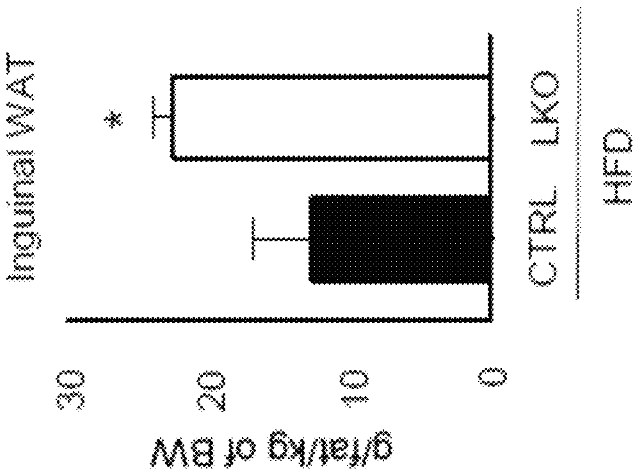
Figure 20C:
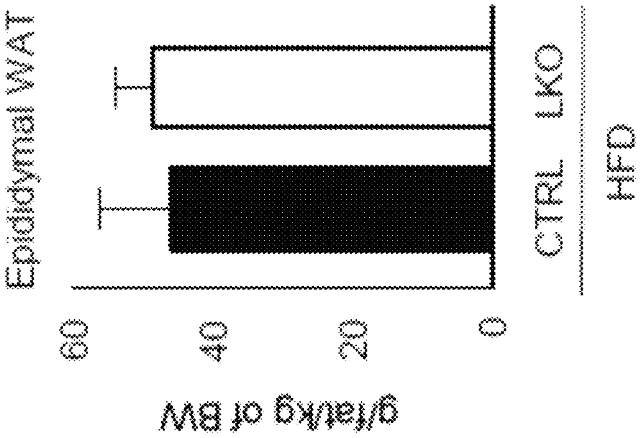

FIG. 19A and FIG. 19B. FIG. 19A shows the heat expenditure assessed by CLAMS, reflecting lower metabolism in HFD LKO mice. FIG. 17B shows serum levels of the liver enzyme alanine aminotransferase (ALT), a marker for liver disease, in CTRL and LKO mice.

FIG. 20A through FIG. 20D show the weight of gastrocnemius muscle (FIG. 20A), tibialis anterior muscle (FIG. 20B), epididymal white adipose tissue (eWAT) (FIG. 20C), and inguinal white adipose tissue (iWAT) (FIG. 20D) in CTRL and LKO mice. Mean ± SEM shown, Student's unpaired t-test, *p<0.05 compared to controls.

Figure 21B:
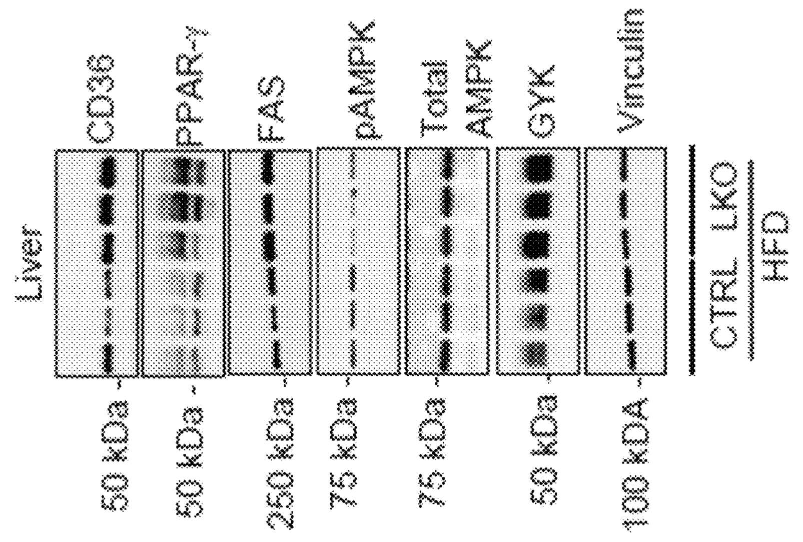
Figure 21A:
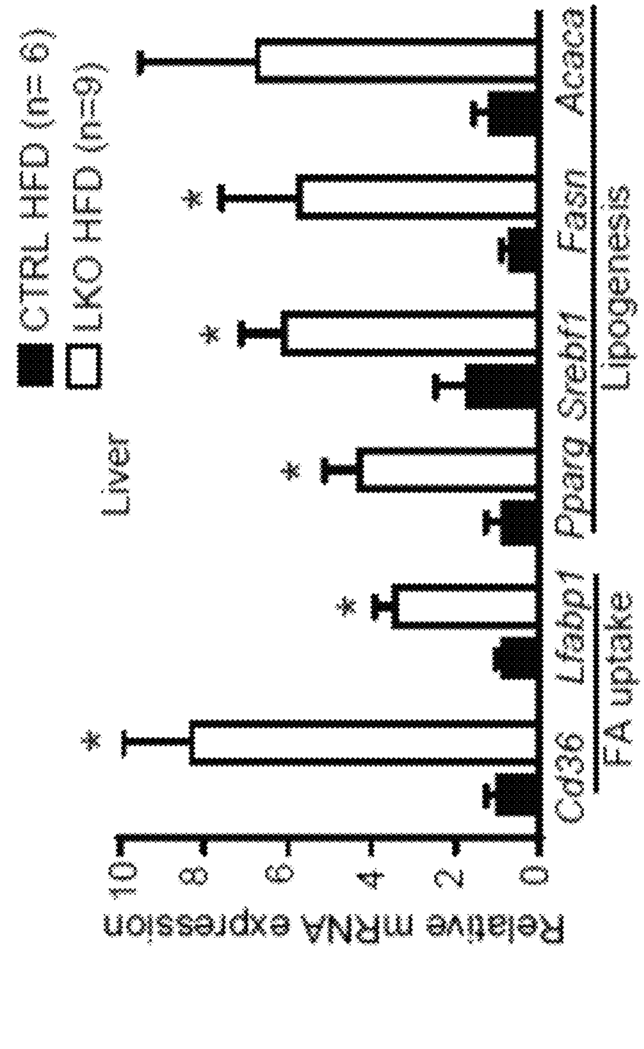

FIG. 21A and FIG. 21B. FIG. 21A shows the relative mRNA expression of indicated genes in liver samples (HFD) normalized to Rp/13a mRNA expression. FIG, 21B provides representative western blots showing the expression of the indicated proteins in liver samples. Mean ± SEM shown; Student's unpaired t-test, *p<0.05 compared to control group.

Figure 10:
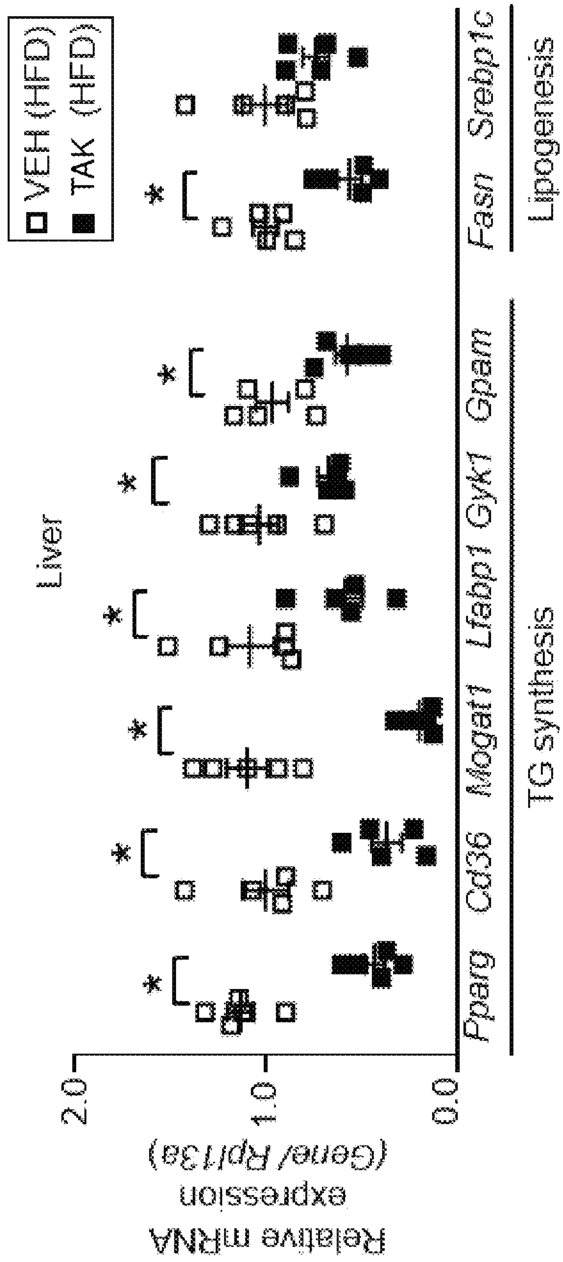
FIG. 10 is a graph relating to the inhibitory effects of TAK-448 treatment on expression of key regulators of hepatic triglyceride synthesis and de novo lipogenesis.
Figure 22A:
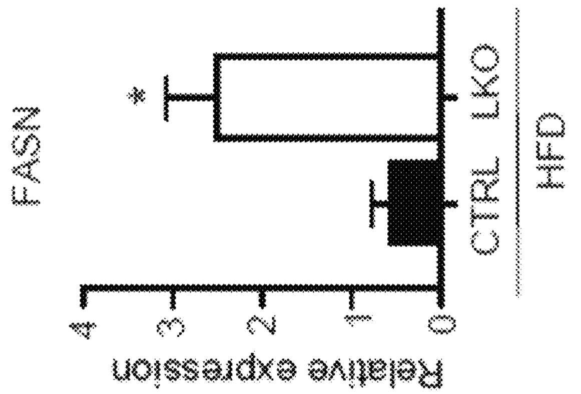
Figure 22B:
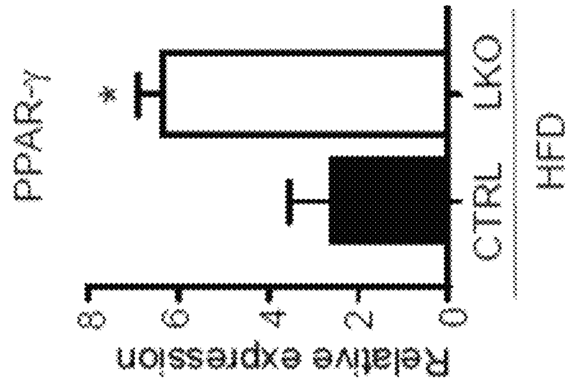
Figure 22C:
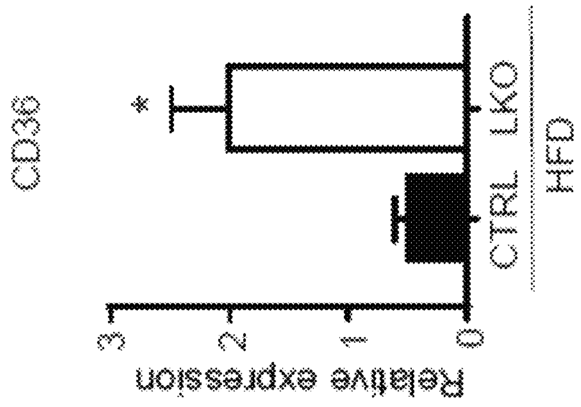

FIG. 22A through FIG. 22D show densitometric analysis of the expression of the indicated proteins from the western blots in FIG. 21B: FIG. 22A (FASN); FIG. 22B (PPARy); FIG. 22C (CD36); FIG. 10D (pAMPK/total AMPK)

Figure 23A:
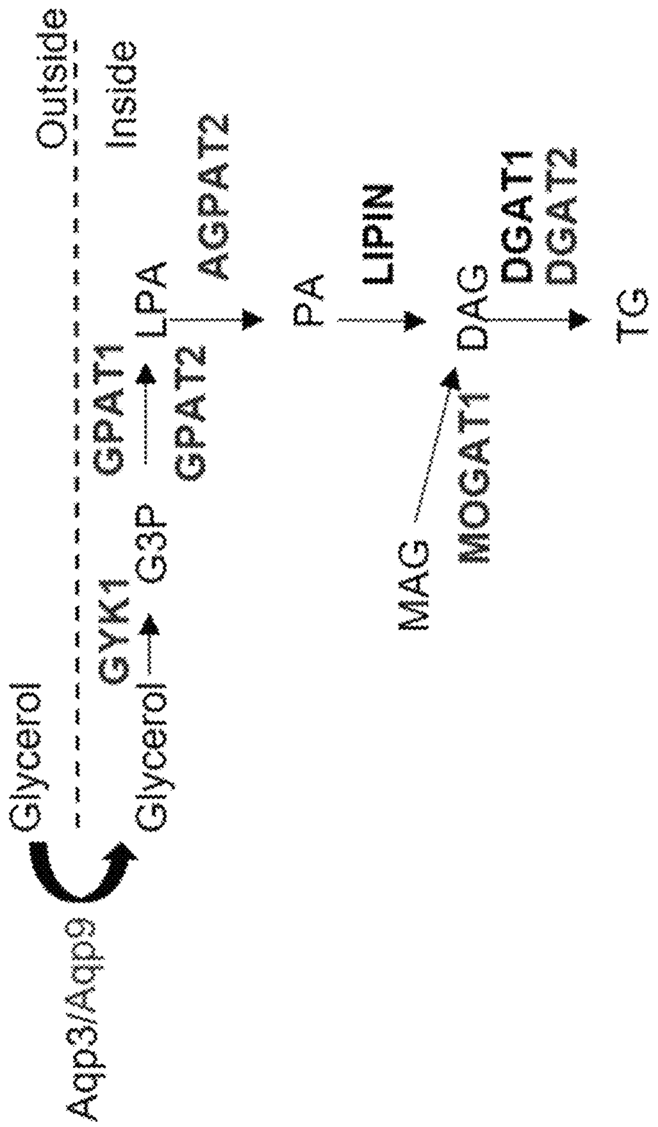
Figure 22D:
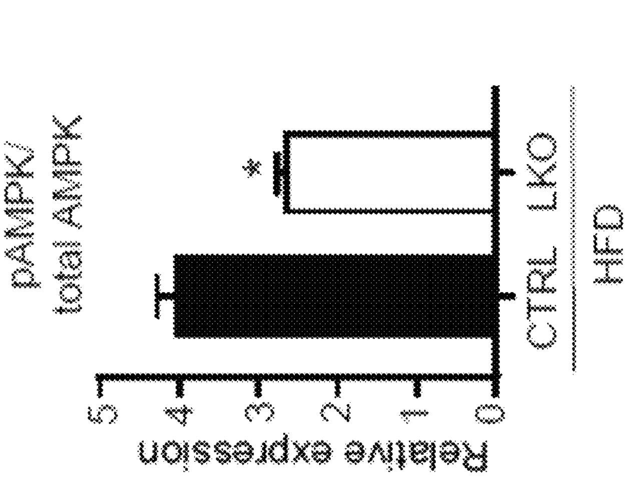
Figure 23B:
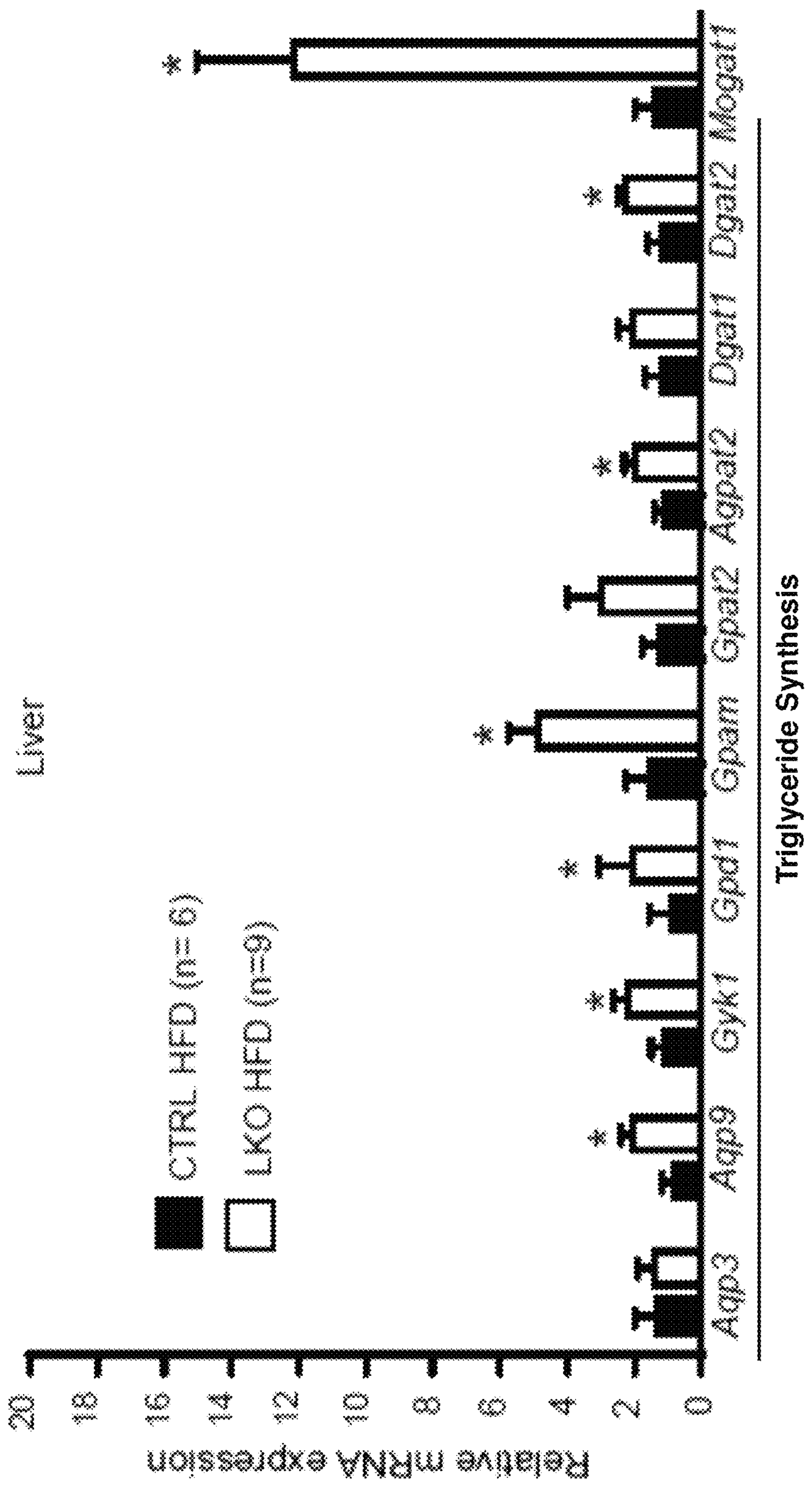

FIG. 23A and FIG. 23B. FIG. 23A is a schematic drawing showing the hepatic triglyceride (TG) synthesis pathway; molecules in red are upregulated in HFD LKO compared to control (CTRL) livers. FIG. 23B shows the relative mRNA expression of indicated genes by RT- gPCR in LKO liver samples normalized to Rpl13a mRNA expression.

Figure 24:
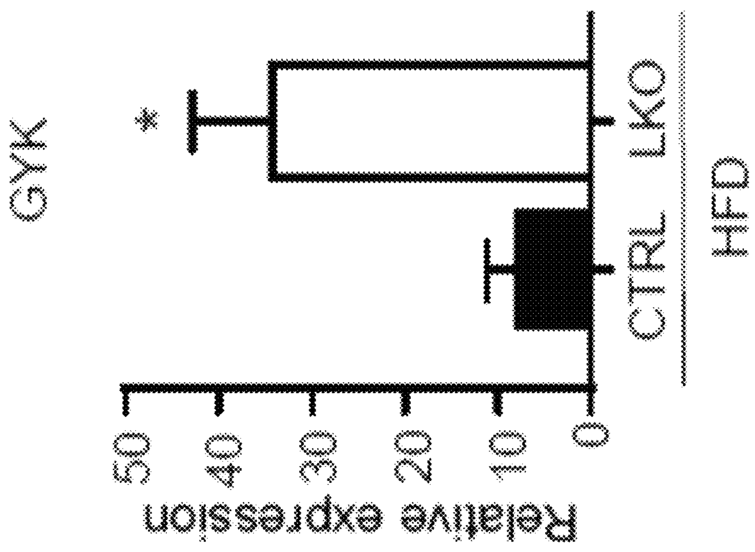

FIG. 24 shows densitometric analysis of GYK expression from the western blots in FIG. 22B.

Figure 25A:
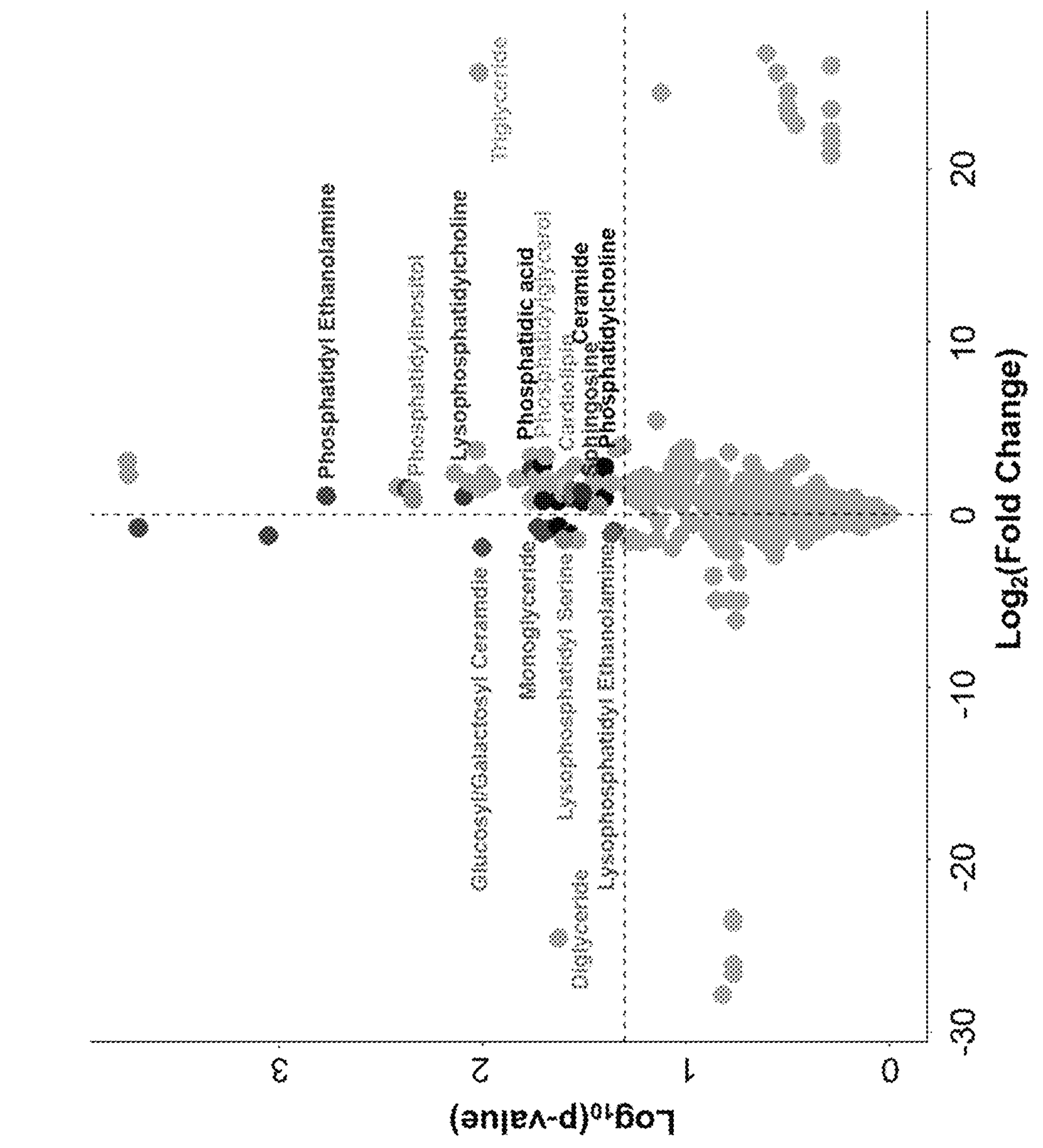
Figure 25B:
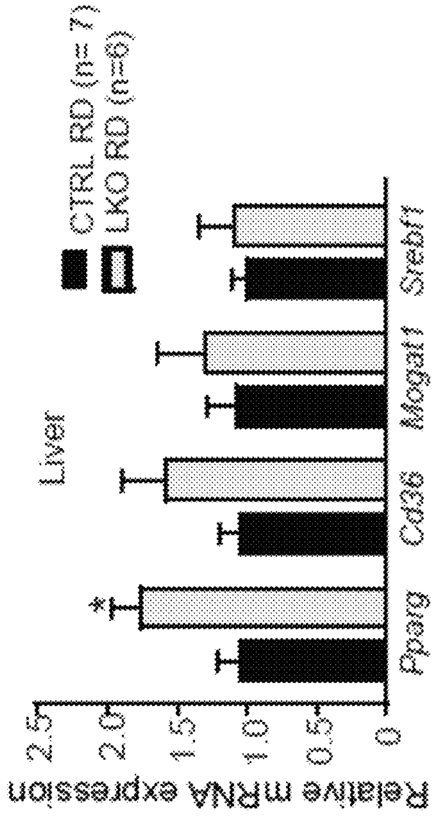

FIG. 25A and FIG. 25B. FIG. 25A is a volcano plot comparing liver lipids measured by LC-MS in CTRL and LKO mice on HFD. FIG. 25B shows the relative mRNA expression of the indicated genes by RT-qPCR in livers of CTRL and LKO mice maintained on RD, normalized to Rpl13a mRNA expression. Mean ± SEM shown, Student's unpaired t-test, *p<0.05 compared to controls.

Figure 26A:
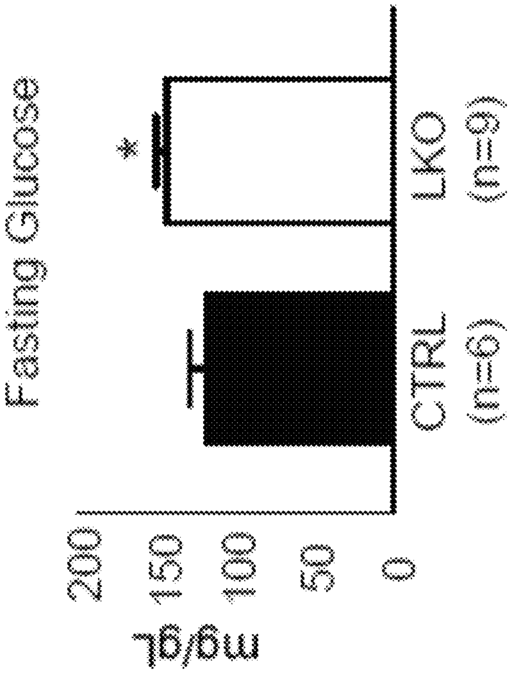
Figure 26C:
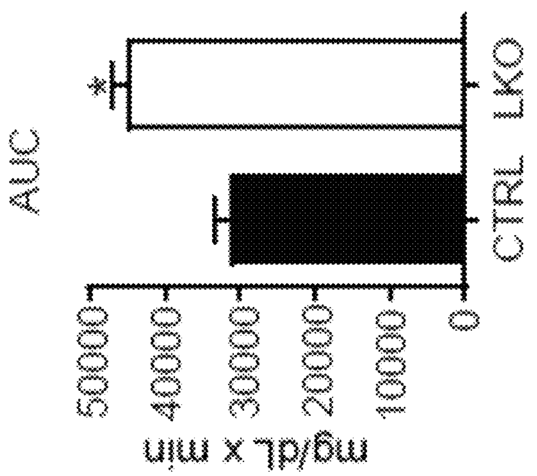
Figure 26B:
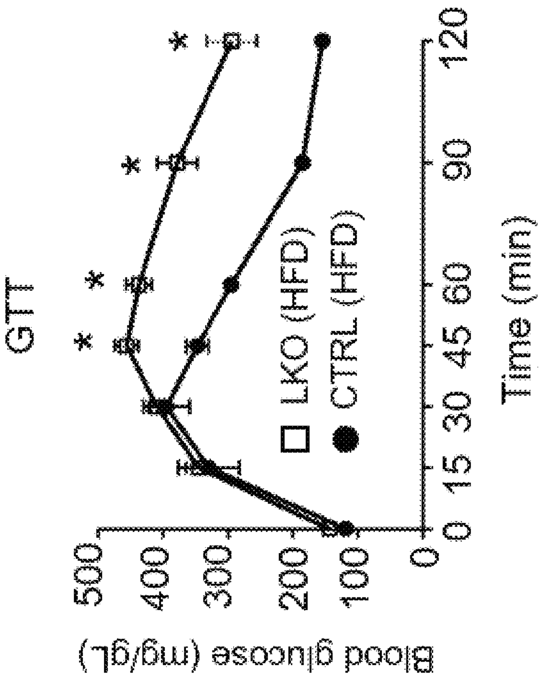
Figure 26D:
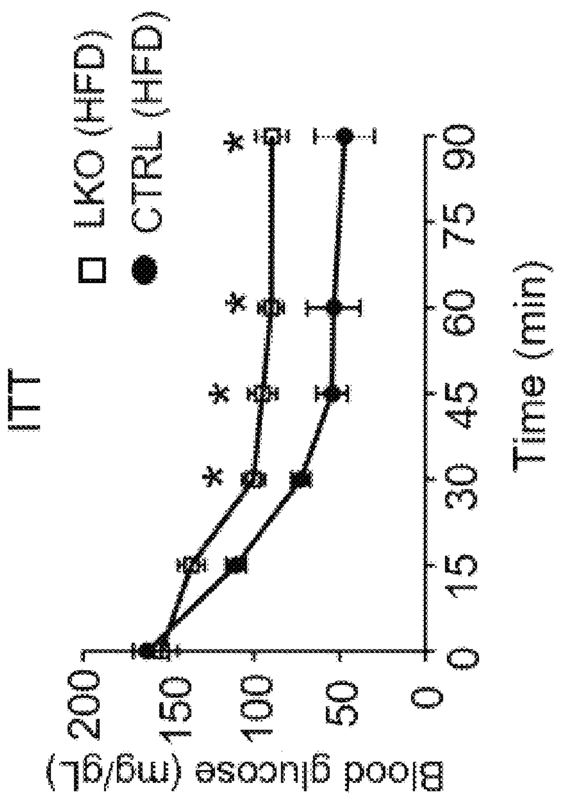
Figure 26E:
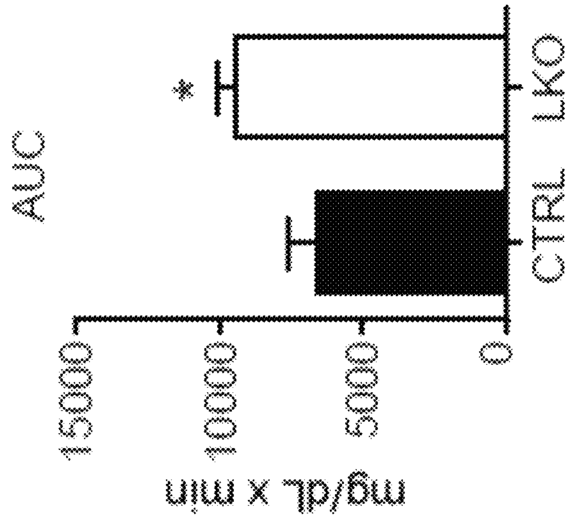
Figure 26G:
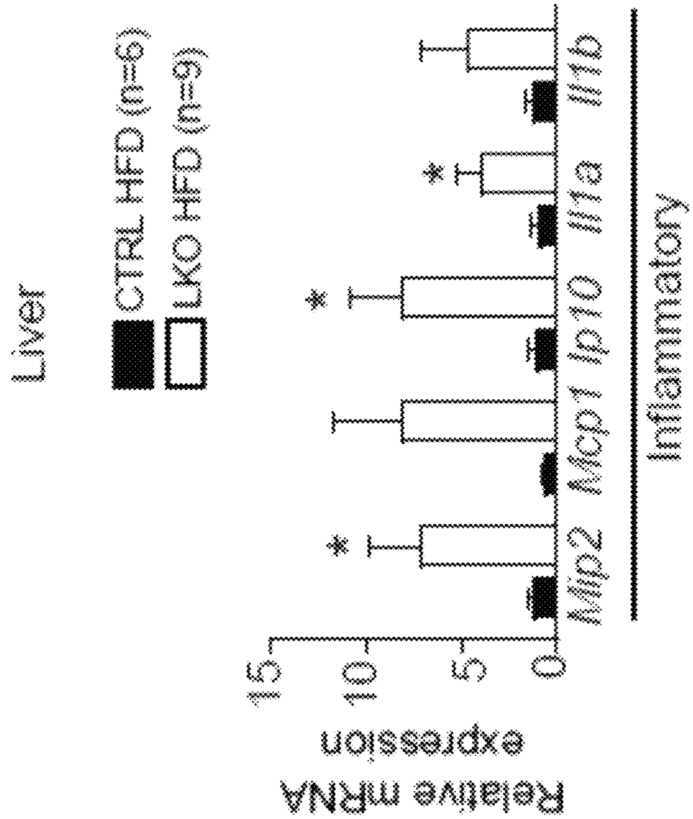
Figure 26F:
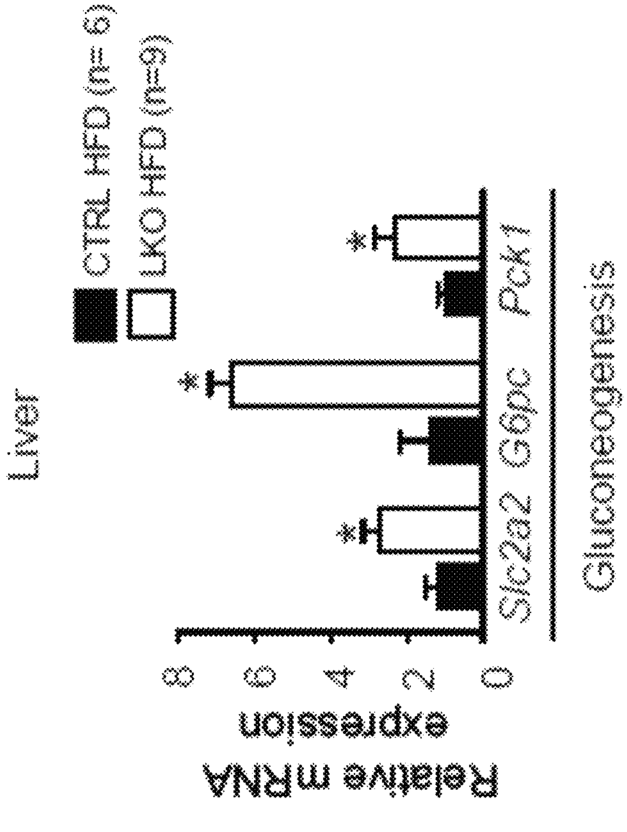
Figure 26H:
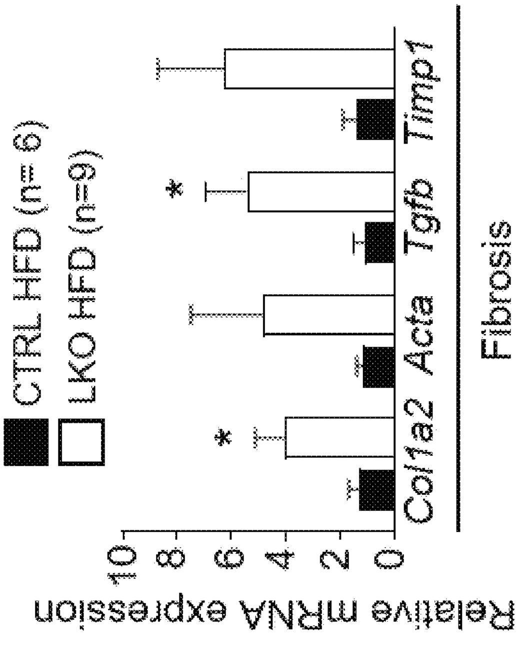
Figure 26I:
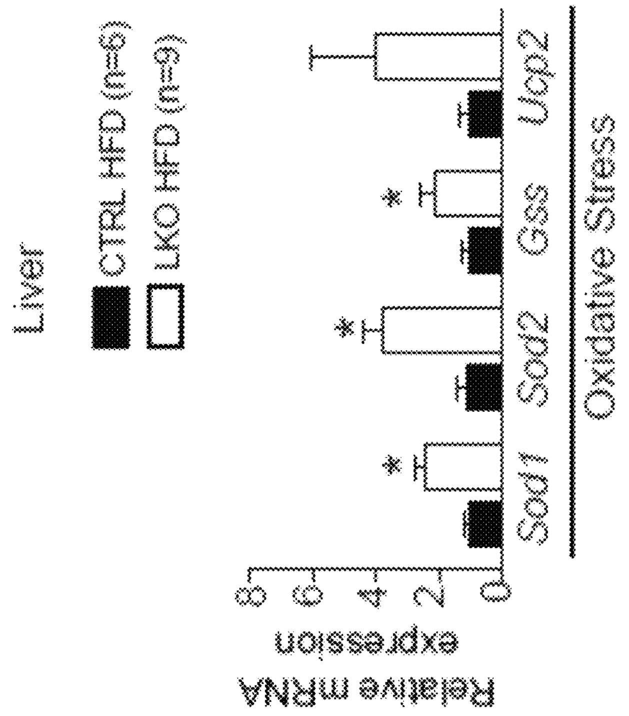

FIG. 26A through FIG. 26I. FIG. 26A and FIG. 26B show the fasting blood glucose levels (FIG. 26A) and blood glucose levels (FIG. 26B) during a GTT in CTRL and LKO mice on HFD after a 12-hour fast. FIG. 26C shows the area under the curve (AUC) of GTT. FIG. 26D shows the blood glucose levels in CTRL and LKO mice on HFD after 6 h fast during an ITT. FIG. 26E shows the AUC of ITT, Relative mRNA expression of indicated genes by RT-qPCR in CTRL and LKO (HFD) liver samples showing genes regulating glucose metabolism (FIG. 26F) and markers for inflammation (FIG. 26G) and fibrosis (FIG. 26H), and mitochondrial oxidative stress (FIG. 26I) normalized to Rpl13a mRNA expression. Mean ± SEM shown, Student's unpaired t-test. *p<0.05 compared to controls.

Figure 27:
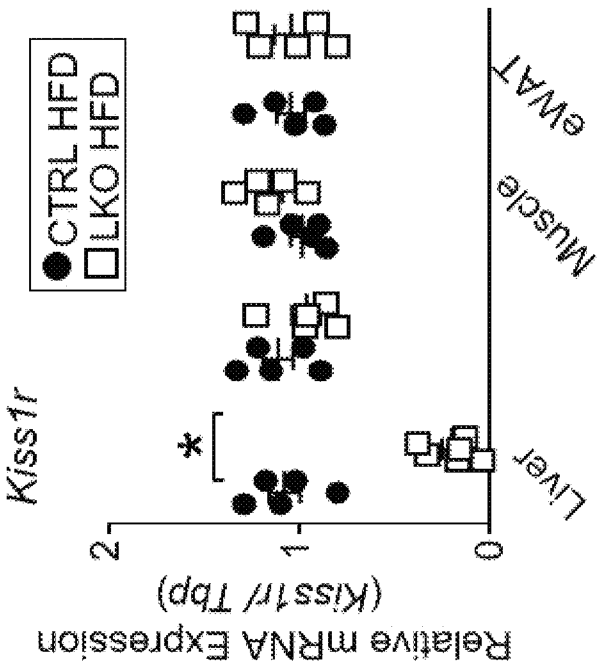

FIG. 27 is a graph showing the relative mRNA expression of KISS IR.

Figure 28A:
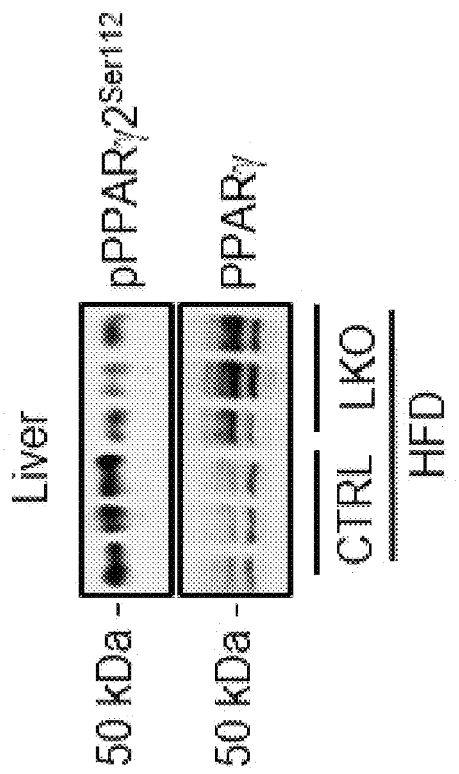
Figure 28B:
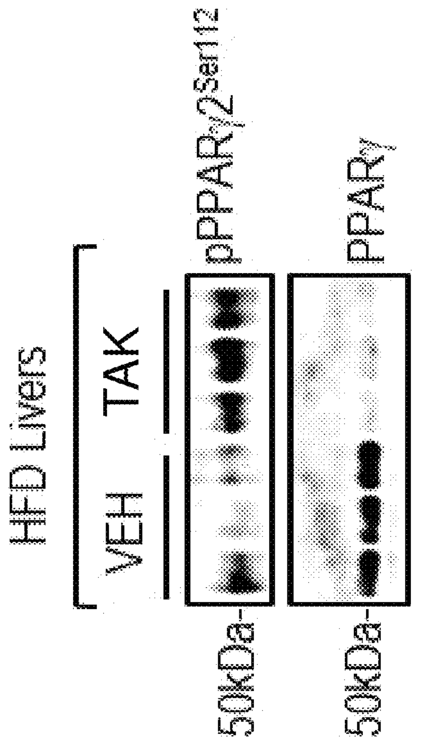

FIG. 28A and FIG. 28B. FIG. 28A shows the relative mRNA expression of indicated genes by RT-qPCR in HFD liver samples, normalized to Rpl13a mRNA expression. FIG. 28B is a representative western blot showing expression of indicated protein in HFD livers mice.

Figure 29C:
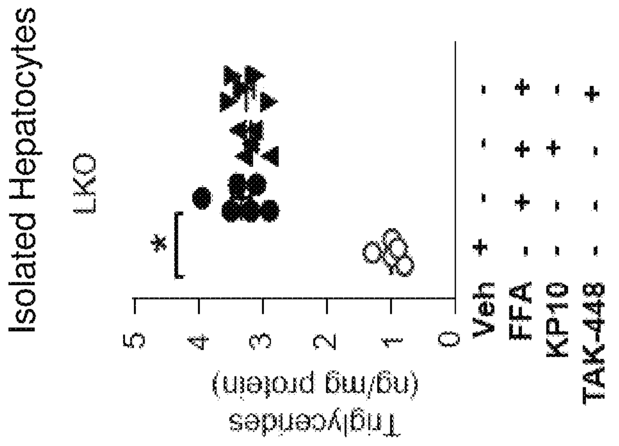
Figure 29B:
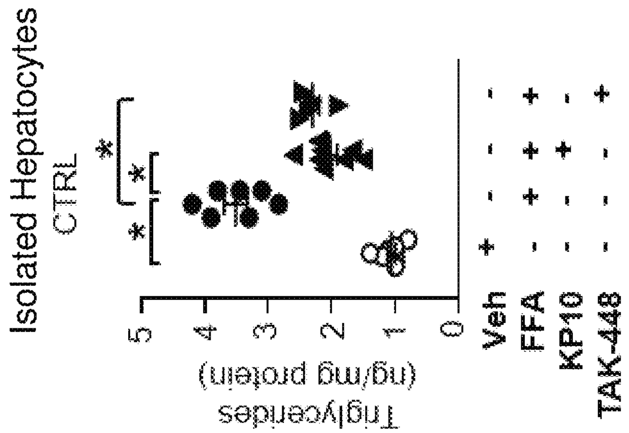
Figure 29A:
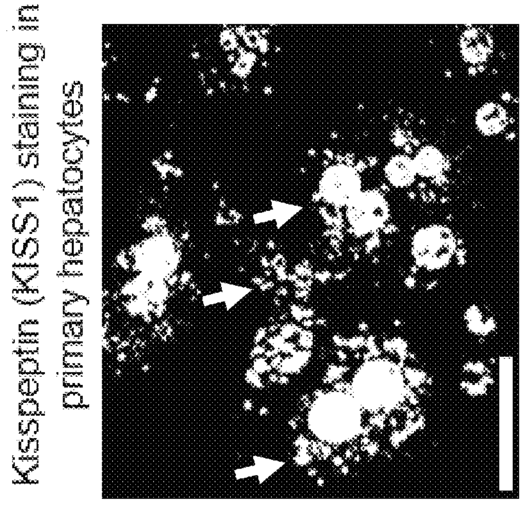

FIG. 29A is confocal image of endogenous kisspeptin immunostaining (See arrows) in isolated primary hepatocytes. FIG. 29B is a graph showing the inhibitory effects of TAK-448(3 nM), or kisspeptin-10 (100 nM), on FFA (150 μM oleic acid and 150 μM palmitic acid) loaded triglyceride accumulation in primary mouse hepatocytes. FIG. 29C is a graph showing the lack of effects of TAK-448 or kisspeptin-10 on FFA (150 μM oleic acid and 150 μM palmitic acid) loaded triglyceride accumulation in hepatocytes isolated from LKO mice (lacking KISS 1R). * p<0.05; One-way ANOVA followed by Dunnett's post-hoc test.

Figure 30:
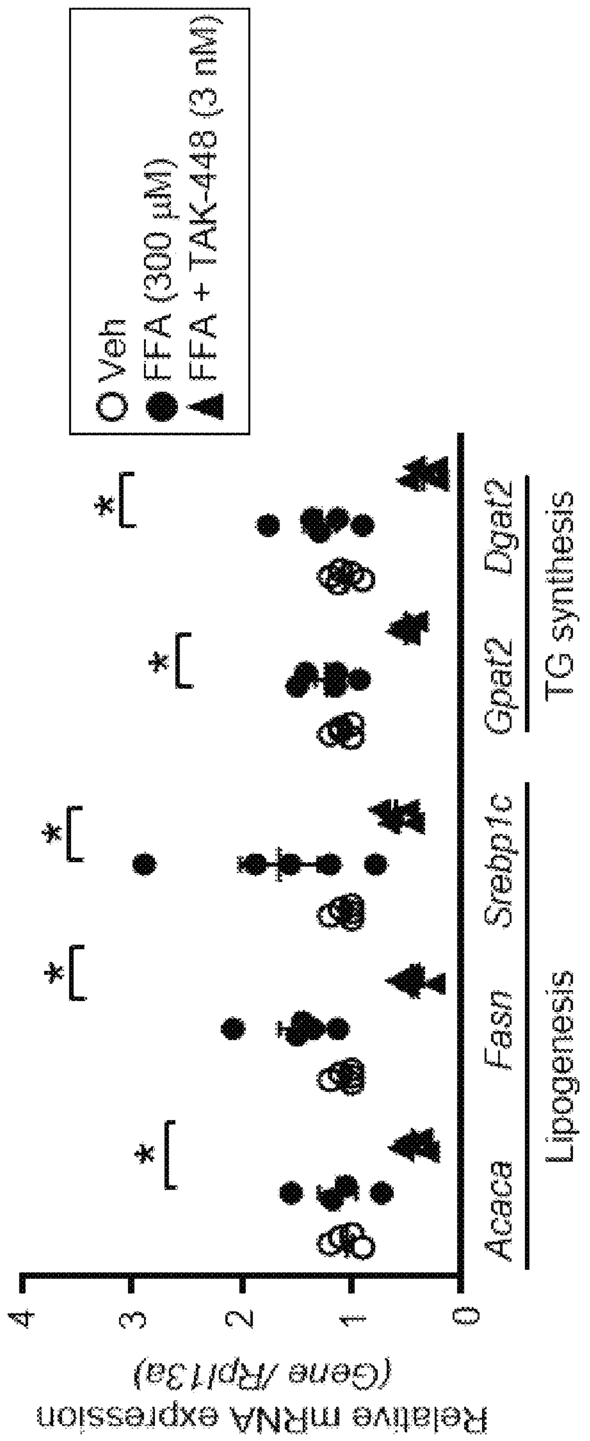

FIG. 30 is a graph showing the inhibitory effect of TAK-448 treatment on expression of genes regulating de novo lipogenesis and triglyceride synthesis.

Figure 31A:
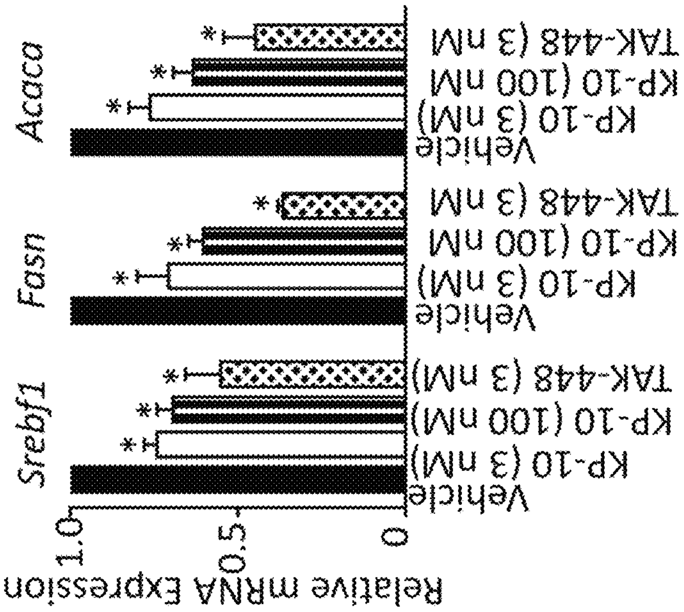
Figure 31B:
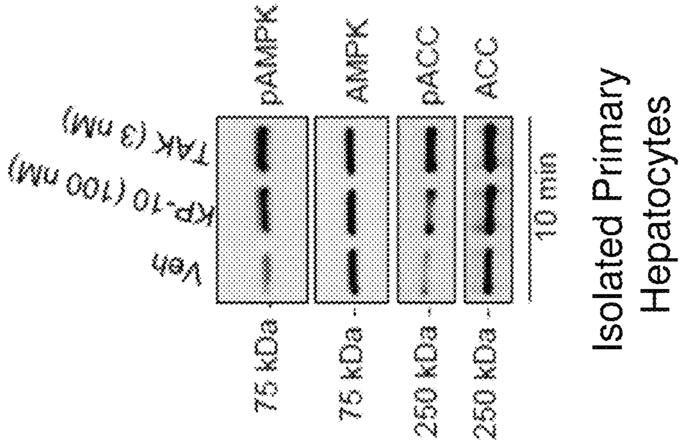
Figure 31C:
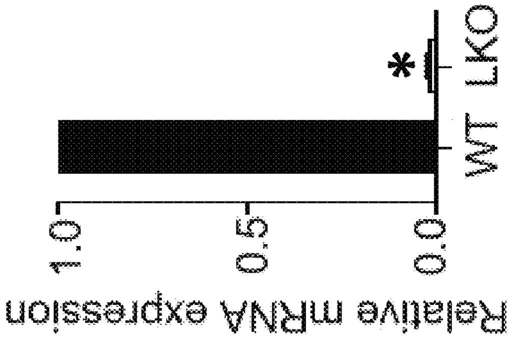

FIG. 31A through FIG. 31C. FIG. 31A shows the relative mRNA expression of indicated genes by RT-qPCR in primary mouse hepatocytes isolated from C57BL6 male mice upon kisspeptin (KP) or TAK treatment for 8h, under basal conditions. (n=5) * p<0.05; One-way ANOVA followed by Dunnett's post-hoc test. FIG. 31B shows representative western blots showing the effect of kisspeptin treatment on phosphorylation of AMPK (resulting in its activation) to thereby inhibit its downstream substrate ACC, in primary mouse hepatocytes (n=4). FIG. 31C shows Kiss1R expression in primary mouse hepatocytes from CTRL and LKO mice by RT-qPCR in normalized to Rpl13a mRNA expression (n=4). KISS 1R expression is depleted in isolated hepatocytes from LKO micelivers.

Figure 32B:
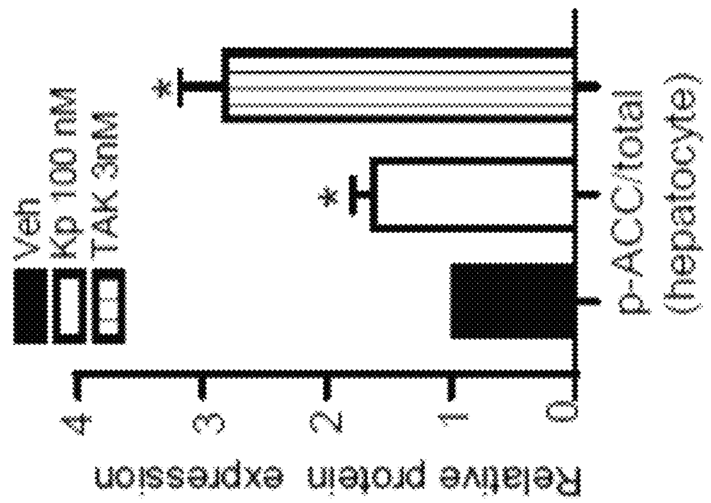
Figure 32A:
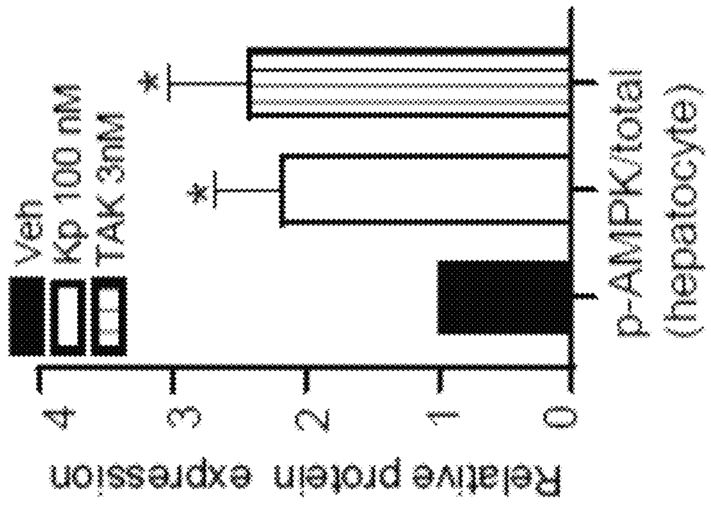

FIG. 32A and FIG. 32B provide densitometric analysis of the western blots of FIG. 23C.

Figure 33B:
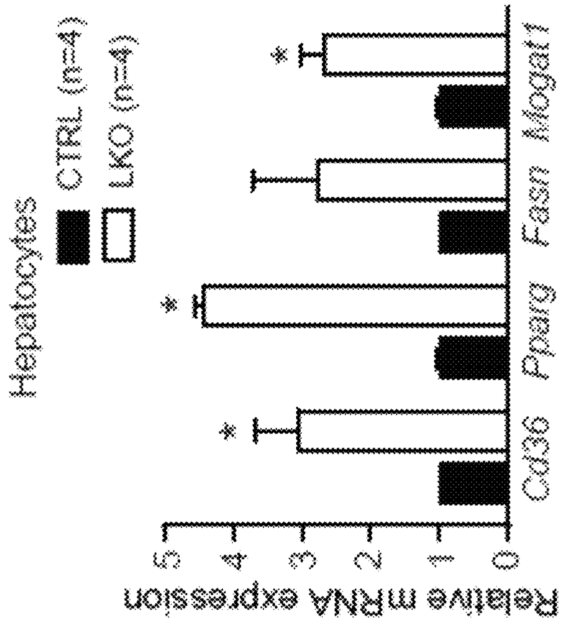
Figure 33A:
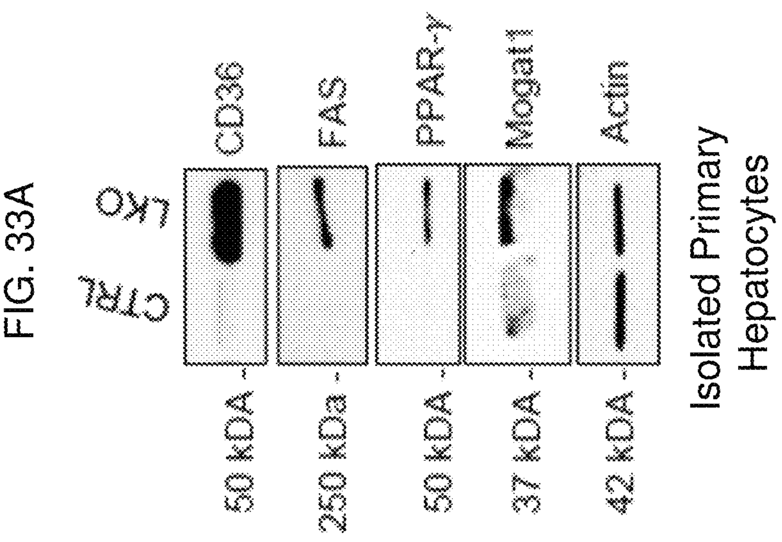

FIG. 33A and FIG. 33B. FIG. 33A provides representative western blots showing expression of the indicated proteins. FIG. 33B shows relative mRNA expression of the indicated genes by RT-qPCR in primary mouse hepatocytes isolated from CTRL and LKO mice (n=4). Mean ± SEM shown, Student's unpaired t-test, *p<0.05.

Figure 34B:
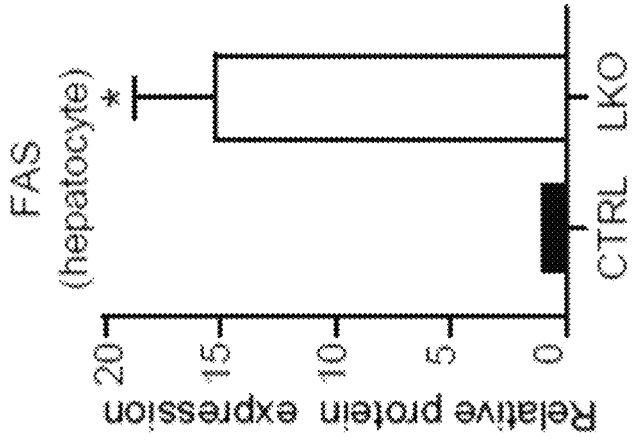
Figure 34A:
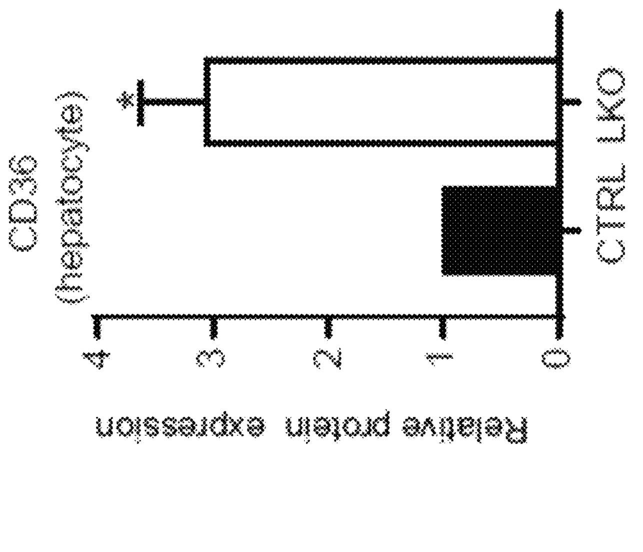
Figure 34D:
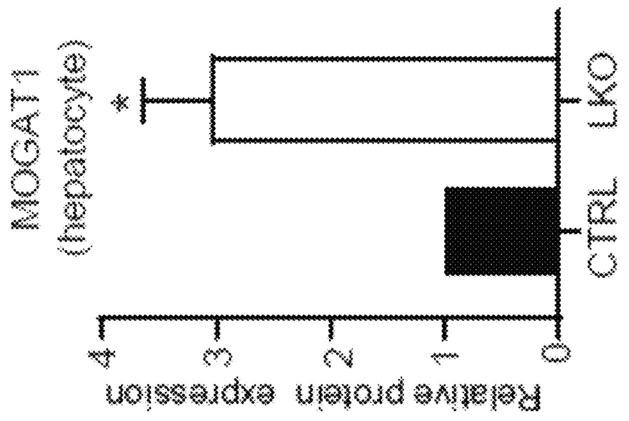
Figure 34C:
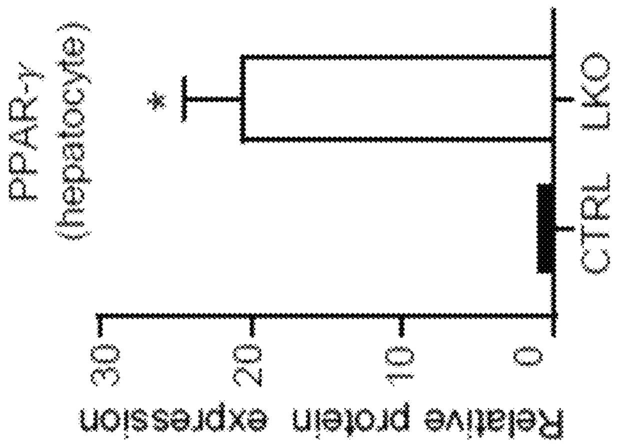

FIG. 34A through FIG. 34D provide densitometric analysis of the western blots of FIG. 33A for CD36 (FIG. 34A), FAS (FIG. 34B), PPARγ (FIG. 34C), and MOGAT1 (FIG. 34D). Mean + SEM shown, Student's unpaired t-test. *p<0.05 compared to controls.

Figure 35B:
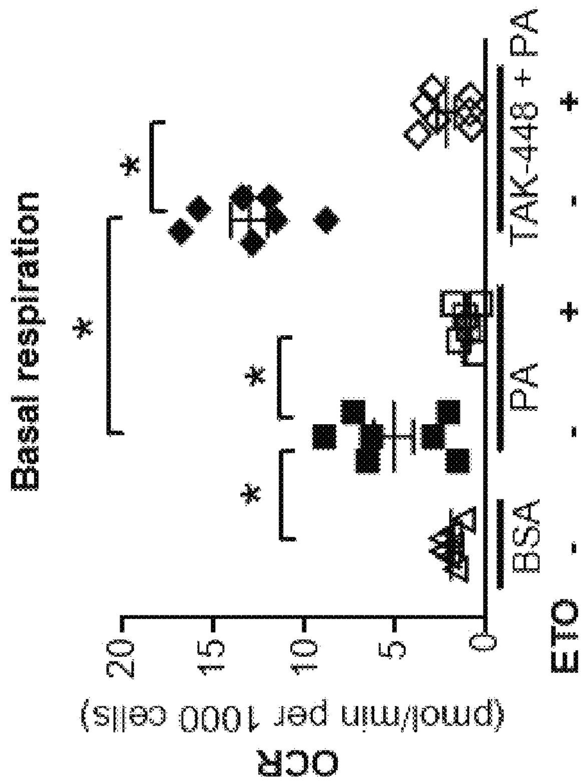
Figure 35A:
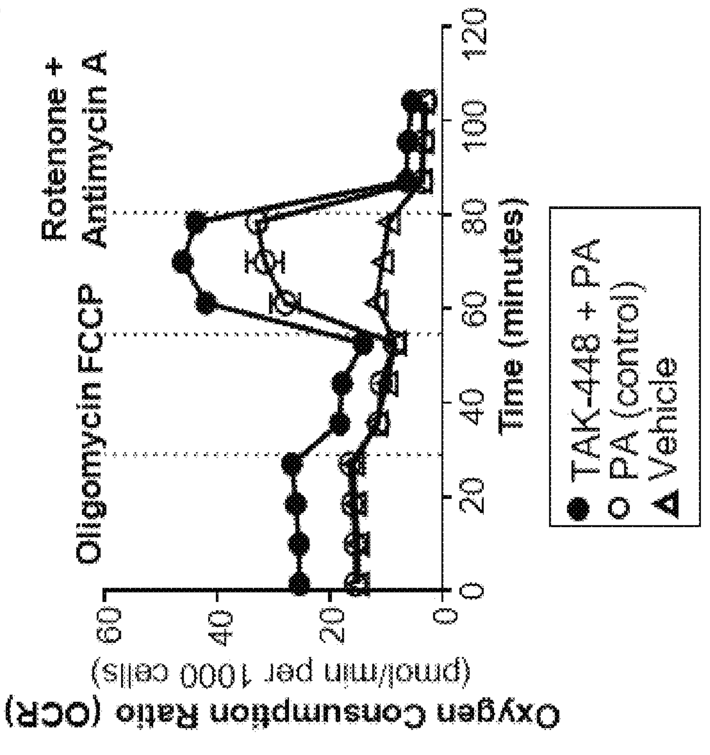
Figure 35C:
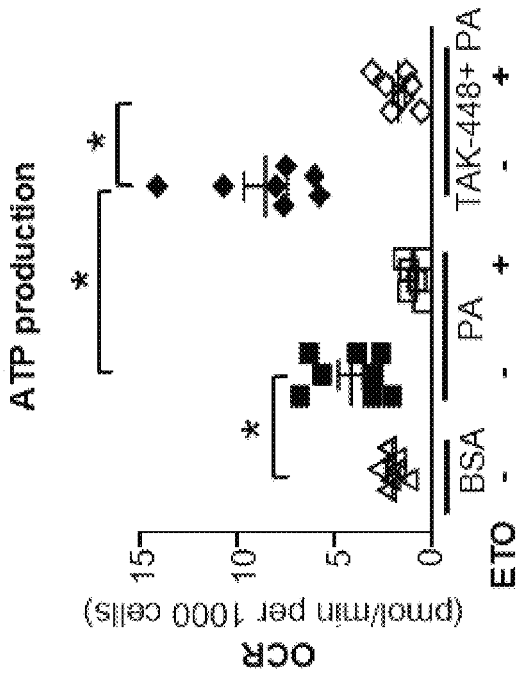

FIG. 35A through FIG. 35B is a set of graphs showing TAK-448 treatment in free fatty acid (FFA: palmitate, 100 μM)-loaded mouse primary hepatocytes increases oxygen consumption rate leading to enhanced fatty acid oxidation (FIG. 35A). TAK-448 treatment also increased basal respiration (FIG. 35B), and ATP production (FIG. 35C).

Figure 36A:
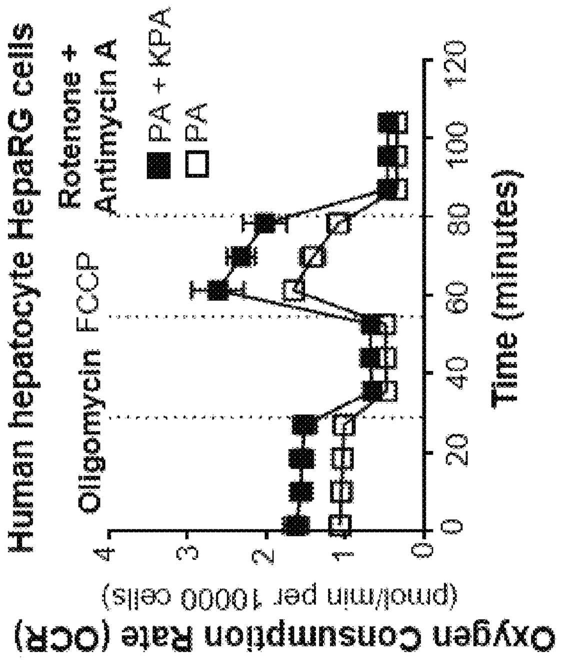
Figure 36C:
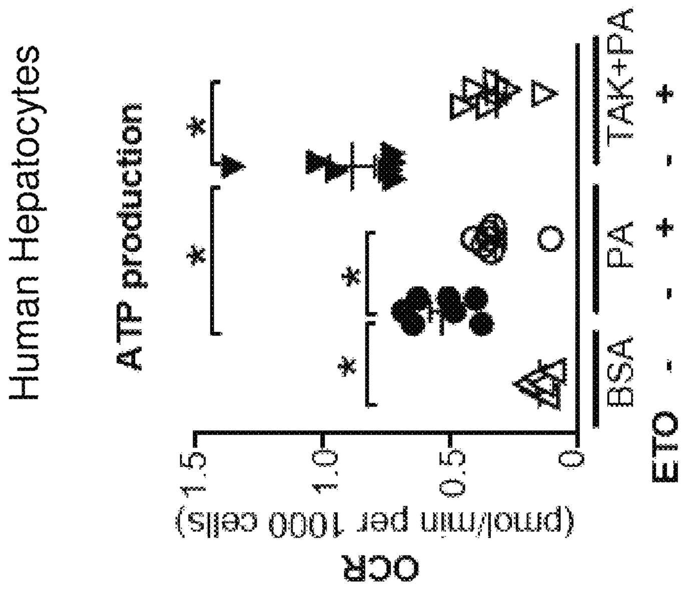
Figure 36B:
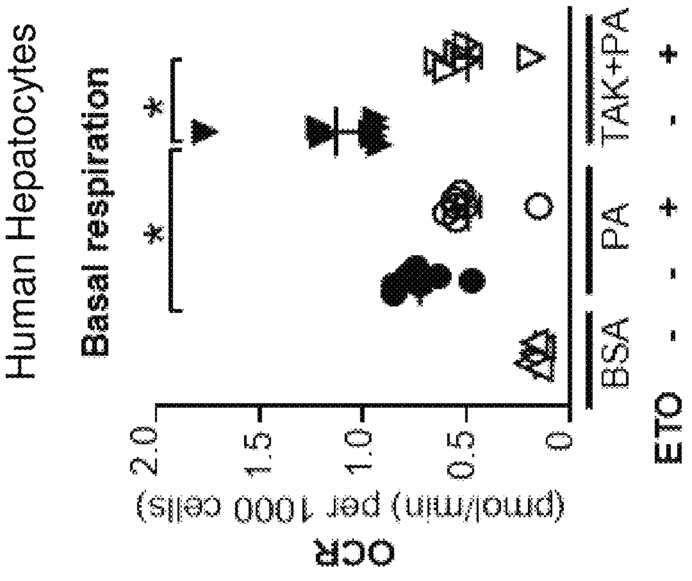

FIG. 36A through FIG. 36C are graphs showing TAK-448 treatment in FFA (palmitate, 100 μM)-loaded human hepatocytes increases oxygen consumption rate over time following treatment. TAK-448 treatment also increased basal respiration (shown in FIG. 36B) and ATP production shown in (FIG. 36C).

Figure 37A:
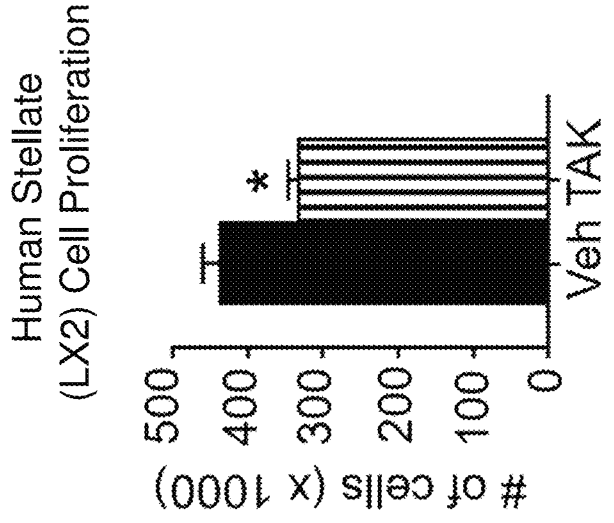
Figure 37B:
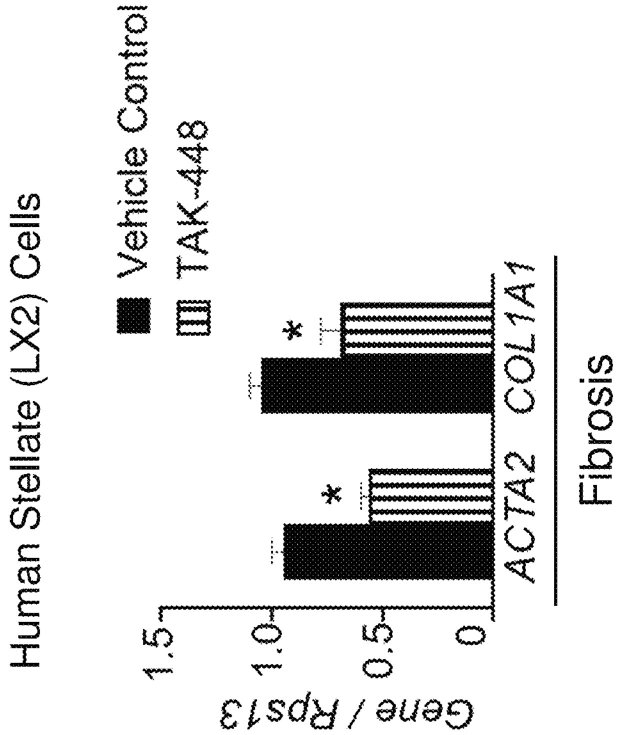

FIG. 37A and FIG. 37B are sets of bar graphs showing that TAK-448 treatment decreases proliferation of human stellate LX2 cells, as observed by a decrease in cell count (FIG. 37A). TAK-448 treatment decreases fibrosis marker gene expression (FIG. 37B) in LX2 cells.

Figures 38A, 38B, 38C, 38D:
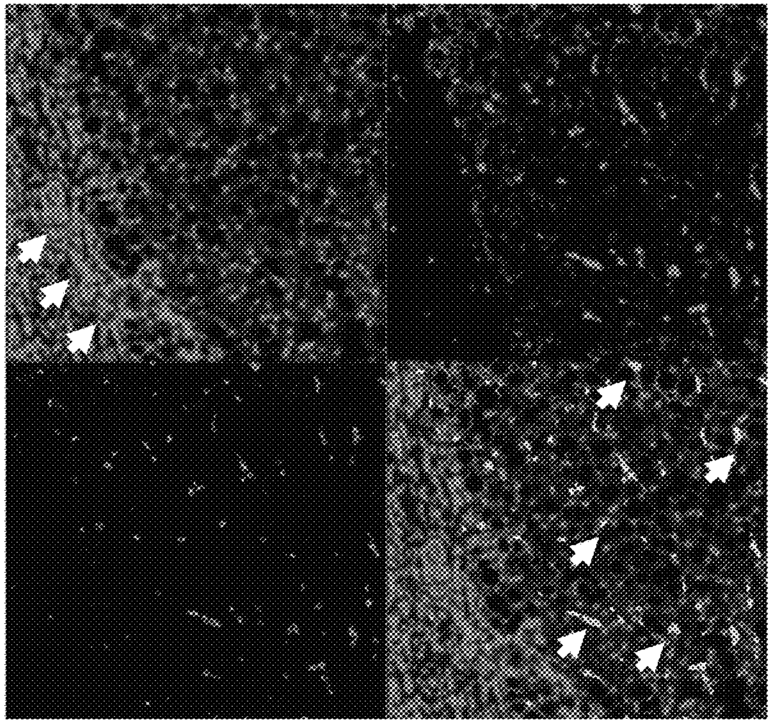

FIG. 38A through FIG. 38D are a set of immunofluorescence images showing staining of human liver biopsy from NAFLD patient as indicated for nuclei (FIG. 38A), endogenous KISS1R (FIG. 38B), stellate cells (FIG. 38C), and an overlay (FIG. 38D).

Figure 39B:
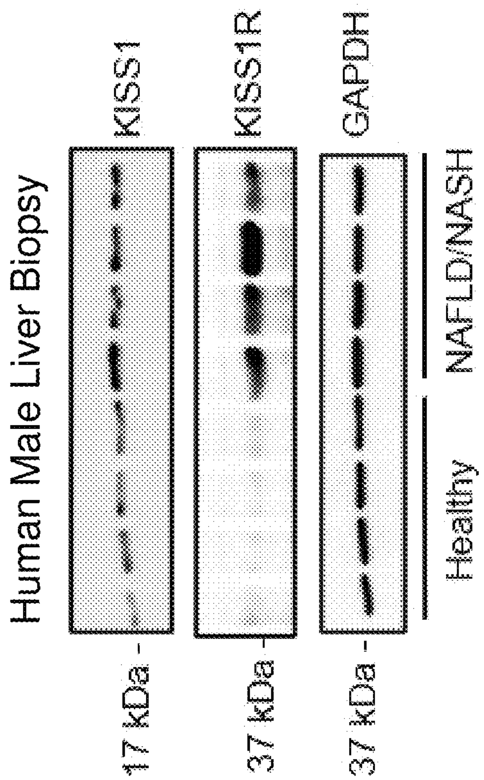
Figure 39A:
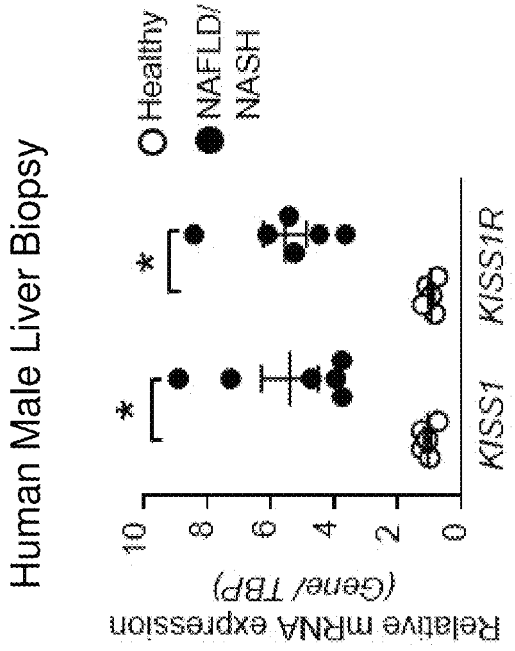
Figure 39C:
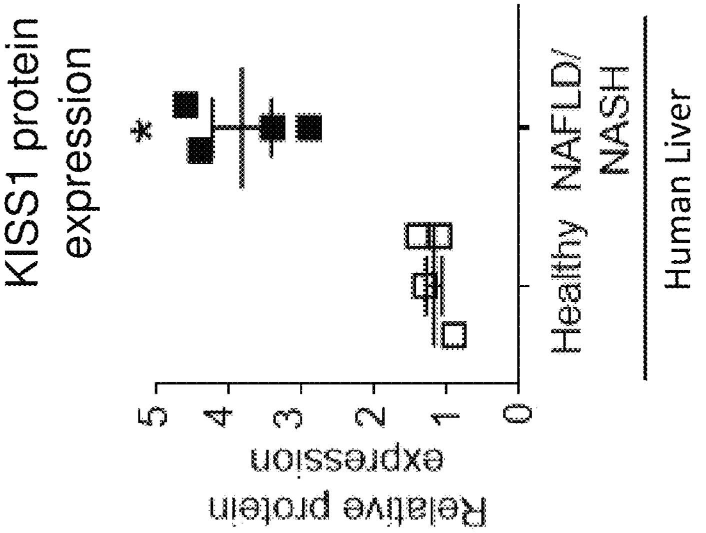
Figure 39D:
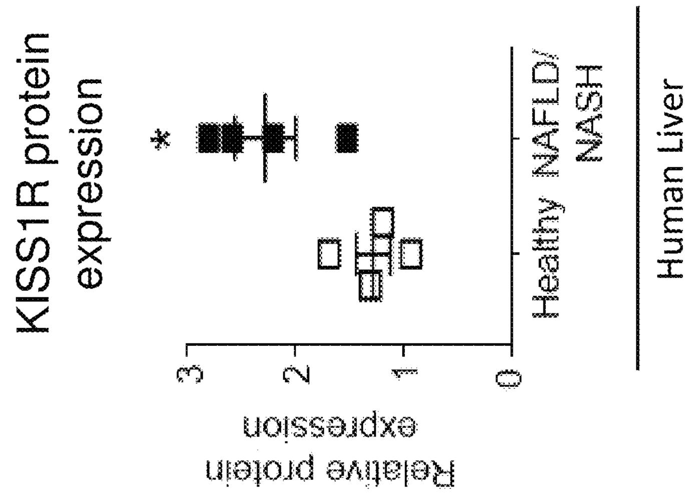
Figure 39E:
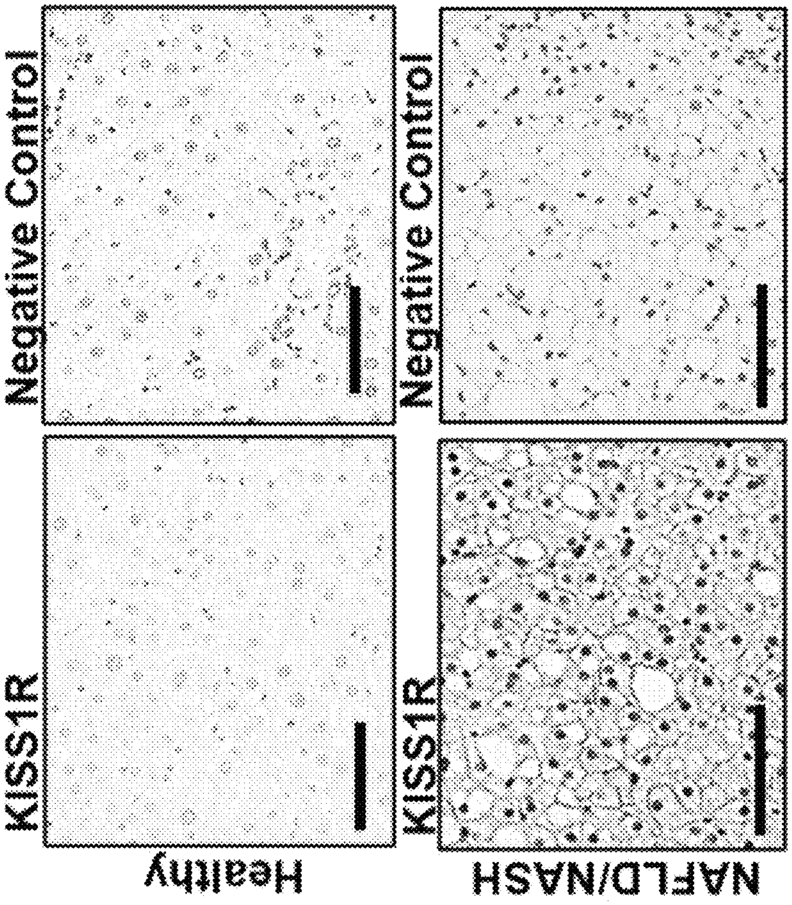

FIG. 39A is a graph showing relative mRNA expression in patient liver biopsies. The gene and protein expression of KISS1 and KISS1R is elevated in patient liver biopsies from NAFLD/NASH patients compared to healthy control livers. FIG. 39B is a set of western blots. FIG. 39C and FIG, 39D show densitometric analysis of the blots in FIG. 39B. FIG. 39E is a set of representative histology images showing higher KISS1R stainiang in adult liver from NAFLD/NASH patients compared to healthy subjects.

Figure 39F:
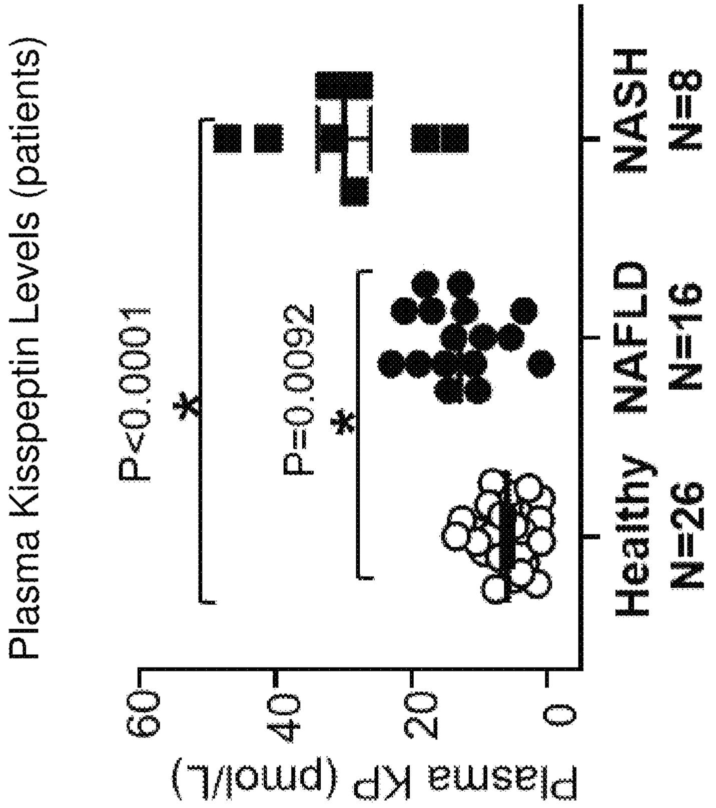

FIG. 39F is a bar graph showing plasma kisspeptin levels by radioimmunoassay in human subjects; plasma kisspeptin levels are significantly elevated in the NAFLD/NASH patients compared to healthy subjects, suggesting that the increase in kisspeptin maybe a compensatory, protective mechanism aiming to resolve NAFLD.

Figure 40:
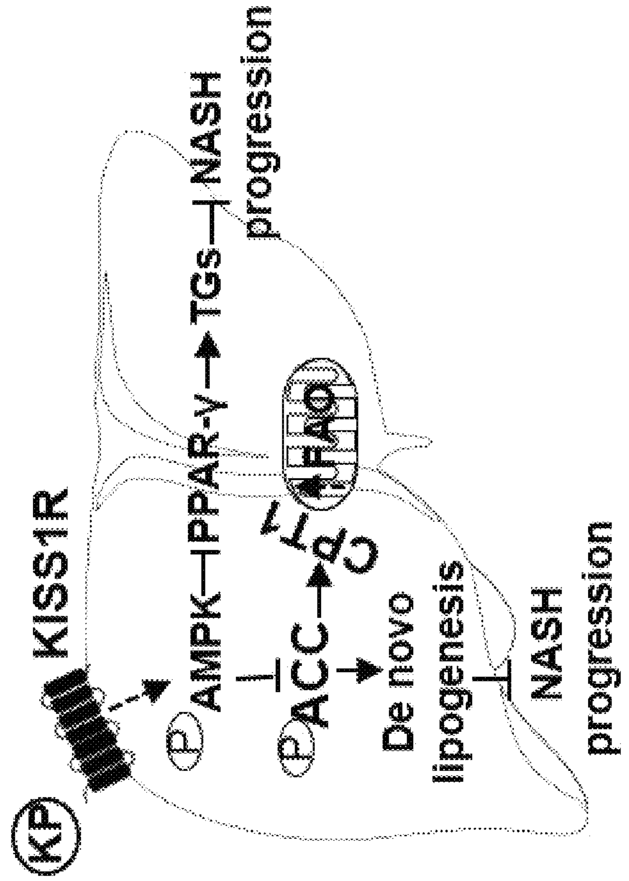

FIG. 40 is a schematic drawing showing a proposed signaling pathway (shown in blue) by which KP/KISS1R activation inhibits hepatic lipogenesis.

DETAILED DESCRIPTION

1. Definitions

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

The term "about," as used herein, means plus or minus 20 percent of the recited value, so that, for example, "about 0.125" means 0.125±0.025, and "about 1.0" means 1.0±0.2.

The term "TAK-448" as used herein, refers to a stable analog of the fully active 10-amino acid C terminus of kisspeptin-54 (kisspeptin-10); these are peptide products of kispeptin-145, encoded by the KISS1 gene. Kisspeptin-54 was formerly known as metastin and is a ligand for the G-protein coupled kisspeptine1 receptor (KISS1R), previously known as GPR54.

The term "treat," and its cognates such as "treatment," as used herein, refers to obtaining a desired pharmacologic and/or physiologic effect. Thus, "treatment" includes (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example, causing regression or partial regression of the condition or disease or symptom thereof.

The term "prevent," and its cognates such as "prevention," as used herein, refers to reducing the likelihood of occurrence of a disease or condition, reducing the severity of a disease or condition, and partially or totally stopping the disease or condition in a subject.

The term "subject," as used herein, refers to a mammal, preferably a human patient, including human children patients.

The term "in need thereof," as used herein, refers to a subject suffering from or suspected of suffering from non-alcoholic fatty liver disease (NAFLD) and non-alcoholic steatohepatitis.

The term "therapeutically effective amount," as used herein, refers to an amount, dosage, or dosage regimen that produces a therapeutic effect, preferably a desired pharmacologic and/or physiologic result.

The term "administer," and its cognates, such as "administration," refers to contact of a compound with a subject according to methods and routes known in the art of pharmaceutical science.

The term "fatty liver" refers to the condition where the liver of a subject contains 5% or more fat. Conditions falling within the category of "fatty liver" include, but are not limited to, fatty liver disease, hepatitis, non-alcoholic fatty liver disease, non-alcoholic steatohepatitis, alcoholic steatohepatitis, liver fibrosis, cirrhosis of the liver, jaundice and liver cancer, or any condition where the liver contains 5% or more fat.

The term "NAFLD/NASH," as used herein, refers to non-alcoholic fatty liver disease and/or non-alcoholic steatohepatitis. NAFLD encompasses a spectrum of pathological conditions, including steatosis (fatty liver), nonalcoholic steatohepatitis (NASH), fibrosis and cirrhosis (excessive scarring of liver).

The term "conservative variant" with respect to a natural or synthetic peptide or peptide analog, refers to a sequence that is about 90% or more identical to the peptide, for example with one amino acid substituted, added, or deleted in the sequence. This term also includes chemical variants of the peptide, such as a chemical modification of the amino acid side chains, including addition of a methyl, ethyl, halo, tri-fluoro, hydroxyl, carboxylate, amino, methylamino, and the like to the structure of the compound.

2. Overview

The present invention will provide a therapy for metabolic disorders such as NAFLD and NASH through the administration of TAK-488, a long-lasting synthetic analog of kisspeptin-10, a naturally occurring peptide found in the blood. Kisspeptin signals via the kisspeptin receptor (KISS1R), a G protein-coupled receptor and both kisspeptin and KISS1R are expressed by the liver. Kisspeptin-54 peptide has been administered to healthy men which has been shown to enhance insulin secretion, without altering food intake or appetite.

3. Embodiments of the Invention

This report provides the first evidence of a novel function of KISS1R as a key regulator of hepatic lipogenesis. Although KISS1R is expressed in the liver, its biological function in the liver remained unknown. The goal of the present study was to determine the role of KISS1R in the development and progression of fatty liver, such as NAFLD, and to provide compositions and methods for use in prevention and treatment of NAFLD/NASH and other conditions involving accumulation of fat in the liver. Using a hepatic Kiss1r knockout (LKO), we found that hepatic Kiss1r deficiency exacerbated hepatic steatosis, inflammation and fibrosis in a mouse model of NAFLD. HFD LKO mice showed aggravated metabolic parameters such as increased body weight, elevated levels of liver TGs, elevated fasting glucose and insulin resistance and an increase in inflammatory and fibrosis markers.

These phenotypes suggest that hepatic KISS1/KISS1R ablation plays a crucial role in negatively regulating the development of the NAFLD phenotype and related metabolic deterioration. Thus, to test the hypothesis that hepatic KISS1R plays a protective role in NAFLD, insulin resistant wild-type mice were treated with TAK-448, a protease-resistant KP analog with potent agonist activity comparable to KP10. TAK administration to humans and animals suppresses the neuroendocrine-reproductive axis. We found that in insulin-resistant wild-type mice, TAK treatment suppressed lipid accumulation in livers, reduced serum TGs, cholesterol and FFAs and lowered adipose mass. Additionally, TAK treatment prevented a gain in body weight without changing food intake and improved glucose tolerance and insulin sensitivity. Importantly, TAK administration resulted in a reduction in inflammatory and fibrosis markers. Collectively, these findings demonstrate a critical role of KISS1R in the development of steatosis and NASH.

We also delineated the cellular pathways by which KISS1R regulates lipogenesis (see FIG. 27, blue). Our findings reveal that KISS1R activates AMPK in vivo in HFD livers and in vitro, in isolated primary hepatocytes, leading to an inhibition of de novo lipogenesis (DNL) and TG accumulation underlying the protective effects of KISS/KISS1R on steatosis. DNL (conversion of carbohydrates to fat) is upregulated in NAFLD and activation of AMPK inhibits DNL by phosphorylating ACC and reducing its activity, promoting fatty acid utilization. AMPK activation also leads to the downregulation of lipogenic gene expression by directly phosphorylating the master transcriptional regulator of lipogenesis, SREBP-1.

AMPK activation has been shown to attenuate TG synthesis, resulting in an antisteatotic effect by two possible mechanisms. First, AMPK activation inhibits Liver X receptor α (LXRα) activity in the liver; LXRα is a lipid sensor that promotes fatty acid synthesis and leads to hypertriglyceridemia. Second, AMPK activation inhibits PPARγ transcription. The mechanism by which KP activates AMPK is currently not known. Activation of AMPK requires phosphorylation of threonine 172 (T172) via increases in the AMP:ATP ratio and elevation of intracellular Ca2+(38). Several reports suggest that activation of Ca2+/calmodulin-dependent protein kinase β (CaMKKβ) plays a physiological role in activating AMPK in mammalian cells. Since KISS1R activation increases intracellular Ca2+(41), it is likely that KISS1R activates AMPK via the CaMKKβ pathway.

PPARγ expression is low in healthy livers but rises significantly in NAFLD and contributes to the development of hepatic steatosis by regulating de novo lipid metabolism. Furthermore, PPARγ plays a major role in directly upregulating genes/pathways involved in TG synthesis such as Gyk1, the key enzyme in fatty acid esterification, Cd36, the fat importer, and Mogat1, which esterifies monoacylglycerol to form diacylglycerol (DAG), the precursor of TG. Suppression of PPARγ-dependent MOGAT1 expression inhibits hepatic steatosis, whereas CD36-dependent FFA uptake and MOGAT mediated fatty acid esterification promote steatosis. PPARγ and MOGAT overexpression has also been observed in humans with NAFLD. The finding that TAK inhibited the expression of PPARγ, CD36, and MOGAT1 has significant clinically implications, given the established link between DAG negatively regulating hepatic insulin sensitivity. In conclusion, our study suggests that the hepatic KP/KISS1R signaling system inhibits hepatic de novo lipogenesis in hepatocytes via a mechanism involving AMPK-PPARγ signaling, further suggesting that activation of KISS1R signaling is a promising therapeutic target for the treatment of NAFLD.

Specifically, the pre-clinical studies described here use an established mouse model of NAFLD in which male mice are fed a Western high fat diet (HFD, 60% kcal fat), compared to a regular diet (RD, 4% kcal fat). Using this model, we found that the sub-cutaneous administration of the kisspeptin analog (TAK-448) protected against the development of NAFLD compared to mice treated with Vehicle (PBS) control (see FIG. 1A through FIG. 1J and FIG. 16A and FIG. 16C). Specifically, TAK-448 administered for one month to diabetic mice prevented steatosis (the accumulation of liver triglycerides) and a rise in free fatty acids and glycerol (triglyceride building blocks) in the blood. TAK-448 treatment also protected against peripheral fat accumulation and insulin resistance. See FIG. 1F through FIG. 1J.

In addition, in mice fed HFD bearing a deletion of liver Kiss1R (LKO), a greater increase in body weight (FIG. 2), liver steatosis (FIG. 3) and liver triglycerides (FIG. 4A) were observed compared to littermate controls on HFD, despite no change in food intake (FIG. 2D). This implicates the pathologic role of the kisspeptin/Kiss1R pathway in the pathogenesis of NAFLD. See FIG. 2, FIG. 3 and FIG. 4. Kiss1R knock-out animals also were glucose intolerant and insulin resistant, compared to controls (all on HFD). See FIG. 14B through FIG. 14E. The livers from hepatic KISS1R knock-out mice displayed a significant increase in proinflammatory cytokines (Interleukins (IL)-1α, Mip2, IP10; see FIG. 14G) and biochemical markers for NASH/fibrosis (e.g. TGFbeta, collagen (see FIG. 14H), and, compared to controls (all on HFD).

Kisspeptin also has actions on the brain, regulating the central reproductive system. Chronic administration of kisspeptin results in suppression of sex steroid hormone synthesis. This is mimicked by the long-acting TAK-448 which has been used in men with prostate cancer (two Phase 1 clinical trials) to lower testosterone levels. Additionally, TAK-448 under a different name (MVT-602) is being tested by MYOVANT to treat infertility in women and is currently in Phase 1 and Phase 2 clinical trials.

TAK-448 is an oligopeptide analog of the fully active 10-amino acid C terminus of kisspeptin-54 (kisspeptin-10). It has a half-life of 4 hours in the blood, in contrast to kisspeptins which are rapidly degraded within minutes. TAK-448 is a potent Kisspeptin 1 receptor (KISS1R, or GPR54) agonist. KISS1R is a G protein-coupled receptor that binds kisspeptins. Kisspeptin is encoded by the metastasis suppressor gene KISS1, which is expressed in a variety of endocrine and gonadal tissues. Kisspeptin and KISS1R play key roles in mammalian reproduction due to their involvement in the onset of puberty and control of the hypothalamic-pituitary-gonadal axis. It has been used in trials studying the treatment of prostate cancer, low testosterone, prostatic neoplasms, and hypogonadotropic hypogonadism. The structure of TAK-448 is:

Such conditions include, but are not limited to, (1) NAFLD, (2) NASH, (3) fatty liver disease, (4) hepatitis, (5) liver fibrosis, (6) cirrhosis of the liver, (7) jaundice, (8) liver cancer, or (9) any condition where the liver of a subject contains 5% or more fat.

The term "NAFLD/NASH," as used herein, refers to non-alcoholic fatty liver disease and/or non-alcoholic steatohepatitis. NAFLD encompasses a spectrum of pathological conditions, including steatosis (fatty liver), nonalcoholic steatohepatitis (NASH), fibrosis and cirrhosis (excessive scarring of liver).

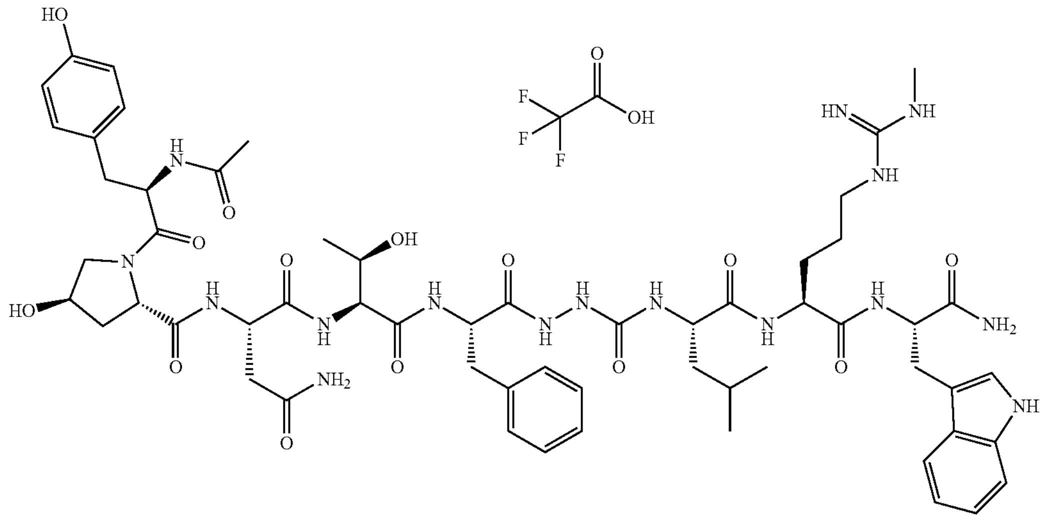

TAK448

See Table 1, below, for sequences of interest.

TABLE 1

Peptide Sequences.

| Name | Sequence | SEQ ID NO |
|---|---|---|
| Mouse Kisspeptin-52 | Ser-Ser-Pro-Cys-Pro-Pro-Val-Glu-Gly-Pro-Ala-Gly-Arg-Gln-Arg-Pro-Leu-Cys-Ala-Ser-Arg-Ser-Arg-Leu-Ile-Pro-Ala-Pro-Arg-Gly-Ala-Val-Leu-Val-Gln-Arg-Glu-Lys-Asp-Leu-Ser-Thr-Tyr-Asn-Trp-Asn-Ser-Phe-Gly-Leu-Arg-Tyr-$NH_2$ | 1 |
| Human Kisspeptin-54 | Gly-Thr-Ser-Leu-Ser-Pro-Pro-Pro-Glu-Ser-Ser-Gly-Ser-Arg-Gln-Gln-Pro-Gly-Leu-Ser-Ala-Pro-His-Ser-Arg-Gln-Ile-Pro-Ala-Pro-Gln-Gly-Ala-Val-Leu-Val-Gln-Arg-Glu-Lys-Asp-Leu-Pro-Asn-Tyr-Asn-Trp-Asn-Ser-Phe-Gly-Leu-Arg-Phe-$NH_2$ | 2 |
| Human Kisspeptin-10 | Tyr-Asn-Trp-Asn-Ser-Phe-Gly-Leu-Arg-Phe-NH2 | 3 |
| TAK-448 | Ac-D-Tyr-D-Trp-Asn-Thr-Phe-azaGly-Leu-Arg(Me)-Trp-$NH_2$ | 4 |

Subjects that can be treated according to embodiments of the invention include any mammal, including laboratory animals, companion animals, farm animals, zoo animals, and the like, including humans. Preferred subjects are humans and rodents. A suitable subject for the invention preferably is a human that is suspected of having, has been diagnosed as having, or is at risk of developing a disease that can be ameliorated, treated or prevented by administration of TAK-448, including any disease or condition involving fatty liver or accumulation of fat in the liver.

TAK-448 can be administered to prevent, delay, slow, reverse, or halt disease progression in any disease or condition involving accumulation of fat in the liver or fatty liver.

The compounds contemplated for use in the invention described herein include, but are not limited to, TAK-448 or any conservative variant thereof, and kisspeptin-10 or any conservative variant thereof. A conservative variant is a peptide of about 90% or more identity of sequence, or a chemically modified peptide as described above. For example, a conservative variant of kisspeptin-10 includes deletions, substitutions, and additions of kisspeptin-10, as well as chemical variants, such as, for example, those exemplified in Tables 2 through Table 6, below. A conservative variant of TAK-448 includes deletions, substitutions, and additions, of TAK-448, as well as chemical variants, such as, for example, those exemplified in Table 2 through Table 6, below.

TABLE 2

Exemplary Compound Variants.

| Compound | Sequence/Structure | SEQ ID NO |
|---|---|---|
| Kisspeptin-10 | Tyr-Asn-Trp-Asn-Ser-Phe-Gly-Leu-Arg-Phe-NH2 | 5 |
| Kisspeptin-10 Variant | Trp-Asn-Trp-Asn-Ser-Phe-Ser-Leu-Arg-Phe-NH2 | 6 |
| Kisspeptin-10 Variant | Tyr-Asn-Trp-Arg-Ser-Phe-Gly-Leu-Arg-Phe-NH2 | 7 |
| Kisspeptin-10 Variant | Tyr-Asn-Trp-Asn-Ser-Phe-Leu-Arg-Phe-NH2 | 8 |
| Kisspeptin-10 Variant | Tyr-Asn-D-Trp-Asn-Ser-Phe-Gly-Leu-Arg (Me)-Phe-NH2 | 9 |
| Kisspeptin-10 Variant | Ac-Tyr-Asn-Trp-Asn-Ser-Phe-Gly-Leu-Arg-Phe-NH2 | 10 |

TABLE 2-continued

Exemplary Compound Variants.

| Compound | Sequence/Structure | SEQ ID NO |
|---|---|---|
| TAK-448 | Ac-D-Tyr-D-Trp-Asn-Thr-Phe-azaGly-Leu-Arg(Me)-Trp-$NH_2$ | 11 |
| TAK-448 Variant | D-Tyr-D-Trp-Asn-Thr-Phe-azaGly-Leu-Arg(Me)-Trp-$NH_2$ | 12 |
| TAK-448 Variant | Ac-D-Tyr-D-Trp-Asn-Thr-Phe-azaGly-Leu-Arg-Trp-$NH_2$ | 13 |
| TAK-448 Variant | Ac-D-Tyr-D-Trp-Asn-Thr-Phe-azaGly-Ala-Arg(Me)-Trp-$NH_2$ | 14 |
| TAK-448 Variant | Ac-D-Tyr-D-Trp-Asn-Ser-Phe-azaGly-Leu-Arg(Me)-Trp-$CH_3$-$NH_2$ | 15 |
| TAK-448 Variant | Ac-D-Tyr-D-Trp-Asn-Thr-Phe-Gly-Leu-Arg(Me)-Trp-$NH_2$ | 16 |
| TAK-448 Variant | Ac-D-Tyr-D-Trp-Asn-Thr-Phe-azaGly-Arg(Me)-Trp-$NH_2$ | 17 |

TABLE 3

Sequences and Binding Affinities of Kisspeptin-10 Analogs

| Peptide Name | Sequence | IC50****, nM | SEQ ID NO |
|---|---|---|---|
| Kisspeptin-10 | YNWNSFGLRF-NH2 | 1.0+/−0.3 | 18 |
| ANA1* | ANWNSFGLRF-NH2 | 23.2+/−14.3 | 19 |
| ANA2* | YAWNSFGLRF-NH2 | 145.1+/−138.0 | 20 |
| ANA3* | YNANSFGLRF-NH2 | 2.7+/−0.7 | 21 |
| ANA4* | YNWASFGLRF-NH2 | 43.5+/−15.5 | 22 |
| ANA5* | YNWNAFGLRF-NH2 | 0.8+/−0.4 | 23 |
| ANA6* | YNWNSAGLRF-NH2 | 109.5+/−89.8 | 24 |
| ANA7* | YNWNSFALRF-NH2 | 4.6+/−1.5 | 25 |

TABLE 3-continued

Sequences and Binding Affinities of Kisspeptin-10 Analogs

| Peptide Name | Sequence | IC50****, nM | SEQ ID NO |
|---|---|---|---|
| ANA8* | YNWNSFGARF-NH2 | 77.4+/−10.0 | 26 |
| ANA9* | YNWNSFGLAF-NH2 | 42.3+/−6.7 | 27 |
| ANA10* | YNWNSFGLRA-NH2 | — | 28 |
| ANA11* | FNWNSFGLRF-NH2 | 3.5+/−2.1 | 29 |
| ANA12* | YDWNSFGLRF-NH2 | 29.1+/−13.5 | 30 |
| ANA13* | YNWDSFGLRF-NH2 | 140.2+/−60.6 | 31 |
| ANA14* | YNWNTFGLRF-NH2 | 2.3+/−1.6 | 32 |
| ANA15* | YNWNSYGLRF-NH2 | 87.5+/−30.7 | 33 |
| ANA16* | YNWNSFGIRF-NH2 | 39.9+/−8.1 | 34 |
| ANA17* | YNWNSFGLKF-NH2 | 9.8+/−2.6 | 35 |
| ANA18* | YNWNSFGLRH-NH2 | 378.4+/−266.0 | 36 |
| ANA19* | [dY]NWNSFGLRF-NH2 | 3.6+/−0.3 | 37 |
| ANA20* | YNWNS[dF]GLRF-NH2 | 252.9+/−144.0 | 38 |
| ANA21* | YNWNSFGLR[dF]-NH2 | 447.2+/−173.0 | 39 |
| TAK-683 | Ac-dYdWNTFazaGLR(Me)W-$NH_2$ | — | 40 |
| Compound 2** | Ac-YNWNSFGLRY-$NH_2$ | — | 41 |
| Compound 3** | Ac-YK(Palm-γ-D)WGΨ[Tz]L RY-$NH_2$ | — | 42 |
| Compound 4** | Ac-YNK(Palm-γ-D)NSFGΨ[Tz]LRY-$NH_2$ | — | 43 |
| Compound 5** | Palm-γ-DYNWNSFGΨ[Tz]LRY-$NH_2$ | — | 44 |
| Compound 6** | Palm-γ-DYNWNSFGΨ[Tz]LR[Me]Y-$NH_2$ | — | 45 |
| Compound 7** | Ac-YNWNSFGΨ[Tz]LR[Me]Y-$NH_2$ | — | 46 |

*Information from Curtis et al., 2009;
**Information from Decourt et al., 2016;
****$IC_{50}$ (means +/− SE; n = 3 − 5) against [$^{125}$I]KP-54 binding to KISS1R in CHO-KISS1R membrane preparations.
Each receptor binding assay was carried out in triplicate.

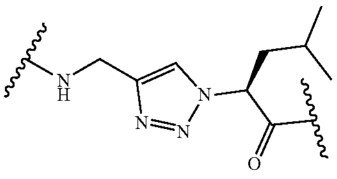

GlyΨ[Tz]Leu

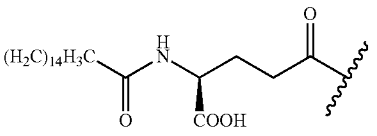

Palm-γ-Glu

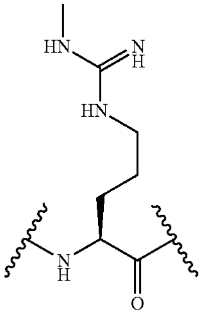

Arg(Me)

Compound 6

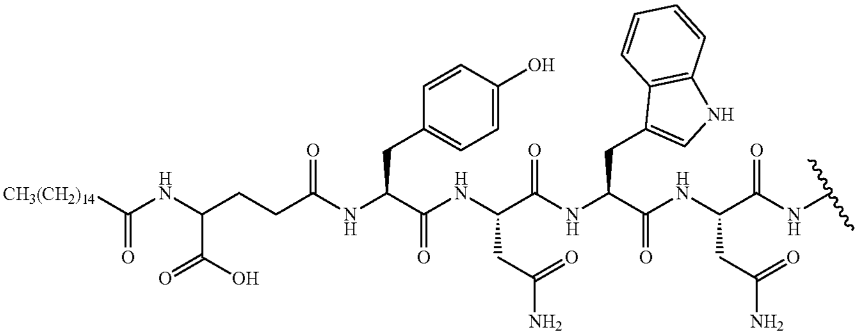

-continued

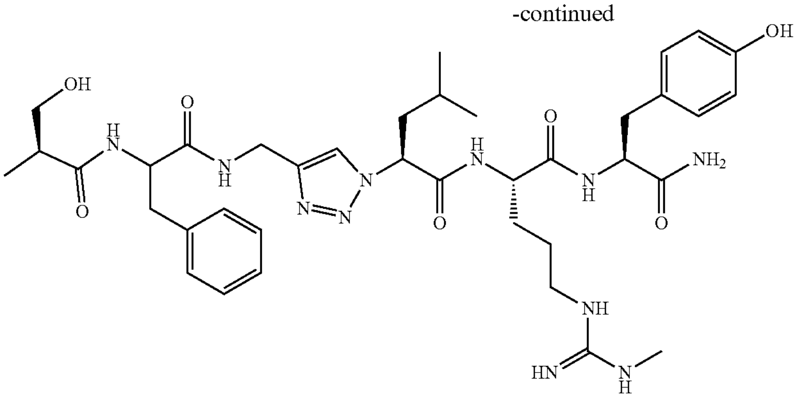

| Biological activities of metastin analogs substituted between positions 50 and 51 H-$AA^{45}$-Asn-Trp-Asn-Ser-$AA^{50-51}$-Leu-$AA^{53}$-Phe-$NH_2$ | | | | | | | |
|---|---|---|---|---|---|---|---|
| | | | | Agonist activity[a] $EC_{50}$ | Binding affinity[c] $IC_{50}$ (nM) | | Stability in mouse serum Residual ratio |
| Compound | $AA^{45}$ | $AA^{50-51}$ | $AA^{53}$ | (nM) | Human | Rat | (%)[e] |
| Metastin (45-54) | Tyr | Phe-Gly | Arg | 0.049[b] | 0.082[a] | 0.11[d] | ND[f] |
| 1 | D-Tyr | Phe-Gly | Arg(Me) | 0.065 | 0.11 | 0.26 | 18.1 |
| 2 | D-Tyr | Phe-Ψ(CSNH)-Gly | Arg(Me) | 0.041 | 2.8 | 3.3 | 35.3 |
| 3 | D-Tyr | Phe-Ψ($CH_2NH$)-Gly | Arg(Me) | 0.62 | 0.61 | 1.4 | 12.1 |
| 4 | D-Tyr | Phe-Ψ(NHCO)-Gly | Arg(Me) | 0.95 | 0.51 | 2.9 | 46.8 |
| 5 | D-Tyr | Phe-azaGly | Arg(Me) | 0.050 | 0.16 | 0.17 | 39.5 |

[a]Agonist activities of all peptide analogs were evaluated in functional assay of human 0T7T175, an intracellular calcium mobilization assay using fluorometric imaging plate reader technology. $EC_{50}$ values of all peptide analogs were calculated using sigmoidal dose response curves.

[b]$EC_{50}$ value of metastin(45-54) were calculated as the average value of 13 independent experiments

[c]Receptor binding affinities of the synthesized peptides were determined as $IC_{50}$ values

[d]$IC_{50}$ value of metastin(45-54) was calculated as the average of three independent experiments

[e]Residual ratio after incubation in mouse serum 1 h at 37° C.

[f]Not Determined

| Biological activities of decapeptide metastin analogs substituted at position 47 H-$AA^{45}$-Asn-$AA^{47}$-Asn-Ser-Phe-$AA^{51}$-Leu-$AA^{53}$-Phe-$NH_2$ | | | | | | | | |
|---|---|---|---|---|---|---|---|---|
| | | | | | Agonist activity[a] $EC_{50}$ | Binding affinity[c] $IC_{50}$ (nM) | | Stability in mouse serum Residual ratio |
| Compound | $AA^{45}$ | $AA^{47}$ | $AA^{51}$ | $AA^{53}$ | (nM) | Human | Rat | (%)[e] |
| Metastin (45-54) | Tyr | Trp | Gly | Arg | 0.049[b] | 0.082[a] | 0.11[d] | ND[f] |
| 6 | D-Tyr | Ser | azaGly | Arg(Me) | 0.73 | 0.49 | 0.43 | 50.0 |
| 7 | D-Tyr | Thr | azaGly | Arg(Me) | 0.24 | 0.86 | 0.83 | 62.5 |
| 8 | D-Tyr | Ile | azaGly | Arg(Me) | 0.13 | 0.43 | 0.46 | ND[f] |
| 9 | D-Tyr | Cha | azaGly | Arg(Me) | 0.10 | 0.19 | 0.24 | 32.0 |
| 10 | D-Tyr | Pya(3) | azaGly | Arg(Me) | 0.24 | 0.70 | 0.89 | 50.6 |
| 11 | D-Tyr | Pya(4) | azaGly | Arg(Me) | 0.11 | 0.30 | 0.28 | 30.7 |
| 12 | D-Tyr | Nal(2) | azaGly | Arg(Me) | 0.098 | 0.13 | 0.20 | 43.6 |
| 13 | D-Tyr | D-Trp | azaGly | Arg(Me) | 0.072 | 0.19 | 0.22 | 56.4 |
| 14 | D-Tyr | D-Pya(4) | azaGly | Arg(Me) | 0.59 | 0.28 | 0.28 | ND[f] |

[a]Agonist activities of all peptide analogs were evaluated in functional assay of human 0T7T175, an intracellular calcium mobilization assay using fluorometric imaging plate reader technology. $EC_{50}$ values of all peptide analogs were calculated using sigmoidal dose response curves.

[b]$EC_{50}$ value of metastin(45-54) were calculated as the average value of 13 independent experiments

[c]Receptor binding affinities of the synthesized peptides were determined as $IC_{50}$ values

[d]$IC_{50}$ value of metastin(45-54) was calculated as the average of three independent experiments

[e]Residual ratio after incubation in mouse serum 1 h at 37° C.

[f]Not Determined

Structures, biological activities, and HPLC retention times of Kp analogs.
R-$AA^{45}$-$AA^{46}$-$AA^{47}$-$AA^{48}$$AA^{49}$-Phe-$AA^{51}$-Leu-$AA^{53}$-$AA^{54}$-$NH_2$

| Compound | R | $AA^{45}$ | $AA^{46}$ | $AA^{47}$ | $AA^{48}$ | $AA^{49}$ | $AA^{51}$ | $AA^{53}$ | $AA^{54}$ | Agonist Activity[a] $EC_{50}$ (nM) | RP-HPLC[b] $t_{ret}$ (min) |
|---|---|---|---|---|---|---|---|---|---|---|---|
| Metastin (45-54) | | Tyr | Asn | Trp | Asn | Ser | Gly | Arg | Phe | 0.087 | — |
| 1 | H | — | D-Tyr | D-Pya(4) | Asn | Ser | azaGly | Arg(Me) | Phe | 0.27 (0.074-0.99) | — |
| 2 | H | — | D-Tyr | Trp | Asn | Ser | azaGly | Arg(Me) | Phe | 0.057 (0.018-0.17) | 5.54 |
| 3 | H | — | — | Trp | Asn | Ser | azaGly | Arg(Me) | Phe | 7.7 (2.2-28) | 5.03 |
| 4 | Ac | — | — | Trp | Asn | Ser | azaGly | Arg(Me) | Phe | 2.1 (0.96-4.6) | 5.76 |
| 5 | 3-(indol-3-yl)propionyl | — | — | — | Asn | Ser | azaGly | Arg(Me) | Phe | 0.13 (0.020-0.86) | 5.95 |
| 6 | 3-phenylpropionyl | — | — | — | Asn | Ser | azaGly | Arg(Me) | Phe | 0.17 (0.067-0.44) | 5.90 |
| 7 | 3-(4-pyridyl)propionyl | — | — | — | Asn | Ser | azaGly | Arg(Me) | Phe | 1.5 (0.48-4.8) | 4.51 |
| 8 | 3-(indol-3-yl)propionyl | — | — | — | — | Ser | azaGly | Arg(Me) | Phe | 8.2 (3.4-20) | 6.17 |
| 9 | 3-(indol-3-yl)propionyl | — | — | — | — | — | azaGly | Arg(Me) | Phe | 0.62 (0.16-2.3) | 6.58 |
| 10 | H | — | — | — | — | — | azaGly | Arg(Me) | Phe | 130 (93-170) | 4.29 |
| 11 | Ac | — | — | — | — | — | azaGly | Arg(Me) | Phe | 0.33 (0.19-0.57) | 5.02 |
| 12 | n-hexanoyl | — | — | — | — | — | azaGly | Arg(Me) | Phe | 1.4 (0.44-4.3) | 6.66 |
| 13 | benzoyl | — | — | — | — | — | azaGly | Arg(Me) | Phe | 0.60 (0.28-1.2) | 6.21 |
| 14 | benzyl | — | — | — | — | — | azaGly | Arg(Me) | Phe | 0.89 (0.23-3.4) | 5.20 |
| 15 | 3-(indol-3-y1)propionyl | — | — | — | — | — | azaGly | Arg(Me) | Trp | 0.022 (0.0072-0.066) | 6.67 |
| 16 | benzoyl | — | — | — | — | — | azaGly | Arg(Me) | Trp | 0.024 (0.0073-0.079) | 6.29 |
| 17 | 2-pyridylcarbonyl | — | — | — | — | — | azaGly | Arg(Me) | Trp | 0.037 (0.0099-0.14) | 6.02 |
| 18 | 3-pyridylcarbonyl | — | — | — | — | — | azaGly | Arg(Me) | Trp | 0.16 (0.037-0.67) | 4.69 |
| 19 | 4-pyridylcarbonyl | — | — | — | — | — | azaGly | Arg(Me) | Trp | 0.068 (0.023-0.20) | 4.48 |
| 20 | 3-furanylcarbonyl | — | — | — | — | — | azaGly | Arg(Me) | Trp | 0.11 (0.021-0.58) | 5.88 |
| 21 | 2-pyrolylcarbonyl | — | — | — | — | — | azaGly | Arg(Me) | Trp | 0.23 (0.18-0.31) | 5.91 |
| 22 | 4-imidazolylcarbonyl | — | — | — | — | — | azaGly | Arg(Me) | Trp | 0.24 (0.062-0.90) | 4.47 |
| 23 | phenylacetyl | — | — | — | — | — | azaGly | Arg(Me) | Trp | 0.27 (0.048-1.5) | 6.49 |
| 24 | cyclohexanoyl | — | — | — | — | — | azaGly | Arg(Me) | Trp | 0.12 (0.017-0.82) | 6.70 |
| 25 | propionyl | — | — | — | — | — | azaGly | Arg(Me) | Trp | 0.13 (0.036-0.49) | 5.52 |
| 26 | isobutyryl | — | — | — | — | — | azaGly | Arg(Me) | Trp | 0.058 (0.013-0.26) | 5.88 |
| 27 | cyclopropylcarbonyl | — | — | — | — | — | azaGly | Arg(Me) | Trp | 0.028 (0.0081-0.096) | 5.70 |

[a] $EC_{50}$ values [nM (95% confidence interval)] of $[Ca^{2+}]$ increasing activities of all peptide analogs were evaluated in CHO cells expressing human KISS1R.

[b] Retention times ($t_{ret}$) of peptide analogs were measured via RP-HPLC. Elution conditions: linear density gradient elution on Merck Chromolith ® Performance RP-18e (4.6 × 100 mm), with eluents A/B = 95/5-35/65 (10 min), using 0.1% TFA in water as eluent A and 0.1% TFA-containing acetonitrile as eluent B; flow rate: 3.0 mL/min.

acceptable hydrate, solvate, acid or salt, and can be amorphous or in any crystalline form, or as an oil or wax. Any pharmaceutically acceptable salt can be used, as may be convenient. Generally, these salts are derived from pharmaceutically and biologically acceptable inorganic or organic acids and bases or metals. Examples of such salts include, but are not limited to: acetate, adipate, alginate, ammonium, aspartate, benzoate, benzenesulfonate (besylate), bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, methanesulfonate (mesylate), 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts.

The compounds also include any or all stereochemical forms of the therapeutic agents (i.e., the R and/or S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of some embodiments are also meant to include compounds which differ only in the presence of one or more isotopically enriched atoms. For example, therapeutic agents in which one or more atom is replaced by, for example, deuterium, tritium, $^{13}C$, $^{14}C$ (or any isotopic labels as commonly used in the art such as phosphorus, calcium, iodine, chlorine, bromine, or any other convenient element for isotopic labeling) are within the scope of this invention.

Compounds such as TAK-448, and the other compounds according to embodiments of the invention, can be administered to the subject by any suitable route or method as known in the art. Suitable routes of admiration include, but are not limited to, oral administration, intravenous, intraarterial, intrathecal, intraperitoneal, intradermal, subcutaneous, intramuscular or intraperitoneal injections, rectal or vaginal administration by way of suppositories or enema, transmucosal, transdermal, buccal, nasal, inhalation, sublingual, topical, or local administration directly into or onto a target tissue, or administration by any route or method that delivers a therapeutically effective amount of the drug or composition to the cells or tissue to which it is targeted. When administration is oral, the dosage form preferable is a delayed release or other formulation that allows the compound to be absorbed prior to degradation of a peptide or peptide analog compound. Preferably, the methods of embodiments of this invention involve administration subcutaneously or intravenously. The administration can be given by transfusion or infusion, and can be administered by an implant, an implanted pump, or an external pump, or any device known in the art.

In preferred method embodiments, the compounds described herein are formulated and are administered as a pharmaceutical composition that includes a pharmaceutically acceptable carrier and one or more pharmaceutical agent, including one or more of the inventive compounds described herein, and including one or more of the inventive compounds described herein optionally with an additional agent, such as a fatty liver reducing drug of the same or another class, for a combination therapy.

Exemplary compounds for use in a combination treatment, simultaneously or sequentially with the compounds of this invention, such as TAK-488, include but are not limited to an ACC inhibitor, AMPK, AKR-001, aramchol, ASC40, AZD7687, BI-1467335, BIO89-100, BMS-986036, canagliflozin, cenicriviroc, cilofexor, dapagliflozin, DGATEDP-305, elafibranor, elobixibat, empagliflozin, emricasan, exenatide, EYP001a, FALCON1 (PEG-FGF21, an FASN inhibitor, fenofibrate, firsocostat, an FXR agonist, GR-MD-02, IONIS-DGAT2Rx, ipragliflozin, licogliflozin, liraglutide, luseogliflozin, LY3202328, MET409, MGL-3196, MK-4074, MSDC-0602K, MT-3995, NGM282, nidufexor, OAT-1251, obeticholic acid, OCA, OWL833, PF-05221304, PF-06835919, PF-06865571, PF-06882961, pioglitazone, PX-102, PXL770, PXS-5153A, seladelpar, selonsertib, semaglutide, simtuzumab, TERN-101, TERN-201, troifexor, TTP273, vitamin D, vitamin E, VK2809, and volixibat. In addition, treatment by administration with the compounds TAK-488, kisspeptin, and their variants, can be accompanied by a first line treatment including diet and exercise changes and weight loss.

A pharmaceutically acceptable carrier refers to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art. A suitable carrier depends on the route of administration contemplated for the pharmaceutical composition.

A non-inclusive list of carriers and vehicles contemplated for use with the invention follows: fillers, diluents, adjuvants, pH adjusters, buffers, preservatives, binders and disintegrants, solvents, lipids, liposomes, emulsions, suspensions, and containers (e.g., ampoules, bottles, pre-filled syringes, and the like).

Liquid carriers can be in the form of a solution, suspension, emulsion, oil, gel, and the like, and include, for example aqueous solution (e.g., saline solutions, phosphate-buffered saline solutions, Ringer's, and the like), oil-in-water or water-in-oil emulsions, liposomes, and the like. Gaseous carriers can include, for example air, oxygen, fluorocarbons, dispersing agents, and the like. Solid carriers can include, for example, starch (e.g., corn starch, potato starch, rice starch, and the like), cellulose (e.g., microcrystalline cellulose, and the like), sugars (e.g., lactose, sucrose, glucose, and the like), clays, minerals (e.g., talc, and the like), gums, flavorings, preservatives, colorings, taste-masking agents, sweeteners, lipids, oils, solvents, saline solutions, emulsifiers, suspending agents, wetting agents, dispersants, binders, lubricants (e.g., magnesium stearate and the like), salts, pH modifiers (e.g., acids or bases), buffers, and the like.

Pharmaceutical compositions suitable for injection comprise sterile aqueous solutions (where water soluble) or dispersions, suspensions or emulsions, and sterile powders or granules for the extemporaneous preparation of sterile injectable solutions or dispersions. For intravenous administration, suitable carriers comprise physiological saline, bacteriostatic water, Cremophor EL™ (BASF™, Parsippany, N.J.) or (e.g., phosphate) buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, isotonic agents are included in the composition, for example, sugars, polyalcohols such as mannitol, sorbitol, or sodium chloride. Prolonged absorption of an injectable composition can be achieved by including in the composition an agent that delays absorption, for example, aluminum monostearate or gelatin.

Extended and sustained release compositions also are contemplated for use with and in the inventive embodiments. Thus, suitable carriers can include any of the known ingredients to achieve a delayed release, extended release or sustained release of the active components.

Routes of administration are determined by the person of skill according to convenience, the health and condition of the subject to be treated, and the location and stage of the condition to be treated. Therefore, the forms which the pharmaceutical composition can take will include, but are not limited to: tablets, capsules, caplets, lozenges, dragees, pills, granules, oral solutions, powders for dilution, powders for inhalation, vapors, gases, sterile solutions or other liquids for injection or infusion, transdermal patches, buccal patches, inserts and implants, rectal suppositories, vaginal suppositories, creams, lotions, oils, ointments, topical coverings (e.g., wound coverings and bandages), suspensions, emulsions, lipid vesicles, and the like.

Treatment regimens include a single administration or a course of administrations lasting two or more days, including a week, two weeks, several weeks, a month, two months, several months, a year, or more, including administration for the remainder of the subject's life. The regimen can include multiple doses per day, one dose per day or per week, for example, or a long infusion administration lasting for an hour, multiple hours, a full day, or longer.

Suitable dosages can be determined by the treating physician depending on the patient, the condition to be treated, and the severity of the condition to be treated. Such dosages can include any amount, dosage, or dosage regimen that produces a desired result. Dosage amounts per administration include any amount determined by the practitioner, and will depend on the size of the subject to be treated, the state of the health of the subject, the route of administration, the condition to be treated or prevented, and the like.

In general, it is contemplated that for the majority of subjects, a dose in the range of about 0.01 nmol per hour to about 10 nmol per hour is suitable, preferably about 0.1 nmol per hour to about 5 nmol per hour, are useful, given over a course of about 1 hour to about 72 hours, or about 24 hours to about 48 hours, or over a period of days, weeks, or longer. This dose can be administered weekly, daily, or multiple times per day, or as a continuous infusion, transdermal formulation, or depot formulation.

In addition, a single injected dose of about 0.01 mg, about 0.02 mg, about 0.025 mg, about 0.05 mg, about 0.1 mg, about 0.2 mg, about 0.5 mg, about 1 mg, about 2 mg, about 3 mg, about 4 mg, about 5 mg, or more can be administered. Alternatively, a single injected dose of about 0.002 μmol/kg, about 0.004 μmol/kg, about 0.008 μmol/kg, about 0.01 μmol/kg, about 0.025 μmol/kg, about 0.5 μmol/kg, about 0.75 μmol/kg, about 1 μmol/kg, about 2 μmol/kg, about 5 μmol/kg, about 8 μmol/kg, about 10 μmol/kg, or more can be administered.

4. Summary of Results

Hepatic Kiss1R knock-out mice fed with HFD (Western high fat diet, 60% kcal fat) have a greater increase in body weight, liver steatosis and liver triglycerides when compared to littermate controls on HFD, despite no change in food intake. This implicates the pathologic role of kisspeptin/Kiss1R pathway in the pathogenesis of NAFLD and other fatty liver conditions.

Hepatic Kiss1R knock-out mice were also glucose intolerant and insulin resistant, compared to controls (all on HFD). The livers from hepatic KISS1R knock-out mice livers displayed a significant increase in biochemical markers for NASH/fibrosis (e.g. TGFβ, collagen), and proinflammatory cytokines (Interleukins (IL)-1α, Mip2, IP10), compared to controls (all on HFD).

Subcutaneous administration of TAK-448 protected HFD-fed mice against the development of NAFLD compared to mice treated with Vehicle (PBS) control.

TAK-448 administered for one month to HFD-fed mice prevented the accumulation of liver triglycerides and the rise in free fatty acids and glycerol (triglyceride building blocks) in the blood. These changes occurred without a change in food intake, compared to vehicle-treated controls on HFD who developed NAFLD.

TAK-448 treatment also protected against peripheral fat accumulation and insulin resistance.

5. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

Example 1: Methods and Materials

A. Animals

Animal studies were approved according to guidelines established by the Institutional Animal Care and Use Committee at Rutgers University. Kiss1rAlb-Cre knockout mice were generated by crossing a male Alb-Cre+/− to a female Kiss1rrf/fl. Alb-Cre mice were purchased from Jackson Laboratories™. The Kiss1rrf/fl mouse was generated according to know methods. The F1 generation was Kiss1rfl/+, AlbCre+/− or Kiss1rfl/+, AlbCre−/−. The Kiss1rfl/+, AlbCre+/− was back-crossed to the Kiss1rfl/fl to generate Kiss1rfl/fl, AlbCre+/− (liver knockout: LKO) and Kiss1rfl/fl (littermate controls). Mice were housed in a pathogen-free barrier facility maintained on a 12-hour light/dark cycle.

Four-week-old male LKO and control mice were fed a high fat diet (HFD: 60% kcal fat, 0.2796% cholesterol, 20% calories from carbohydrate (Research Diets™ catalog #D12492, New Brunswick, NJ) or regular control chow diet (RD). Mice were group-housed and provided food and water ad libitum. Five months after commencing the designated diet, a glucose tolerance test was performed, followed by insulin tolerance test a week later. Total body weights were measured weekly for 24 weeks after commencing the designated diet and then animals were euthanized.

B. Administration of KP-Analog TAK-488.

C57BL6/J male mice (4 weeks of age) were maintained on a HFD or RD for 6 weeks and then fasting blood glucose was measured. An Azlet™ mini-osmotic pump model 2004 containing TAK-448 (0.3 nmol/hour) or PBS (vehicle controls) were inserted subcutaneously into the flanks of mice, according to known methods. Animals were treated for 4 weeks unless otherwise indicated and maintained on RD or HFD (total of 10 weeks).

C. Metabolic Tests.

Blood glucose measurements were obtained via a small nick in the lateral tail vein using a glucometer (Bayer Contour™). For glucose tolerance tests, mice were fasted for 12 hours and then injected intraperitoneally with D-glucose (1 g/kg). For the insulin tolerance tests, mice were fasted for 6 hours and then injected intraperitoneally with insulin (0.5 U/kg; Novo Nordisk™).

D. Metabolic Cage Assessments.

Mice where individually housed in an 8-chamber Clinical Laboratory Animal Monitoring System (CLAMS) with controlled light and feeding. Carbon dioxide output, oxygen update, respiratory exchange ratio (RER), ambulatory movement, and feeding were measured over a 4-day period.

E. Insulin, Glycerol, Triglycerides, ALT, FFA, and Cholesterol Measurements.

Serum insulin levels were measured using the Ultra-Sensitive Mouse Insulin ELISA Kit (Crystal Chem™). Serum glycerol levels were measured using the Glycerol Assay Kit (Sigma™). Liver triglycerides were measured using the triglyceride quantification kit (MBL™ international Catalog #JM-K622-500). Free fatty acids were measured using the Free Fatty Acid Quantification Kit (Sigma™, MAK044-1KT). ALT levels were measured using Liquid ALT (SGPT) Reagent set according to the manufacturer's instructions; cholesterol levels were measured using the Cholesterol set according to the manufacturer's instructions.

F. Immunoblot Assays.

Immunoblot assays were conducted according to known methods. Mouse liver tissue or primary hepatocytes were homogenized in RIPA lysis buffer containing protease inhibitors and centrifuged at 4° C.; the protein expression in lysates was analyzed by Western blot analysis. Protein was separated using SDS-PAGE and probed using the following antibodies: Abcam™ (rabbit anti-KISS1R 1:1000; rabbit anti-MOGAT1 1:1000), Cell Signaling Technology™ (rabbit anti-pAMPK, rabbit anti-AMPK, rabbit anti-pACC, rabbit anti-FASN, rabbit anti-PPAR-γ, rabbit anti-CD36, and rabbit anti-GYK all 1:1000), Proteintech™ (rabbit anti-KISS1 1:750). Mouse anti-β actin (1:5000, Thermo Fisher Scientific™) or anti-vinculin (1:1000, Bio-Rad™) were used for loading control. Protein was then incubated for 1 hour in horseradish peroxidase (HRP)-conjugated rabbit (1:2500, Cell Signaling Technology™) or mouse (1:2500, Cell Signaling Technology™) secondary antibody. Blots were imaged by chemiluminescence with ChemiDoc™ Touch imaging system (Bio-Rad™), SuperSignal and West Dura Extended Duration Substrate (Thermo Scientific™). Protein levels were quantified using Image Lab Software (Bio-Rad™).

G. Quantitative Real-Time PCR (qPCR).

Total RNA was extracted from cells using the Trizol method. Reverse transcription was done according to manufacturer's instructions using iScript RT Supermix (Bio-Rad™). Gene expression was determined using SYBR green real-time qPCR (RT-qPCR) as described previously using primers shown in Table 7, below. The following primers were purchased from BioRad™ (validated PCRPrime™ primers): Srebp1, Aqp3, Aqp9, Gpat2, Agpat2, Dgat1, Dgat2, Mogat1, Slc2a2, Dgkg, Dgkh, Lgpat1, Sod1, Sod2, Gss, Ucp2, and Gpam. Il-13 was purchased from Qiagen™ (QT00099554). Primers for Srebf1, Aqp3, Aqp9, Gpat2, Agpat2, Dgat1, Dgat2, Mogat1, Slc2a2, Lgpat1, Sod1, Sod2, Gss, Ucp2, and Gpam are pre-made and were purchased from BioRad™.

TABLE 7

Primer Sequences.

| Name | Sequence | Forward/ Reverse | SEQ ID NO |
|---|---|---|---|
| Lfabp | GCAGAGCCAGGAGAACTTTGAG | Forward | 47 |
| Lfabp | TTTGATTTTCTTCCCTTCATGCA | Reverse | 48 |
| Cd36 | GATGACGTGGCAAAGAACAG | Forward | 49 |
| Cd36 | TCCTCGGGGTCCTGAGTTAT | Reverse | 50 |
| Acaca | ATGGGCGGAATGGTCTCTTTC | Forward | 51 |
| Acaca | TGGGGACCTTGTCTTCATCAT | Reverse | 52 |
| Fasn | GGAGGTGGTGATAGCCGGTAT | Forward | 53 |
| Fasn | TGGGTAATCCATAGAGCCCAG | Reverse | 54 |
| Gyk1 | ATCCGCTGGCTAAGAGACAACC | Forward | 55 |
| Gyk1 | TGCACTGGGCTCCCAATAAGG | Reverse | 56 |
| G6pc | AAAAAGCCAACGTATGGATTCCG | Forward | 57 |
| G6pc | CAGCAAGGTAGATCCGGGA | Reverse | 58 |
| Pck1 | AGCATTCAACGCCAGGTTC | Forward | 59 |
| Pck1 | CGAGTCTGTCAGTTCAATACCAA | Reverse | 60 |
| Gpd1 | CCACTGTTTTGGGACTCTCT | Forward | 61 |
| Gpd1 | CGGGTGTGTTCTTCAAAGTC | Reverse | 62 |
| Mip2 | CCCAGACAGAAGTCATAGCCAC | Forward | 63 |
| Mip2 | GCCTTGCCTTTGTTCAGTATC | Reverse | 64 |
| Mcp1 | AATGAGTAGCAGCAGGTGAGTG | Forward | 65 |
| Mcp1 | GAAGCCAGCTCTCTCTTCCTC | Reverse | 66 |
| Il1a | CGCTTGAGTCGGCAAAGAAA | Forward | 67 |
| Il1a | TGATACTGTCACCCGGCTCT | Reverse | 68 |
| Ip10 | AAGTGCTGCCGTCATTTTCT | Forward | 69 |
| Ip10 | GTGGCAATGATCTCAACACG | Reverse | 70 |
| Tgfb | TGACGTCACTGGAGTTGTACGG | Forward | 71 |
| Tgfb | GGTTCATGTCATGGATGGTGC | Reverse | 72 |
| Kiss1r | CTGCCACAGACGTCACTTTC | Forward | 73 |
| Kiss1r | ACATACCAGCGGTCCACACT | Reverse | 74 |

TABLE 7-continued

| Primer Sequences. | | | |
|---|---|---|---|
| Name | Sequence | Forward/ Reverse | SEQ ID NO |
| Kiss1 | AGCTGCTGCTTCTCCTCTGT | Forward | 75 |
| Kiss1 | GCATACCGCGATTCCTTTT | Reverse | 76 |
| Ppary | CGACATGAGTTCCTTTATGATGGG | Forward | 77 |
| Ppary | TGTGATCTCTTGCACGGCTT | Reverse | 78 |
| Col1a2 | GCAGGGTTCCAACGATGTTG | Forward | 79 |
| Col1a2 | GCAGCCATCGACTAGGACAGA | Reverse | 80 |
| Timp1 | CCTTGCAAACTGGAGAGTGACA | Forward | 81 |
| Timp1 | AGGCAAAGTGATCGCTCTGGT | Reverse | 82 |
| Il1b | CAACCAACAAGTGATATTCTCCATG | Forward | 83 |
| Il1b | GATCCACACTCTCCAGCTGCA | Reverse | 84 |
| Sma | ACTGGGACGACATGGAAAAG | Forward | 85 |
| Sma | GTTCAGTGGTGCCTCTGTCA | Reverse | 86 |
| Rpl13a | GCTGCTCTCAAGGTTGTTCG | Forward | 87 |
| Rpl13a | CCTTTTCCTTCCGTTTCTCC | Reverse | 88 |

H. Histological Analysis.

Liver tissue was immediately fixed in 10% neutral formalin after mice were euthanized. Tissue was processed for histology by the Research Pathology Services at Rutgers University. Livers were sectioned into 5 μm thick sections and stained with hematoxylin and eosin. Sections were examined by light microscopy for histopathological changes.

I. Metabolomic Analysis by Liquid Chromatography-Mass Spectrometry (LC-MS).

Metabolomics analysis of serum and liver by LC-MS was conducted according to known methods. LC-MS analysis of cell metabolites was conducted on Q Exactive Plus Hybrid Quadrupole Orbitrap mass spectrometer (Thermo Fisher Scientific™) and with hydrophilic interaction chromatography. Data was obtained using the MAVEN software with each labeled isotope (mass accuracy window: 5 ppm). Labeled isotope natural abundance and impurity were corrected using the AccuCor package coded in R.

J. Mouse Primary Hepatocyte Studies.

Primary hepatocytes from mice were isolated according to known methods. Mice (wild-type, C57BL6) or LKO and littermate controls were anesthetized using a ketamine/xylazine mixture (Henry Schein™). The liver was cannulated via the hepatic portal vein and first perfused with 37° C. Kreb's Ringer solution containing EGTA for 10 minutes. After the first wash, a second Kreb's Ringer solution containing CaCl2 and LIBERASE (Roche™) was used until the liver was thoroughly perfused. Hepatocytes were filtered through a gauze mesh and resuspended in William's Media E (Sigma™) with 10% FBS (Sigma™), 200 nM dexamethasone (Sigma™), 5 mM pen/strep (Fisher™), 2 mM L-glutamine (Fisher™). Cells were plated at a density of $3\times10^5$ on 6-well collagen-coated plates (Sigma™). Hepatocytes were left to recover overnight and then were serum starved for 3 hours prior to experiments. For free fatty acid (FFA) loading, 150 μM oleic and 150 μM palmitic acid was conjugated with 2% BSA (0.3 mM). Cells were loaded with FFA post isolation and left to recover overnight prior to serum starvation, and then treated with KP-10 or TAK.

K. Statistical Analysis.

Statistical significance between two groups was determined by unpaired two-tailed Student's t test. For comparison among multiple groups, one-way analysis of variance followed by Dunnett's multiple comparisons test was used. P value <0.05 is considered to be statistically significant. Graphs were generated with GraphPad™ Prism version 8.3.1 (San Diego, CA).

Figure 1A:
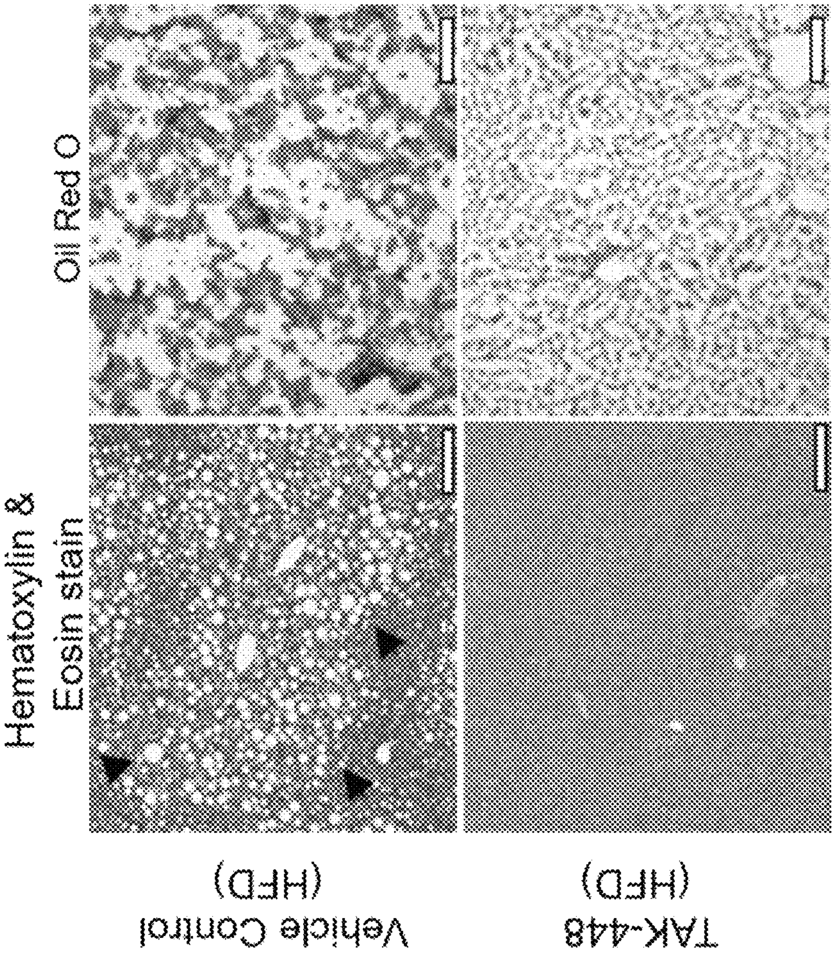
FIG. 1A through FIG. 1J.
Figure 1B:
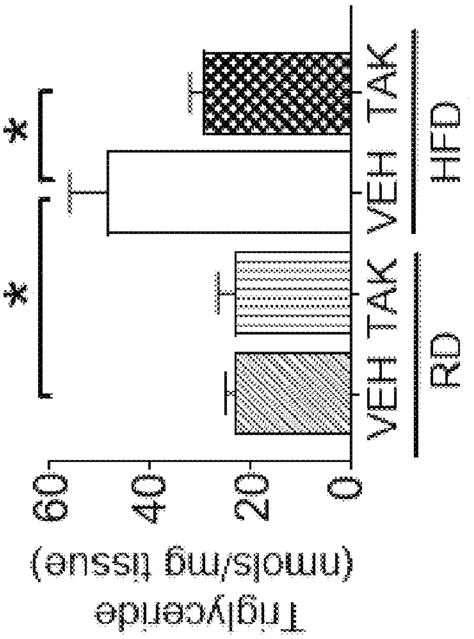
Figure 1C:
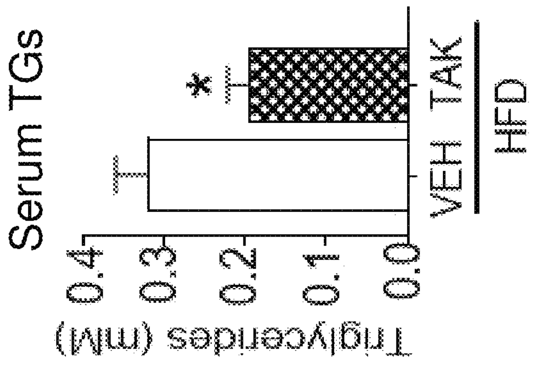
Figure 1D:
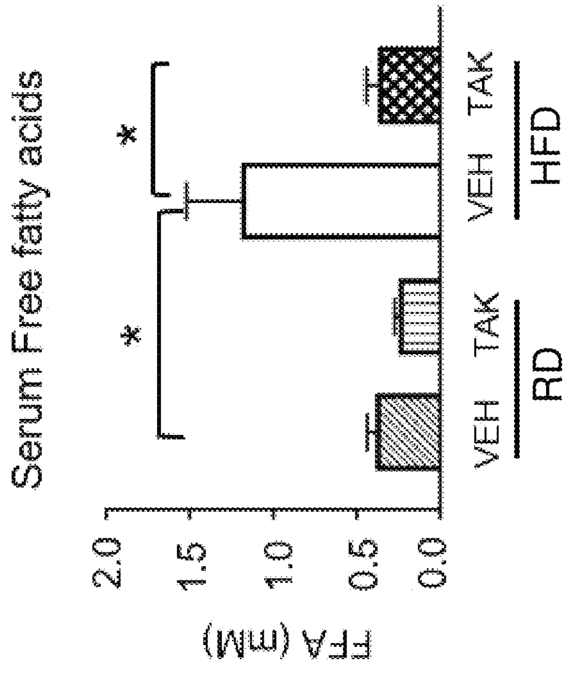

Example 2: Initial Studies; Kisspeptin Analog (TAK-448) Administration Protects Against NAFLD and Insulin Resistance in a Mouse Model of NAFLD C57BL/6J mice fed high fat diet (HFD) or control regular diet (RD) for 12 weeks (4-5/group). TAK-448 (TAK) or Vehicle (Veh i.e., PBS controls) were administered for 4 weeks using an ALZET mini-osmotic pump implanted subcutaneously. See FIG. 1 for results. Steatosis is shown by hematoxylin and eosin stained mouse livers (lipid accumulation, small white droplets, arrowheads) and by Oil Red O staining of lipids (red dots) in control livers (FIG. 1A). This was prevented in the TAK-448 treated group (FIG. 1A). FIG. 1B through FIG. 1G show the endpoint liver triglycerides, endpoint blood glycerol, blood free fatty acids, body weight, epididymal white adipose tissue fat accumulation, and inguinal white adipose tissue fat accumulation, respectively. TAK-448 treatment prevented the rise in fasting glucose (measure of gluconeogenesis by liver) and prevented glucose intolerance and insulin resistance, as measured by a glucose tolerance test (GTT) or insulin tolerance tests (ITT), respectively. See FIG. 1H through FIG. 1J (black bar/line) vs controls (red bar/line). *, p<0.05; student t-test or One-way ANOVA and Dunnett's post-hoc test. TAK-448 can be administered to delay or prevent disease progression in (1) and NAFLD patients (with or without Type II diabetes) and (2) NASH patients.

Figure 2A:
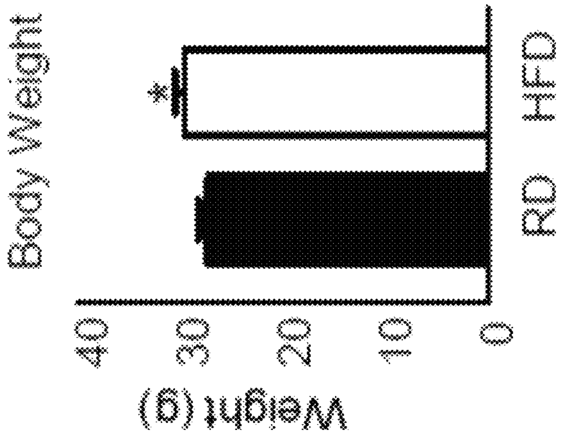
FIG. 2A through FIG. 2C, FIG. 2A and FIG. 2B show the body weights (FIG. 2A) and fasting glucose (FIG. 2B) in mice prior to treatment with Vehicle (VEH, PBS) or Takeda-488(TAK, 0.3 nmol/h).
Figure 2B:
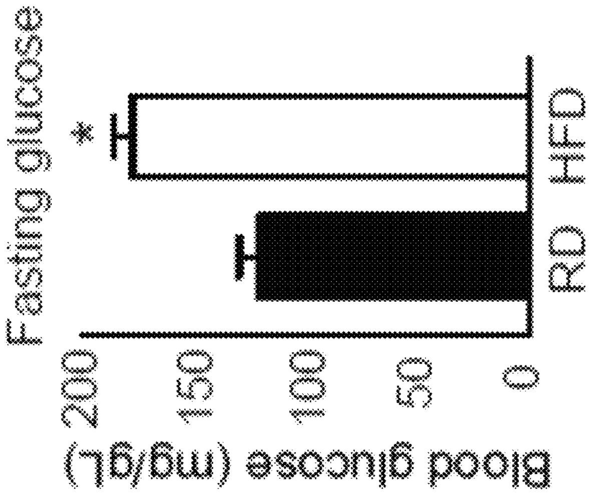
Figure 2C:
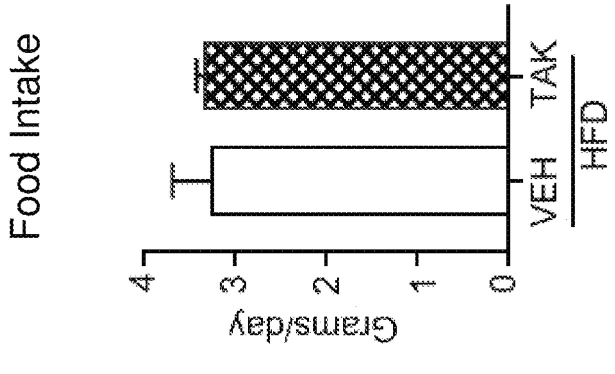
Figure 3A:
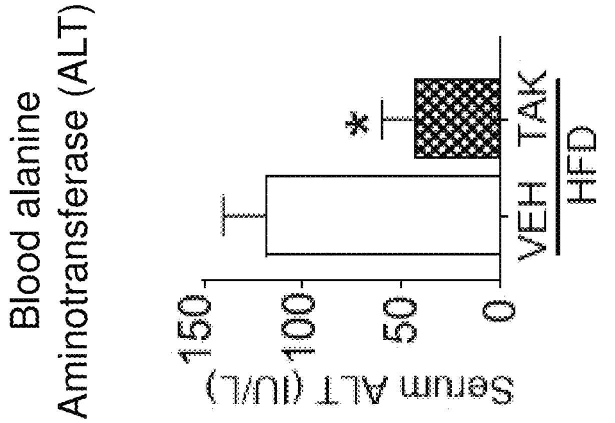
FIG. 3A through FIG. 3C show serum enzyme alanine aminotransferase (ALT) levels, marker for fatty liver (FIG, 3A), serum cholesterol (FIG. 3B), and serum glycerol (FIG. 3C) levels in controls and TAK-treated mice (4 weeks post treatment) on RD/HFD (10 weeks), Administration of TAK-448 lowers ALT, cholesterol and glycerol levels in HFD-fed mice compared to controls on HFD.
Figure 3C:
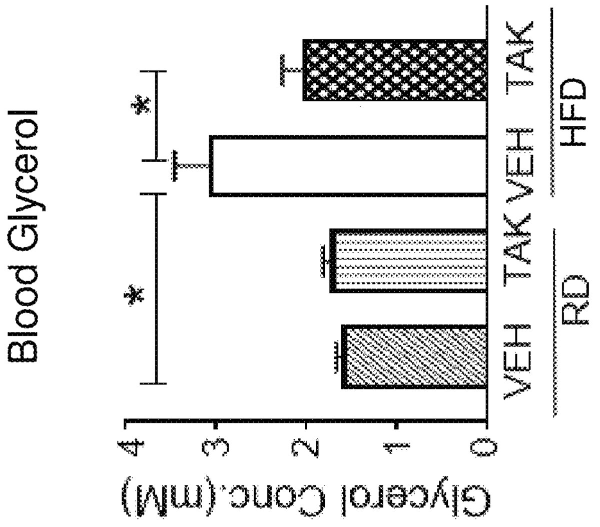
Figure 3B:
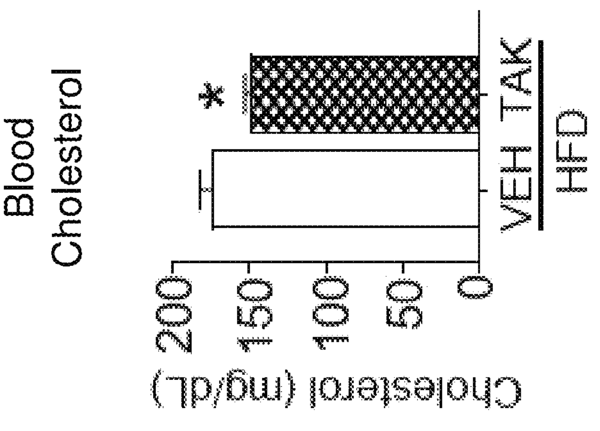
Figure 4B:
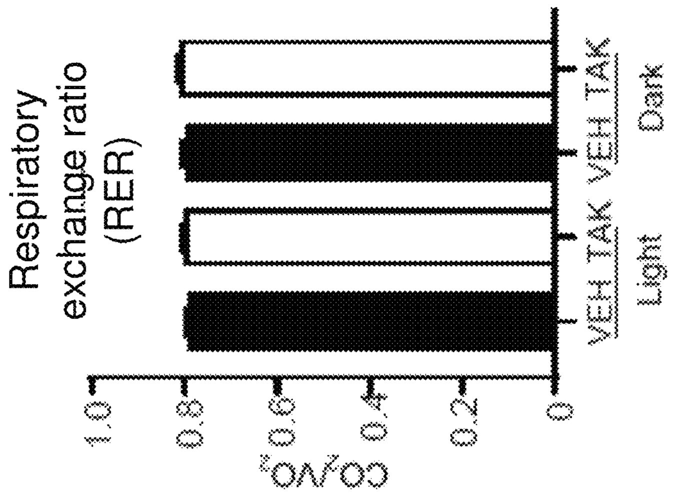
FIG. 4A and FIG. 4B shows CLAMS analysis displaying heat expenditure (FIG. 17A) and respiratory exchange ratio (RER) (FIG. 17B) in vehicle (VEH, PBS) controls and TAK-treated mice (4 weeks post treatment, 10 weeks on RD/HFD; 5 mice/group).
Figure 4A:
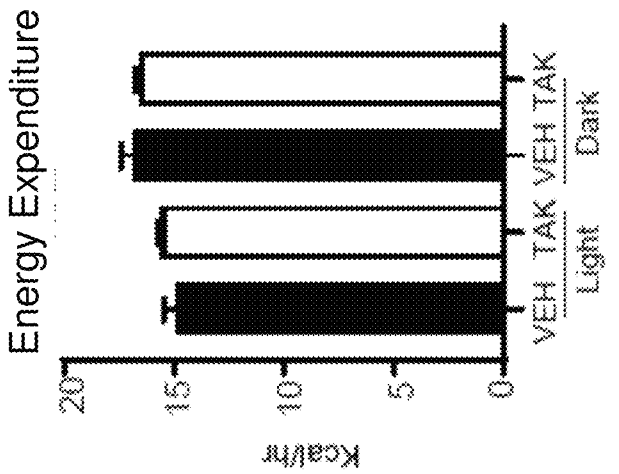

Example 3: Initial Studies; Hepatic Knock-Out (KO) of Kiss1r Promotes Weight Gain, Hepatic Steatosis and Lipid Accumulation in a Mouse Model of NAFLD Hepatic Kiss1r KO (LKO) were generated by crossing a Kiss1r fl/fl mouse to Alb-Cre mouse (Jackson Labs™). Littermate controls (Kiss1r fl/fl) and Kiss1r KO mice (3 weeks old, 10/group) were fed regular diet (RD) or HFD diet for 24 weeks. LKO mice had significant increase in body weight (FIG. 2A through FIG. 2C), despite no changes in food intake (FIG. 2D). H&E stained mouse livers showed strikingly increase in steatosis in the LKO livers compared to controls (all on HFD) (FIG. 3A). In contrast, steatosis was not observed in livers of animals maintained on RD (FIG. 3B). The boxed area is magnified in the lower image. FIG. 4A shows liver triglycerides in mice. *, p<0.05 Student t-test or One-way ANOVA and Dunnett's post-hoc test.

Example 4: Hepatic Kiss1R Knockouts Exhibit Increased Hepatic Steatosis in a Diet-Induced Mouse Model of NAFLD A. Hepatic KISS1R Deficiency Aggravates Hepatosteatosis in Obese, Insulin Resistant Mice.

Figure 5A:
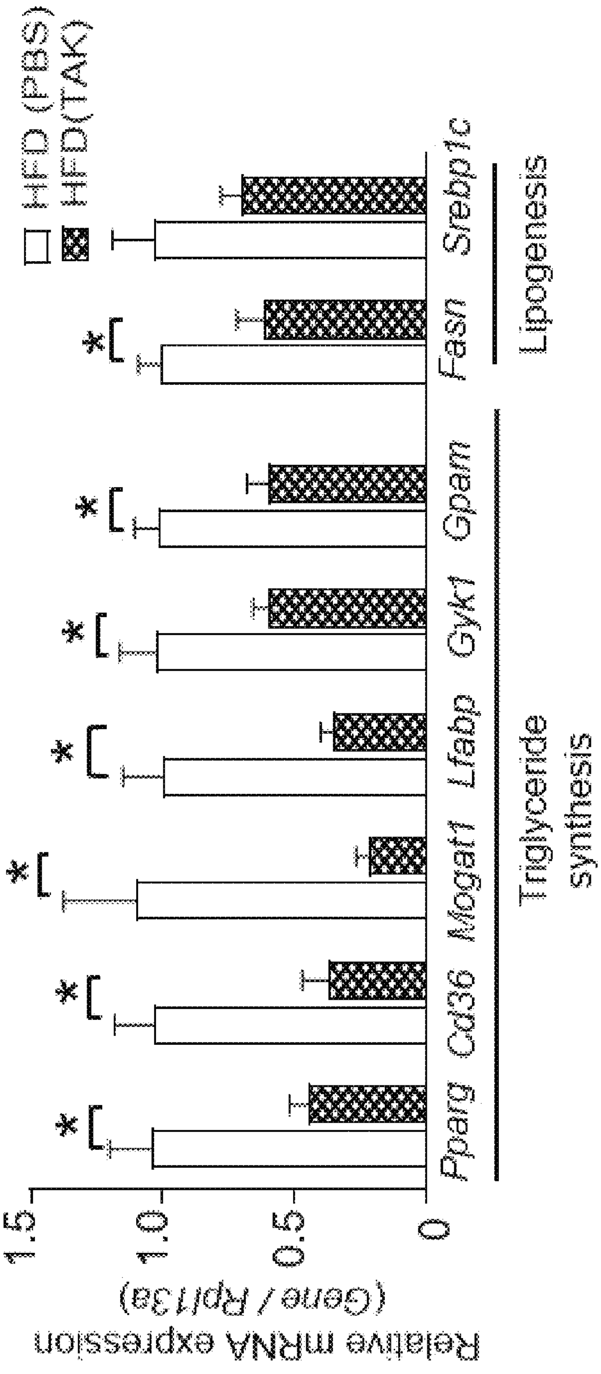
FIG. 5A and FIG. 5B.
Figure 5B:
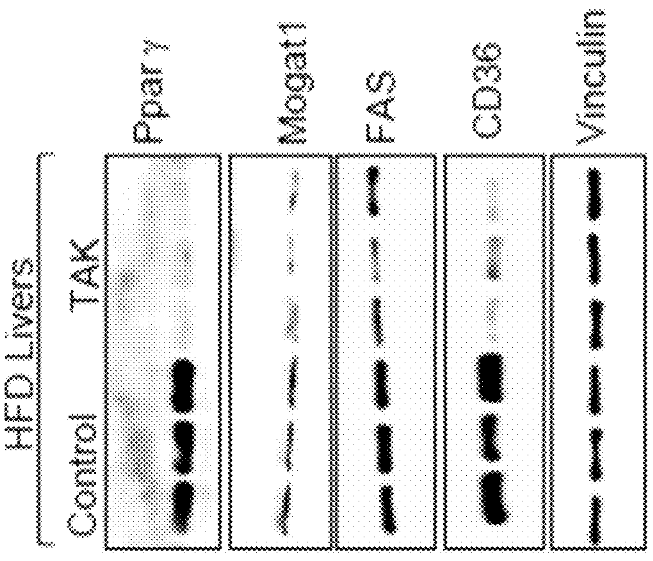

To test whether or not hepatic KISS1/KISS1R is involved in the pathogenesis of NAFLD, hepatic Kiss1/Kiss1r expression was measured in a diet-induced mouse model of NAFLD. After 4-week old wild-type C57BL/6 mice were fed a high fat diet (HFD) for 8 weeks, Kiss1 and Kiss1r mRNA levels were significantly increased in the livers. See FIG. 5, which shows the relative mRNA expression of Kiss1 and Kiss1r by RT-qPCR normalized to Rpl13a mRNA expression in C57BL6 male mice on regular diet (RD) or high fat diet (HFD) for 8 weeks.

Figure 6A:
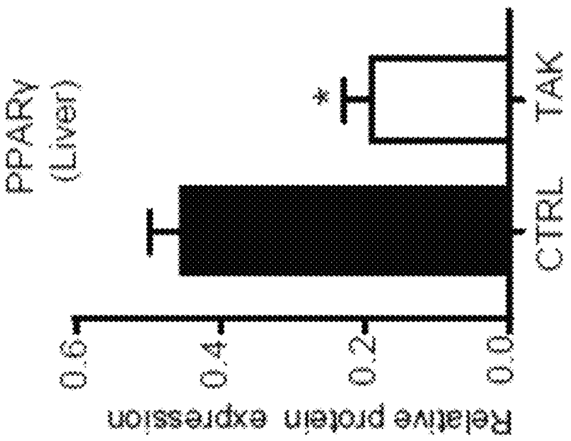
FIG. 6A through FIG. 6C show densitometric analysis of the western blots shown in FIG. 5B.
Figure 6B:
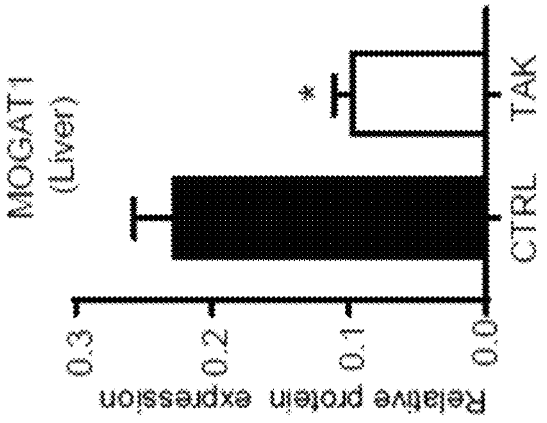

Next, to investigate a role for KISS1R in regulating hepatic lipid metabolism, a liver-specific knockout of Kiss1r (LKO) was generated. Analysis of the LKO mice showed that Kiss1r expression, but not Kiss1, was significantly reduced. See FIG. 6A. LKO mice and their littermate controls were then placed on control regular diet (RD) or HFD. LKO and control mice fed a RD showed no difference in body weight (FIG. 6B). However, as early as 14 days after being placed on the HFD, LKO mice displayed significantly increased body weights compared to controls during the first 10 weeks on high fat diet (HFD) despite showing no differences in food intake (FIG. 2A). HFD (24 weeks) but not RD induced steatosis in LKO mice (FIG. 3) and resulted in an increase in liver triglycerides compared to controls on HFD (FIG. 4A).

Figure 6C:
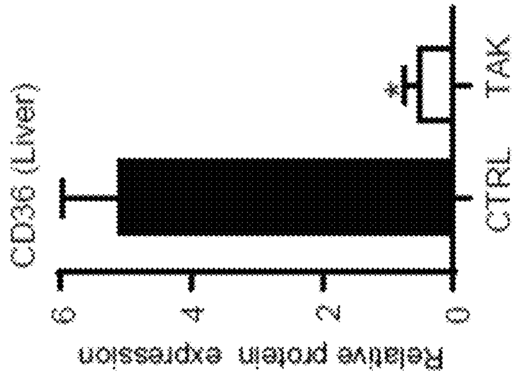
Figure 7:
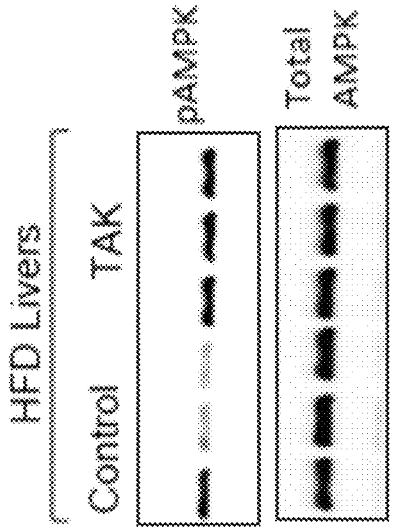
FIG. 7 is a western blot showing pAMPK and total AMPK.

Interestingly, LKO mice exhibited lower heat expenditure compared to controls (FIG. 7A; heat expenditure assessed by CLAMS), indicating a slower metabolism. Differences in RER (respiratory exchange rate) and ambulatory activity were not observed between groups (FIG. 6C and FIG. 6D). Serum alanine transaminase (ALT) levels were elevated in both HFD groups compared to RD, indicating HFD-induced hepatocellular injury (FIG. 7B).

Figure 8B:
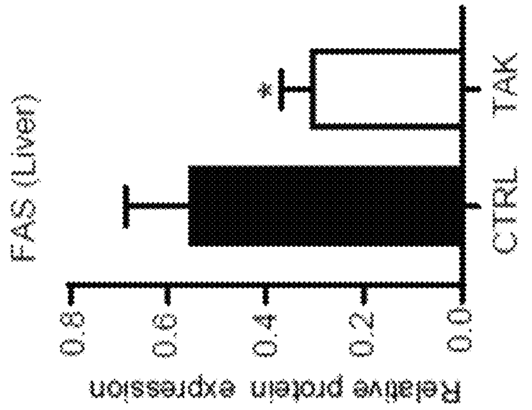
FIG. 8A and FIG. 8B show densitometric analysis of the western blots shown in FIG. 20 and FIG. 18B, respectively.
Figure 8A:
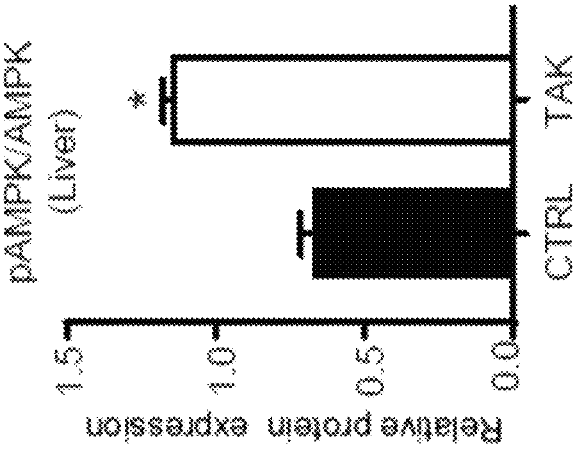

LKO mice also exhibited a decrease in muscle mass (FIG. 8A and FIG. 8B), and an increase in inguinal white adipose tissue, although no changes were observed in epididymal white adipose tissue compared to controls on HFD (FIG. 8C and FIG. 8D). The increase in liver TGs in the LKO HFD mice suggest that hepatic KISS1R plays a protective function in the liver against steatosis.

B. Hepatic KISS1R Deficiency Upregulates Genes Regulating Lipogenesis and Free Fatty Acid (FFA) Uptake.

To elucidate the mechanism underlying hepatic lipid accumulation in LKO mice, the levels of hepatic regulators of fatty acid uptake (the fatty acid translocase, cluster of differentiation (Cd36), liver fatty acid-binding protein, (Lfabp1)), and lipogenesis (peroxisome proliferator-activated receptor γ (PPARγ, encoded by Pparg), sterol regulatory element binding protein-1 (SREBP1, encoded by Srebf1) and its downstream target fatty acid synthase (FAS, encoded by Fasn)) were measured. Under HFD conditions, there was a significant upregulation of all genes (FIG. 9A; relative mRNA expression of indicated genes in liver samples (HFD) normalized to Rpl13a mRNA expression) except for Acaca, that encodes acetyl-CoA carboxylase 1 (ACC1) which catalyzes the first committed step of de novo fatty acids synthesis. Protein levels of PPAR-γ and its downstream gene target, CD36, as well as the levels of FAS were also significantly higher in the HFD LKO livers compared to controls (FIG. 9B; FIG. 10A, FIG. 10B, and FIG. 10C). Mean±SEM shown; Student's unpaired t-test, $*p<0.05$ compared to control group.

Figure 9B:
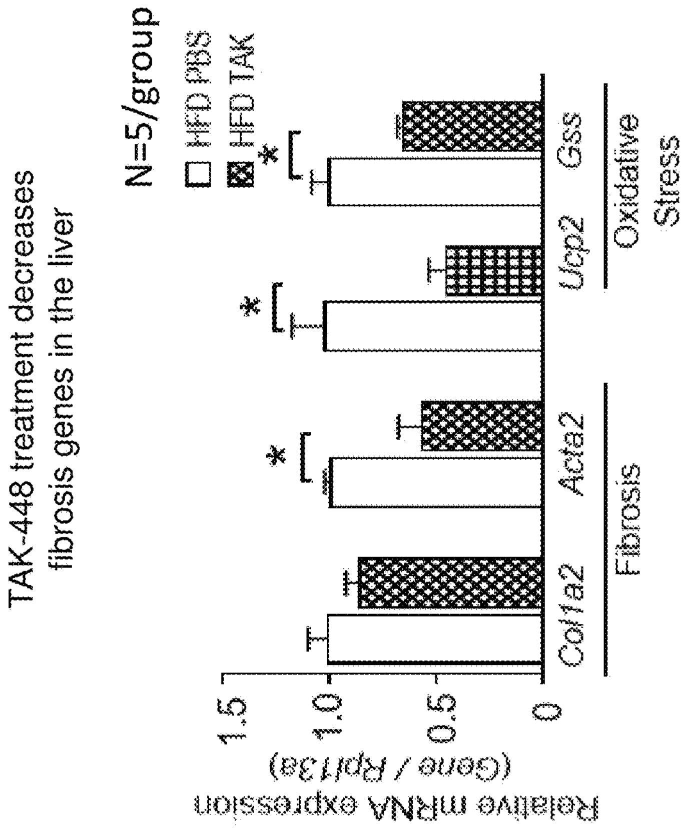
FIG. 9A and FIG. 9B show the relative mRNA expression of inflammatory markers (FIG. 22A) and fibrosis and oxidative stress markers (FIG. 22B) by RT-gPCR in HFD liver samples from mice treated with VEH (controls) or TAK, normalized to Rpl13a mRNA expression. Mean ± SEM shown. Student's unpaired t-test, *p<0.05 compared to VEH controls.
Figure 9A:
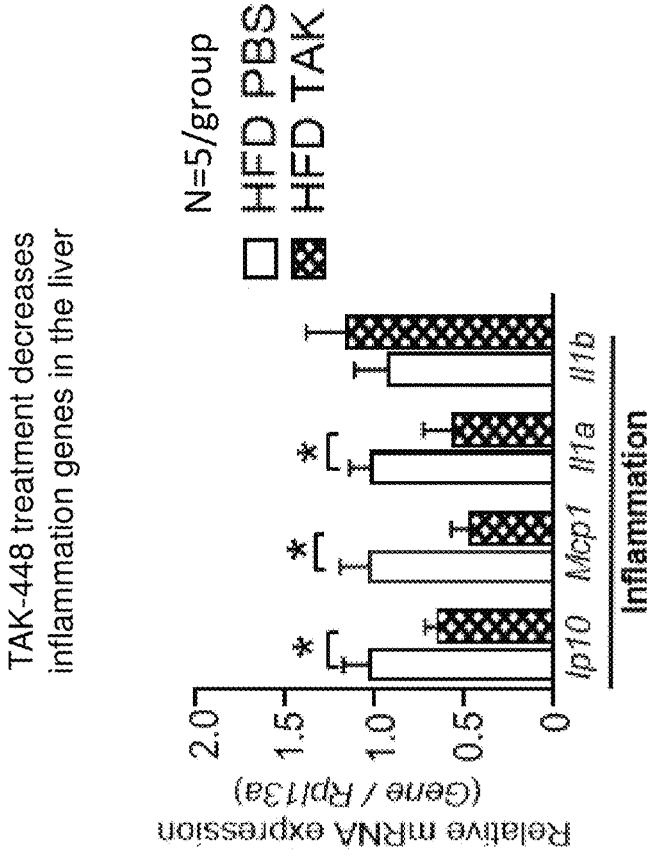

Additionally, LKO livers exhibited suppressed phosphorylation of AMPK (FIG. 9B; FIG. 10D), a protein kinase that when activated inhibits de novo lipogenesis by negatively regulating Srebf1, and its downstream gene targets Acaca and Fasn.

Figure 11:
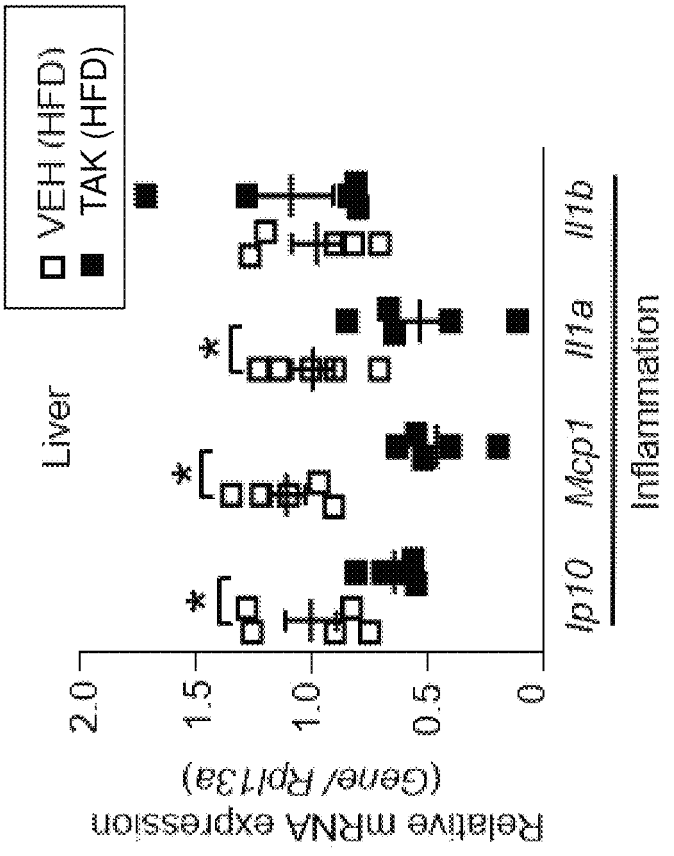

Example 5: Hepatic Kiss1R Knockouts Exhibit Increased Expression of Genes Regulating Triglyceride Synthesis and Enhanced Liver Lipids Levels Triglyceride (TG) synthesis requires glycerol 3-phosphate (G3P), which can be formed by two methods: (a) the glycerol kinase (GYK)-dependent phosphorylation of glycerol and (b) by the glycerol 3-phosphate dehydrogenase (GPD1)-dependent reduction of dihydroxyacetone phosphate. See FIG. 11A, a schematic showing hepatic triglyceride (TG) synthesis pathway; molecules in red are upregulated in HFD LKO and control (CTRL) livers. An analysis of the livers from the HFD LKO mice revealed a significant increase in the hepatic expression of Gyk1 mRNA and protein levels (FIG. 11B, FIG. 9B, and FIG. 12). Gpd1 mRNA levels were also upregulated in LKO HFD livers (see FIG. 11B).

Glycerol enters the liver primarily via aquaglyceroporins (AQP) such as AQP3 and AQP9 (see FIG. 11A). Aqp9 mRNA levels were significantly upregulated in LKO HFD mice livers, whereas Aqp3 levels remain unchanged (FIG. 11B). Many enzymes regulating TG synthesis including GPAT1 (encoded by Gpam) which catalyzes the rate limiting step in TG synthesis, diacylglycerol (DAG) acyltransferase 2 (Dgat2) that acetylates DAG to form TG, and monoacylglycerol acyltransferase 1 (Mogat1) that coverts monoacylglycerol to diacylglycerol (see FIG. 11B), the direct precursor of TG were also upregulated in LKO HFD livers (see FIG. 11A). Taken together, this demonstrates that LKO mice displayed elevated levels of genes regulating TG synthesis.

In order to uncover metabolic differences contributing to the distinct phenotypes observed in LKO mice under HFD conditions, a global, untargeted metabolomic analysis of LKO and control livers was conducted. This revealed that various lipids including TGs, DAG, and phosphatidylcholine were significantly upregulated in HFD LKO livers (FIG. 13A). Similar observations have also been seen in patients with NAFLD and NASH. LKO mice also exhibited other changes. These included high levels of ceramides, phosphatidylglycerol (PG) and cardiolipin. The inhibition of ceramide synthesis was reported to attenuate hepatic steatosis and fibrosis, while PG, a mitochondrial phospholipid, is implicated in multiple metabolic diseases including hepatosteatosis. Cardiolipin is a phospholipid that is essential for optimal mitochondrial function and alterations contribute to mitochondrial dysfunction in multiple tissues including insulin resistance and NAFLD.

Since the data revealed that the loss of hepatic KISS1R resulted in an increase in lipid accumulation in hepatocytes under HFD, possibly via an upregulation of PPARγ and its downstream gene targets, we asked whether this also occurred in livers of LKO mice maintained on RD. Interestingly, LKO mice maintained on RD did not develop steatosis or accumulate TGs. However, Pparg was significantly upregulated with no significant changes in Mogat1, Cd36, or Srebf1 (see FIG. 13B). This suggests that a potential mechanism by which KISS1R signaling regulates hepatic lipogenesis is via PPARγ.

Example 6: Hepatic Kiss1r KO Mice are Glucose Intolerant and Insulin Resistant Since insulin resistance plays an important role in the pathogenesis of NAFLD, metabolic tests were performed to examine the effect of loss of hepatic KISS1R on blood glucose levels. Results showed that compared to HFD controls, HFD LKO mice had significantly higher fasting glucose levels, indicative of elevated gluconeogenesis (FIG. 14A). They were also glucose intolerant (FIG. 14B and FIG. 14C) and insulin resistant (FIG. 14D and FIG. 14E).

Additionally, there was increased expression of key hepatic genes regulating gluconeogenesis, such as G6pc (which converts glucose-6-phosphate to glucose at the terminal step in gluconeogenesis), Pck1 (which converts oxaloacetate to phosphoenolpyruvate), and hepatic glucose transporter GLUT2 encoded by Slc2a2 in the LKO HFD livers (FIG. 14F).

NAFLD can progress to NASH, a state associated with increased inflammation, fibrosis and oxidative stress in the liver. We observed that in LKO mice, after 24 weeks of HFD, there was an upregulation of various markers for inflammation associated with NAFLD such as cytokines macrophage inflammatory protein 2 (Mip2), interleukin 1 isoforms, IL1α and ILβ (encoded by Il1a and Il1b) and chemokines interferon gamma-induced protein 10 (Ip10) and monocyte chemoattractant protein (Mcp1), although the latter was not statistically significant. See FIG. 14G.

LKO mice also exhibited an increase in genes involved in NASH, that are upregulated in early stage of fibrosis. These included collagen (Col1a2) and transforming growth factor β (Tgfb1). An increase in smooth muscle actin (Acta2) and tissue inhibitor of metalloproteinase 1 (Timp1) was also observed but this did not reach significance (see FIG. 14H). Additionally, there was an increase in markers for oxidative stress (Sod1, Sod2, Gss) (see FIG. 14I). Together, these findings suggest that loss of hepatic KISS1R signaling exerts a deleterious effect on the liver, promoting the NAFLD phenotype.

Figure 1E:
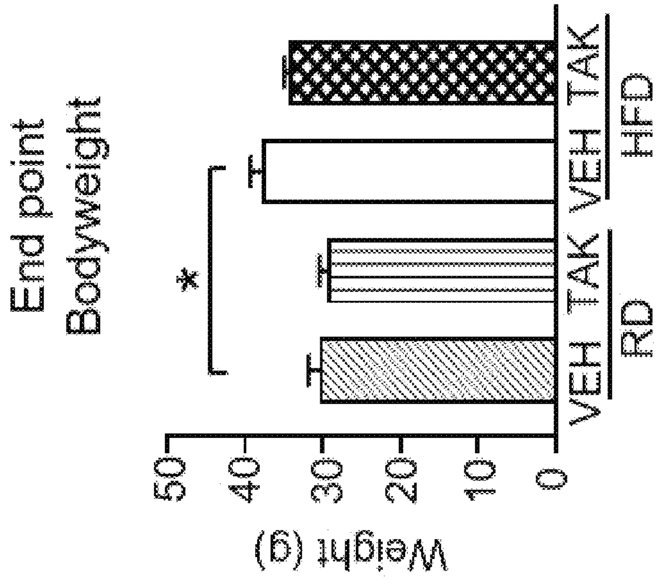

Example 7: Kisspeptin-Analog, TAK-488, Treatment Protects Against Glucose Intolerance and Insulin Resistance in a Mouse Model of NAFLD Based on the data obtained, we next determined the effect of enhanced KISS1R signaling on the development of NAFLD. Wild-type C57BL6J mice (4 weeks of age) were placed on either RD or HFD for 6 weeks. Mice on HFD gained weight (FIG. 15A) and developed insulin resistance resulting in elevated fasting glucose levels (FIG. 15B). Mice (littermates, with similar body weights) were then infused with vehicle (PBS) or a KP-analog (TAK, 0.3 nmol/hour), and further maintained on RD/HFD for another 4 weeks. As expected, HFD control (VEH) mice had significantly higher body weights compared to RD (VEH) control mice (FIG. 1E). However, among the HFD mice, TAK-treated mice had a significantly lower body weight than VEH controls and lower fasting glucose levels compared to VEH group controls (FIG. 1E); these changes occurred without a change in food intake (FIG. 15C). Consistent with these phenotypes, HFD TAK-treated mice were glucose tolerant (FIG. 1I) and insulin sensitive (FIG. 1J) compared to HFD controls.

Figure 1G:
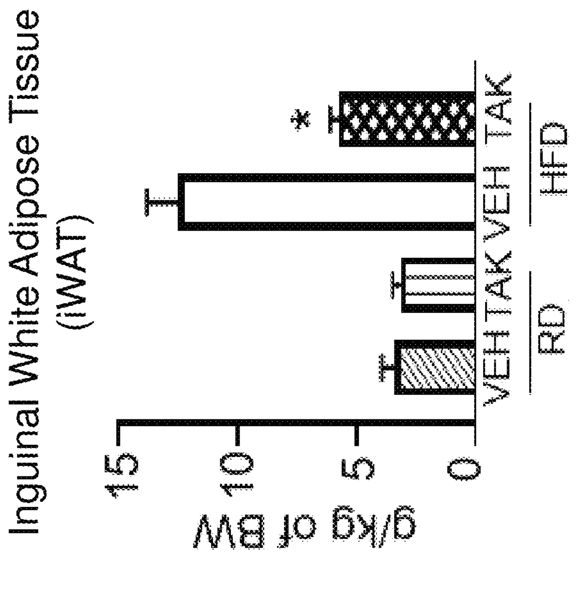
Figure 1F:
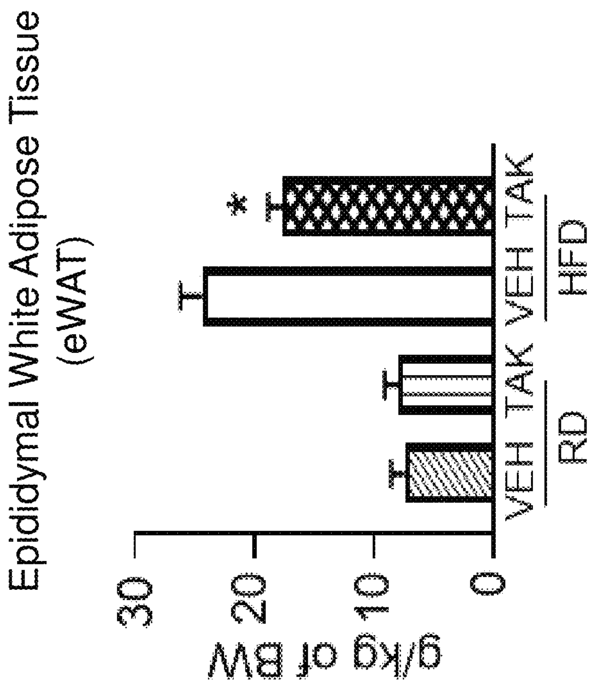
Figure 1H:
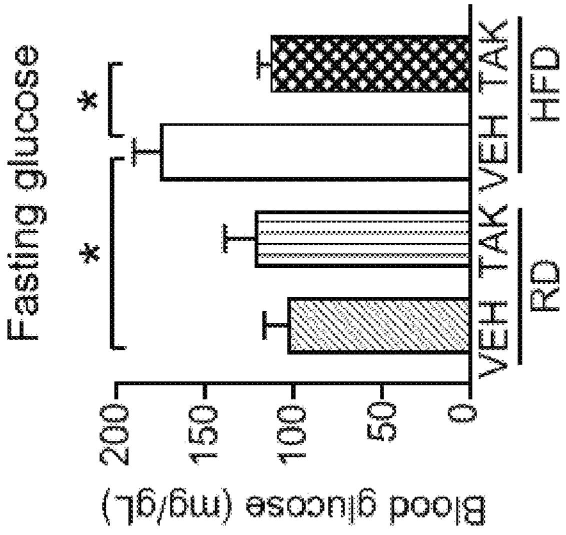
Figure 1I:
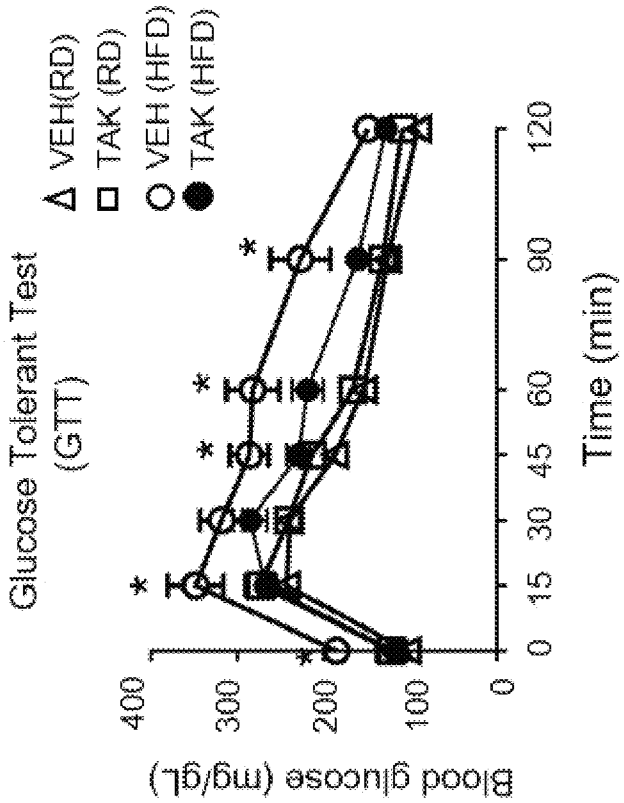
Figure 1J:
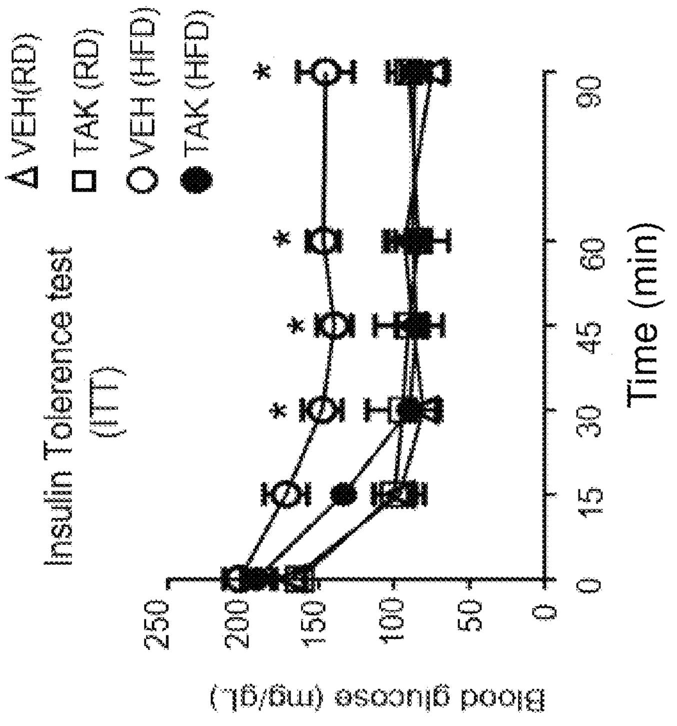

Example 8: Kisspeptin-Analog (TAK-488) Treatment Lowers Liver Steatosis, Circulating Free Fatty Acids and White Adipose Tissue Mass in a Mouse Model of NAFLD In addition to its striking effects on body weights and glucose homeostasis, TAK treatment also protected against the development of steatosis in the HFD mice resulting in a significant decrease in liver and serum TGs (see FIG. 16A). Serum levels of FFA (see FIG. 1D), glycerol (see FIG. 1C), cholesterol (see FIG. 16B), and ALT (see FIG. 16C) were also significantly lower in the TAK-treated group on HFD. Among the HFD groups, analysis of body composition of mice revealed a significant decrease in eWAT and iWAT in the TAK-treated animals (FIG. 1G). CLAMS analysis further revealed that there were no differences in heat production or RER between treated and untreated mice (FIG. 17A and FIG. 17B).

Mechanistically, TAK treatment under HFD conditions significantly reduced the hepatic expression of key regulators of TG synthesis such as PPARγ, CD36 and MOGAT1 (FIG. 18A; FIG. 18B; FIG. 19A; FIG. 19B; FIG. 19C). Furthermore, TAK treatment induced phosphorylation of AMPK (FIG. 20; FIG. 21A), which upon activation inhibits PPARγ transcription. AMPK activation also inhibits lipid synthesis by the acute inhibition of glycerol-3-phosphate acyltransferase (GPAT) activity and by negatively regulating SREBP1 transcription. Gpam (encodes GPAT) expression was significantly reduced in TAK treated livers (FIG. 18A), which could lead to the subsequent decrease in GPAT activity. Although the reduction in Srebf1 was not significant, there was a significant decrease in its downstream target, Fasn (FIG. 18B; FIG. 21B). TAK treatment reduced the expression of Lfabp1 and Gyk1 although this was not significant (FIG. 18A). Finally, TAK-treated livers had lower levels of pro-inflammatory markers (Ip10, Mcp1), as well as markers for fibrosis (Tgfb1, Timp1) and oxidative stress (Ucp2, Gss) (see FIG. 22A and FIG. 22B). Overall, the data suggest that in vivo TAK treatment protects against steatosis, by downregulating lipid synthesis via AMPK activation and this attenuates the development of NAFLD.

Example 9: Kisspeptin Inhibits De Novo Lipogenic Gene Expression and Stimulates AMPK to Inhibit Triglyceride Formation in Isolated Mouse Hepatocytes Since our data revealed that KISS1R signaling inhibits steatosis in vivo, a direct effect of KP on hepatic lipogenesis was examined using primary mouse hepatocytes cultured in the presence or absence of a mixture of FFAs (150 μM palmitate and 150 μM oleate conjugated to bovine serum albumin (BSA) carrier. KP (100 nM) or TAK (3 nM) treatment of FFA loaded hepatocytes isolated from wild-type animals substantially decreased TG accumulation (FIG. 23A; (n=4). *$p<0.05$). KP treatment also reduced the expression of de novo lipogenic genes in primary mouse hepatocytes isolated from C57BL6 male mice upon kisspeptin (KP) or TAK treatment for 8 hours (FIG. 23B) and stimulated phosphorylation of AMPK and its downstream target, ACC (FIG. 23C, FIG. 24A, FIG. 24B) which shows representative western blots showing the effect of kisspeptin treatment on phosphorylation of AMPK and its downstream substrate ACC in primary mouse hepatocytes (n=4).

Phosphorylation of ACC reduces its activity, thereby inhibiting de novo lipogenesis (see FIG. 23C; FIG. 24B). Hepatocytes isolated from RD liver KISS1R knock-out (LKO) mice demonstrated elevated levels of CD36, FAS, PPARγ, and MOGAT1 (see FIG. 25A, FIG. 25B; FIG. 26A through FIG. 26D). Collectively, based on the data, we suggest that activation of KISS1R negatively regulates hepatic lipid content by activating AMPK, which then inhibits de novo lipogenesis, in addition to inhibiting PPARγ and its downstream signaling pathways (see FIG. 27).

REFERENCES

All references listed below and throughout the specification are hereby incorporated by reference in their entirety.

1. U.S. Pat. No. 7,625,869 to Takeda.
2. Dudek et al., Frontiers Endocrinol., 9(145):1-8, 2018.
3. Wang et al., Frontiers Physiol., 9(209): 1-13, 2018.

4. Song et al., Cell Metab., 19(4):667-681, 2014.
5. Tolson et al, J. Clin. Invest., 124(7):3075-3079, 2014.
6. Wolfe and Hussain, Frontiers Endocrinol. (Lausanne), 9(184), 2018.
7. International Application No. PCT/JP2007/071169.
8. Machado Cortez-Pinto, World J. Gastroenterol. 20(36): 12956-12980, 2014.
9. Younossi et al., Hepatol., 64(1):73-84, 2016.
10. Younossi et al., Hepatol. 64(5):1577-1586, 2016.
11. Diehl and Day, N. Engl. J. Med., 377(21):2063-2072, 2017.
12. Wong et al., Gastroenterol., 148(3):547-555, 2015.
13. Bhattacharya and Babwah, Endocrinol., 156(4):1218-1227. 2015.
14. Seminara et al., N. Engl. J. Med., 349(17):1614-1627, 2003.
15. Shoji et al., Peptides, 31(10):1920-1925, 2010.
16. Foretz et al., Int. J. Mol. Sci., 19(9), 2018.
17. Browning and Horton, J. Clin. Invest., 114(2):147-152, 2004.
18. Jelen et al., J. Biol. Chem., 286(52):44319-44325, 2011.
19. Rodriguez et al., Cell Cycle., 10(10):1548-1556, 2011.
20. Puri et al., Hepatol., 46(4):1081-1090, 2007.
21. Zhang et al., Cell. Mol. Gastroenterol. Hepatol., 7(4): 763-781, 2019.
22. Abdelmalek, Nat. Rev. Gastroenterol. Hepato., 13(12): 685-686, 2016.
23. Diehl and Day, N. Engl. J. Med., 377(21):2063-2072, 2017.
24. Ng et al., Lancet, 384(9945):766-781, 2014.
25. Izzi-Engbeaya et al., Diabetes Obes. Metab., 20(12): 2800-2810, 2018.
26. MacLean et al., J. Clin. Endocrinol. Metab. 99(8): E1445-E1453, 2014.
27. Asami et al., J. Med. Chem., 56(21):8298-8307, 2013.
28. Paradies et al., Antioxid. Redox. Signal. 20(12):1925-1953, 2014.
29. Paradies et al., World J. Gastroenterol., 20(39):14205-14218, 2014.
30. Petrosillo et al., Biochim. Biophys. Acta, 1767(10): 1260-1267, 2007.
31. Tarantino et al., J. Clin. Med., 9(1), 2019.
32. Friedman et al., Nat. Med., 24(7):908-922, 2018.
33. Chang et al., Sci. Rep., 5:10096, 2015.
34. Haukeland et al., J. Hepatol., 44(6):1167-1174, 2006.
35. Mirea et al., Trends Mol. Med., 24(5):458-471, 2018.
36. Syn et al., Clin. Liver Dis., 13(4):565-580, 2009.
37. Rakhshandehroo et al., PPAR Res. 2010; 2010.
38. Thompson et al., Am. J. Physiol. Endocrinol. Metab., 291(5):E1074-1082, 2006.
39. Calder et al., Endocrinol., 155(8):3065-3078, 2014.
40. Sozio et al., Am. J. Physiol. Gastrointest. Liver Physiol., 301(4):G739-G747, 2011.
41. Li et al., Cell. Metab., 13(4):376-388, 2011.
42. Nagarajan et al., Am. J. Physiol. Endocrinol. Metab., 316(4):E578-E589, 2019.
43. Munday et al., Eur. J. Biochem., 175(2):331-338, 1998.
44. Millar and Babwah, Neuroendocrinol., 101(3):193-210, 2015.
45. Lambert et al., Gastroenterol., 146(3):726-735, 2014.
46. Hwahng et al., Hepatol., 49(6):1913-1925, 2019.
47. Smith et al., Am. J. Physiol. Endocrinol. Metab., 311 (4):E730-E740, 2016.
48. Green et al., Cell Signal., 23(12):2005-2012, 2011.
49. Willows et al., Biochem. J., 474(17):3059-3073, 2017.
50. Kirby et al., Pharmacol. Rev., 62(4):565-578, 2010.
51. Bedoucha et al., J. Hepatol., 35(1):17-23, 2001.
52. Memon et al., Endocrinol., 141(11):4021-4031, 2000.
53. Li et al., Proc. Natl. Acad. Sci. U.S.A., 111(36):13163-13168, 2014.
54. Mazzucotelli et al., Diabetes, 56(10):2467-2475, 2007.
55. Lasar et al., Cell. Rep., 22(3):760-773, 2018.
56. Guan et al., Genes Dev., 19(4):453-461, 2005.
57. Tontonoz et al., Cell, 93(2):241-252, 1998.
58. Lee et al., *Proc. Natl. Acad. Sci. U.S.A.,* 109(34):13656-13661, 2012.
59. Yu et al., *Sci. Rep.,* 6:29352, 2016.
60. Wolf Greenstein et al., *J. Endocrinol.,* 232(1):107-121, 2017.
61. Hall et al., *J. Lipid Res.,* 53(5):990-999, 2012.
62. Yu et al., *Biochem. Biophys. Res. Commun.,* 460(3):715-720, 2015.
63. Savage et al., *Physiol. Rev.,* 87(2):507-520, 2007.
64. Novaira et al., *Mol. Endocrinol.,* 28(2):225-238, 2014.
65. Zajac et al., *PLoS One,* 6(6):e21599, 2011.
66. Cvetkovic et al., *Endocrinol.,* 154(6):1999-2014, 2013.
67. Dragan et al., *Cell Death Dis.,* 11(2):106, 2020.
68. Blake et al., *Sci. Rep.,* 7:46525, 2017.
69. Kalemba et al., *J. Biol. Chem.,* 294(48):18017-18028, 2019.
70. Curtis et al., *Am. J. Physiol. Endocrinol. Metab.* 298: E296-E303, 2009.
71. Nishizawa et al., *Bioorg. Med. Chem. Lett.* 29(4):654-658, 2019.
72. Decourt et al., Scientific Rep. 6:26908, 2016

The invention claimed is:

1. A method of reducing fat in the liver of a subject suffering from a fatty liver, comprising administering to the subject a therapeutically effective amount of a compound selected from TAK-448 and any salt thereof, and kisspeptin-10 and any salt thereof.

2. The method of claim 1, wherein the subject has a condition selected from alcoholism, hepatitis, non-alcoholic fatty liver disease (NALFD), and non-alcoholic steatohepatitis (NASH).

3. The method of claim 1, wherein the subject has non-alcoholic fatty liver disease (NALFD) or non-alcoholic steatohepatitis (NASH).

4. The method of claim 1, further comprising administering a therapeutic amount of a second compound selected from AKR-001, aramchol, ASC40, AZD7687, BIO89-100, BMS-986036, canagliflozin, cenicriviroc, cilofexor, dapagliflozin, EDP-305, elafibranor, emricasan, EYP001a, fenofibrate, firsocostat, GR-MD-02, IONIS-DGAT2Rx, ipragliflozin, licogliflozin, luseogliflozin, LY3202328, MET409, metformin, MGL-3196, MK-4074, MSDC-0602K, MT-3995, NGM282, nidufexor, PF-05221304, PF-06835919, PF-06865571, PF-06882961, PX-102, PXL770, PXS-5153A, selonsertib, simtuzumab, TERN-101, TERN-201, troifexor, vitamin D, vitamin E, and VK2809.

5. The method of claim 1, wherein the administration is subcutaneous, intravenous, or oral administration.

* * * * *

SEQUENCE LISTING

```
<160> NUMBER OF SEQ ID NOS: 106

<210> SEQ ID NO 1
<211> LENGTH: 52
<212> TYPE: PRT
<213> ORGANISM: Mus musculus
<220> FEATURE:
<221> NAME/KEY: MISC_FEATURE
<223> OTHER INFORMATION: 3' NH2

<400> SEQUENCE: 1

Ser Ser Pro Cys Pro Pro Val Glu Gly Pro Ala Gly Arg Gln Arg Pro
1               5                   10                  15

Leu Cys Ala Ser Arg Ser Arg Leu Ile Pro Ala Pro Arg Gly Ala Val
            20                  25                  30
```

-continued

```
Leu Val Gln Arg Glu Lys Asp Leu Ser Thr Tyr Asn Trp Asn Ser Phe
        35                  40                  45

Gly Leu Arg Tyr
    50


<210> SEQ ID NO 2
<211> LENGTH: 54
<212> TYPE: PRT
<213> ORGANISM: Homo sapiens
<220> FEATURE:
<221> NAME/KEY: MISC_FEATURE
<223> OTHER INFORMATION: 3' NH2

<400> SEQUENCE: 2

Gly Thr Ser Leu Ser Pro Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50


<210> SEQ ID NO 3
<211> LENGTH: 10
<212> TYPE: PRT
<213> ORGANISM: Homo sapiens
<220> FEATURE:
<221> NAME/KEY: MISC_FEATURE
<223> OTHER INFORMATION: 3' NH2

<400> SEQUENCE: 3

Tyr Asn Trp Asn Ser Phe Gly Leu Arg Phe
1               5                   10


<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza
<220> FEATURE:
<221> NAME/KEY: MOD_RES
<222> LOCATION: (8)..(8)
<223> OTHER INFORMATION: Me

<400> SEQUENCE: 4

Tyr Trp Asn Thr Phe Gly Leu Arg Trp
1               5


<210> SEQ ID NO 5
<211> LENGTH: 10
<212> TYPE: PRT
```

<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2

<400> SEQUENCE: 5

Tyr Asn Trp Asn Ser Phe Gly Leu Arg Phe
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2

<400> SEQUENCE: 6

Trp Asn Trp Asn Ser Phe Ser Leu Arg Phe
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2

<400> SEQUENCE: 7

Tyr Asn Trp Arg Ser Phe Gly Leu Arg Phe
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2

<400> SEQUENCE: 8

Tyr Asn Trp Asn Ser Phe Leu Arg Phe
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: Me

<400> SEQUENCE: 9

Tyr Asn Trp Asn Ser Phe Gly Leu Arg Phe
1 5 10

<210> SEQ ID NO 10
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION

<400> SEQUENCE: 10

Tyr Asn Trp Asn Ser Phe Gly Leu Arg Phe
1 5 10

<210> SEQ ID NO 11
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza
<220> FEATURE:
<221> NAME/KEY: MOD_RES
<222> LOCATION: (8)..(8)
<223> OTHER INFORMATION: Me

<400> SEQUENCE: 11

Tyr Trp Asn Thr Phe Gly Leu Arg Trp
1 5

<210> SEQ ID NO 12
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza
<220> FEATURE:
<221> NAME/KEY: MOD_RES
<222> LOCATION: (8)..(8)
<223> OTHER INFORMATION: Me -continued

<400> SEQUENCE: 12

Tyr Trp Asn Thr Phe Gly Leu Arg Trp
1 5

<210> SEQ ID NO 13
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza

<400> SEQUENCE: 13

Tyr Trp Asn Thr Phe Gly Leu Arg Trp
1 5

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza
<220> FEATURE:
<221> NAME/KEY: MOD_RES
<222> LOCATION: (8)..(8)
<223> OTHER INFORMATION: Me

<400> SEQUENCE: 14

Tyr Trp Asn Thr Phe Gly Ala Arg Trp
1 5

<210> SEQ ID NO 15
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' CH3-NH2
<220> FEATURE:
<221> NAME/KEY: MOD_RES
<222> LOCATION: (1)..(1)

<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza
<220> FEATURE:
<221> NAME/KEY: MOD_RES
<222> LOCATION: (8)..(8)
<223> OTHER INFORMATION: Me

<400> SEQUENCE: 15

Tyr Trp Asn Ser Phe Gly Leu Arg Trp
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (8)..(8)
<223> OTHER INFORMATION: Me

<400> SEQUENCE: 16

Tyr Trp Asn Thr Phe Gly Leu Arg Trp
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza
<220> FEATURE:
<221> NAME/KEY: MOD_RES
<222> LOCATION: (7)..(7)
<223> OTHER INFORMATION: Me

<400> SEQUENCE: 17

Tyr Trp Asn Thr Phe Gly Arg Trp
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 18

Tyr Asn Trp Asn Ser Phe Gly Leu Arg Phe
1 5 10

<210> SEQ ID NO 19
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 19

Ala Asn Trp Asn Ser Phe Gly Leu Arg Phe
1 5 10

<210> SEQ ID NO 20
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 20

Tyr Ala Trp Asn Ser Phe Gly Leu Arg Phe
1 5 10

<210> SEQ ID NO 21
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 21

Tyr Asn Ala Asn Ser Phe Gly Leu Arg Phe
1 5 10

<210> SEQ ID NO 22
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 22

Tyr Asn Trp Ala Ser Phe Gly Leu Arg Phe
1 5 10

<210> SEQ ID NO 23
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 23

Tyr Asn Trp Asn Ala Phe Gly Leu Arg Phe
1 5 10

<210> SEQ ID NO 24
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 24

Tyr Asn Trp Asn Ser Ala Gly Leu Arg Phe
1 5 10

<210> SEQ ID NO 25
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 25

Tyr Asn Trp Asn Ser Phe Ala Leu Arg Phe
1 5 10

<210> SEQ ID NO 26
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 26

Tyr Asn Trp Asn Ser Phe Gly Ala Arg Phe
1 5 10

<210> SEQ ID NO 27
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 27

Tyr Asn Trp Asn Ser Phe Gly Leu Ala Phe 1 5 10

<210> SEQ ID NO 28
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 28

Tyr Asn Trp Asn Ser Phe Gly Leu Arg Ala
1 5 10

<210> SEQ ID NO 29
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 29

Phe Asn Trp Asn Ser Phe Gly Leu Arg Phe
1 5 10

<210> SEQ ID NO 30
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 30

Tyr Asp Trp Asn Ser Phe Gly Leu Arg Phe
1 5 10

<210> SEQ ID NO 31
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 31

Tyr Asn Trp Asp Ser Phe Gly Leu Arg Phe
1 5 10

<210> SEQ ID NO 32
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 32

-continued

```
Tyr Asn Trp Asn Thr Phe Gly Leu Arg Phe
1               5                   10


<210> SEQ ID NO 33
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 33

Tyr Asn Trp Asn Ser Tyr Gly Leu Arg Phe
1               5                   10


<210> SEQ ID NO 34
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 34

Tyr Asn Trp Asn Ser Phe Gly Ile Arg Phe
1               5                   10


<210> SEQ ID NO 35
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 35

Tyr Asn Trp Asn Ser Phe Gly Leu Lys Phe
1               5                   10


<210> SEQ ID NO 36
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' NH2

<400> SEQUENCE: 36

Tyr Asn Trp Asn Ser Phe Gly Leu Arg His
1               5                   10


<210> SEQ ID NO 37
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
```

<222> LOCATION: (1)..(1)
<223> OTHER INFORMATION: D-amino acid

<400> SEQUENCE: 37

Tyr Asn Trp Asn Ser Phe Gly Leu Arg Phe
1 5 10

<210> SEQ ID NO 38
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (6)..(6)
<223> OTHER INFORMATION: D-amino acid

<400> SEQUENCE: 38

Tyr Asn Trp Asn Ser Phe Gly Leu Arg Phe
1 5 10

<210> SEQ ID NO 39
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (10)..(10)
<223> OTHER INFORMATION: D-amino acid

<400> SEQUENCE: 39

Tyr Asn Trp Asn Ser Phe Gly Leu Arg Phe
1 5 10

<210> SEQ ID NO 40
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MOD_RES
<222> LOCATION: (6)..(6)
<223> OTHER INFORMATION: aza
<220> FEATURE:
<221> NAME/KEY: MOD_RES
<222> LOCATION: (8)..(8)
<223> OTHER INFORMATION: Me

<400> SEQUENCE: 40

Tyr Trp Asn Thr Phe Gly Leu Arg Trp
1 5

<210> SEQ ID NO 41
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION

<400> SEQUENCE: 41

Tyr Asn Trp Asn Ser Phe Gly Leu Arg Tyr
1               5                   10

<210> SEQ ID NO 42
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Palm-gamma
<220> FEATURE:
<221> NAME/KEY: MOD_RES
<222> LOCATION: (5)..(6)
<223> OTHER INFORMATION: Psi[Tz]

<400> SEQUENCE: 42

Tyr Lys Asp Trp Gly Leu Arg Tyr
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Palm-gamma
<220> FEATURE:
<221> NAME/KEY: MOD_RES
<222> LOCATION: (8)..(9)
<223> OTHER INFORMATION: Psi[Tz]

<400> SEQUENCE: 43

Tyr Asn Lys Asp Asn Ser Phe Gly Leu Arg Tyr
1               5                   10

<210> SEQ ID NO 44

-continued

<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: Palm-gamma
<220> FEATURE:
<221> NAME/KEY: MOD_RES
<222> LOCATION: (8)..(9)
<223> OTHER INFORMATION: Psi[Tz]

<400> SEQUENCE: 44

Asp Tyr Asn Trp Asn Ser Phe Gly Leu Arg Tyr
1 5 10

<210> SEQ ID NO 45
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: Palm-gamma
<220> FEATURE:
<221> NAME/KEY: MOD_RES
<222> LOCATION: (8)..(9)
<223> OTHER INFORMATION: Psi[Tz]
<220> FEATURE:
<221> NAME/KEY: MOD_RES
<222> LOCATION: (10)..(10)
<223> OTHER INFORMATION: Me

<400> SEQUENCE: 45

Asp Tyr Asn Trp Asn Ser Phe Gly Leu Arg Tyr
1 5 10

<210> SEQ ID NO 46
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(8)
<223> OTHER INFORMATION: Psi[Tz]
<220> FEATURE:
<221> NAME/KEY: MOD_RES
<222> LOCATION: (9)..(9)
<223> OTHER INFORMATION: Me

<400> SEQUENCE: 46

Tyr Asn Trp Asn Ser Phe Gly Leu Arg Tyr
1 5 10

<210> SEQ ID NO 47
<211> LENGTH: 22
<212> TYPE: DNA
<213> ORGANISM: Artificial Sequence
<220> FEATURE:
<223> OTHER INFORMATION: Synthetic

<400> SEQUENCE: 47
gcagagccag gagaactttg ag 22

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
tttgattttc ttcccttcat gca 23

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
gatgacgtgg caaagaacag 20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tcctcggggt cctgagttat 20

<210> SEQ ID NO 51
<211> LENGTH: 21
<212> TYPE: DNA
<213> ORGANISM: Artificial Sequence
<220> FEATURE:
<223> OTHER INFORMATION: Synthetic

<400> SEQUENCE: 51
atgggcggaa tggtctcttt c 21

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52
tggggacctt gtcttcatca t 21

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
ggaggtggtg atagccggta t 21

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
tgggtaatcc atagagccca g 21

<210> SEQ ID NO 55
<211> LENGTH: 22
<212> TYPE: DNA
<213> ORGANISM: Artificial Sequence
<220> FEATURE:
<223> OTHER INFORMATION: Synthetic

<400> SEQUENCE: 55
atccgctggc taagagacaa cc 22

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
tgcactgggc tcccaataag g 21

<210> SEQ ID NO 57
<211> LENGTH: 23
<212> TYPE: DNA
<213> ORGANISM: Artificial Sequence
<220> FEATURE:
<223> OTHER INFORMATION: Synthetic

<400> SEQUENCE: 57
aaaaagccaa cgtatggatt ccg 23

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58
cagcaaggta gatccggga 19

<210> SEQ ID NO 59
<211> LENGTH: 19
<212> TYPE: DNA
<213> ORGANISM: Artificial Sequence
<220> FEATURE:
<223> OTHER INFORMATION: Synthetic

<400> SEQUENCE: 59
agcattcaac gccaggttc 19

<210> SEQ ID NO 60
<211> LENGTH: 23

<212> TYPE: DNA
<213> ORGANISM: Artificial Sequence
<220> FEATURE:
<223> OTHER INFORMATION: Synthetic

<400> SEQUENCE: 60
cgagtctgtc agttcaatac caa 23

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
ccactgtttt gggactctct 20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
cgggtgtgtt cttcaaagtc 20

<210> SEQ ID NO 63
<211> LENGTH: 22
<212> TYPE: DNA
<213> ORGANISM: Artificial Sequence
<220> FEATURE:
<223> OTHER INFORMATION: Synthetic

<400> SEQUENCE: 63
cccagacaga agtcatagcc ac 22

<210> SEQ ID NO 64
<211> LENGTH: 21
<212> TYPE: DNA
<213> ORGANISM: Artificial Sequence
<220> FEATURE:
<223> OTHER INFORMATION: Synthetic

<400> SEQUENCE: 64
gccttgcctt tgttcagtat c 21

<210> SEQ ID NO 65
<211> LENGTH: 22
<212> TYPE: DNA
<213> ORGANISM: Artificial Sequence
<220> FEATURE:
<223> OTHER INFORMATION: Synthetic

<400> SEQUENCE: 65
aatgagtagc agcaggtgag tg 22

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
gaagccagct ctctcttcct c 21

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
cgcttgagtc ggcaaagaaa 20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
tgatactgtc acccggctct 20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
aagtgctgcc gtcatttctt 20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
gtggcaatga tctcaacacg 20

<210> SEQ ID NO 71
<211> LENGTH: 22
<212> TYPE: DNA
<213> ORGANISM: Artificial Sequence
<220> FEATURE:
<223> OTHER INFORMATION: Synthetic

<400> SEQUENCE: 71
tgacgtcact ggagttgtac gg 22

<210> SEQ ID NO 72
<211> LENGTH: 21
<212> TYPE: DNA
<213> ORGANISM: Artificial Sequence
<220> FEATURE:
<223> OTHER INFORMATION: Synthetic

<400> SEQUENCE: 72
ggttcatgtc atggatggtg c 21

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ctgccacaga cgtcactttc 20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
acataccagc ggtccacact 20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
agctgctgct tctcctctgt 20

<210> SEQ ID NO 76
<211> LENGTH: 19
<212> TYPE: DNA
<213> ORGANISM: Artificial Sequence
<220> FEATURE:
<223> OTHER INFORMATION: Synthetic

<400> SEQUENCE: 76
gcataccgcg attcctttt 19

<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77
cgacatgagt tcctttatga tggg 24

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
tgtgatctct tgcacggctt 20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
gcagggttcc aacgatgttg 20

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
gcagccatcg actaggacag a 21

<210> SEQ ID NO 81
<211> LENGTH: 22
<212> TYPE: DNA
<213> ORGANISM: Artificial Sequence
<220> FEATURE:
<223> OTHER INFORMATION: Synthetic

<400> SEQUENCE: 81
ccttgcaaac tggagagtga ca 22

<210> SEQ ID NO 82
<211> LENGTH: 21
<212> TYPE: DNA
<213> ORGANISM: Artificial Sequence
<220> FEATURE:
<223> OTHER INFORMATION: Synthetic

<400> SEQUENCE: 82
aggcaaagtg atcgctctgg t 21

<210> SEQ ID NO 83
<211> LENGTH: 25
<212> TYPE: DNA
<213> ORGANISM: Artificial Sequence
<220> FEATURE:
<223> OTHER INFORMATION: Synthetic

<400> SEQUENCE: 83
caaccaacaa gtgatattct ccatg 25

<210> SEQ ID NO 84
<211> LENGTH: 21
<212> TYPE: DNA
<213> ORGANISM: Artificial Sequence
<220> FEATURE:
<223> OTHER INFORMATION: Synthetic

<400> SEQUENCE: 84
gatccacact ctccagctgc a 21

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
actgggacga catggaaaag 20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
gttcagtggt gcctctgtca 20

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
gctgctctca aggttgttcg 20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
ccttttcctt ccgtttctcc 20

<210> SEQ ID NO 89
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: See specification as filed for detailed description of substitutions and preferred embodiments

<400> SEQUENCE: 89

Xaa Asn Trp Asn Ser Xaa Xaa Leu Xaa Phe
1 5 10

<210> SEQ ID NO 90
<211> LENGTH: 10
<212> TYPE: PRT
<213> ORGANISM: Artificial Sequence
<220> FEATURE:
<223> OTHER INFORMATION: Synthetic

<400> SEQUENCE: 90

Tyr Asn Trp Asn Ser Phe Gly Leu Arg Phe
1 5 10

<210> SEQ ID NO 91
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (9)..(9)
<223> OTHER INFORMATION: Me

<400> SEQUENCE: 91

Tyr Asn Trp Asn Ser Phe Gly Leu Arg Phe
1 5 10

<210> SEQ ID NO 92
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (6)..(7)
<223> OTHER INFORMATION: Psi(CSNH)
<220> FEATURE:
<221> NAME/KEY: MOD_RES
<222> LOCATION: (9)..(9)
<223> OTHER INFORMATION: Me

<400> SEQUENCE: 92

Tyr Asn Trp Asn Ser Phe Gly Leu Arg Phe
1 5 10

<210> SEQ ID NO 93
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (6)..(7)
<223> OTHER INFORMATION: Psi(CH2NH)
<220> FEATURE:
<221> NAME/KEY: MOD_RES
<222> LOCATION: (9)..(9)
<223> OTHER INFORMATION: Me

<400> SEQUENCE: 93

Tyr Asn Trp Asn Ser Phe Gly Leu Arg Phe
1 5 10

<210> SEQ ID NO 94
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (6)..(7)
<223> OTHER INFORMATION: Psi(NHCO)

<220> FEATURE:
<221> NAME/KEY: MOD_RES
<222> LOCATION: (9)..(9)
<223> OTHER INFORMATION: Me

<400> SEQUENCE: 94

Tyr Asn Trp Asn Ser Phe Gly Leu Arg Phe
1 5 10

<210> SEQ ID NO 95
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 95

Tyr Asn Trp Asn Ser Phe Gly Leu Arg Phe
1 5 10

<210> SEQ ID NO 96
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: See specification as filed for detailed description of substitutions and preferred embodiments

<400> SEQUENCE: 96

Xaa Asn Xaa Asn Ser Phe Xaa Leu Xaa Phe
1 5 10

<210> SEQ ID NO 97
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2

<400> SEQUENCE: 97

Tyr Asn Trp Asn Ser Phe Gly Leu Arg Phe
1 5 10

<210> SEQ ID NO 98
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 98

Tyr Asn Ser Asn Ser Phe Gly Leu Arg Phe
1 5 10

<210> SEQ ID NO 99
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 99

Tyr Asn Thr Asn Ser Phe Gly Leu Arg Phe
1 5 10

<210> SEQ ID NO 100
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 100

Tyr Asn Ile Asn Ser Phe Gly Leu Arg Phe
1 5 10

<210> SEQ ID NO 101

-continued

<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: misc_feature
<222> LOCATION: (3)..(3)
<223> OTHER INFORMATION: Xaa is Cha
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 101

Tyr Asn Xaa Asn Ser Phe Gly Leu Arg Phe
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: misc_feature
<222> LOCATION: (3)..(3)
<223> OTHER INFORMATION: Xaa is Pya(3)
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 102

Tyr Asn Xaa Asn Ser Phe Gly Leu Arg Phe
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: misc_feature
<222> LOCATION: (3)..(3)

<223> OTHER INFORMATION: Xaa is Pya(4)
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 103

Tyr Asn Xaa Asn Ser Phe Gly Leu Arg Phe
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: misc_feature
<222> LOCATION: (3)..(3)
<223> OTHER INFORMATION: Xaa is Nal(2)
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 104

Tyr Asn Xaa Asn Ser Phe Gly Leu Arg Phe
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 105

Tyr Asn Trp Asn Ser Phe Gly Leu Arg Phe
1               5                   10

-continued

```
<210> SEQ ID NO 106
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: 3' NH2
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: D-Pya(4)
<220> FEATURE:
<221> NAME/KEY: MOD_RES
<222> LOCATION: (7)..(7)
<223> OTHER INFORMATION: aza
<220> FEATURE:
<221> NAME/KEY: MOD_RES
<222> LOCATION: (9)..(9)
<223> OTHER INFORMATION: Me

<400> SEQUENCE: 106

Tyr Asn Xaa Asn Ser Phe Gly Leu Arg Phe
1               5                   10
```